United States Patent [19]
Nomoto et al.

[11] Patent Number: 5,606,101
[45] Date of Patent: Feb. 25, 1997

[54] SUBSTITUTE AMIC ACID DERIVATIVES

[75] Inventors: Takashi Nomoto; Masahiro Hayashi; Jun Shibata; Yoshikazu Iwasawa; Morihiro Mitsuya; Yoshiaki IIda; Katsumasa Nonoshita; Yasufumi Nagata, all of Tsukuba, Japan

[73] Assignee: Banyu Pharmaceutical Co., Ltd., Tokyo, Japan

[21] Appl. No.: 540,329

[22] Filed: Oct. 6, 1995

Related U.S. Application Data

[62] Division of Ser. No. 471,081, Jun. 6, 1995, Pat. No. 5,488,149, which is a continuation of Ser. No. 193,850, Feb. 9, 1994, abandoned.

[30] Foreign Application Priority Data

| Feb. 12, 1993 | [JP] | Japan | 5-047364 |
| Sep. 24, 1993 | [JP] | Japan | 5-261713 |
| Sep. 24, 1993 | [JP] | Japan | 5-261714 |

[51] Int. Cl.$^6$ .................... C07C 69/353; C07C 69/34
[52] U.S. Cl. .................... 560/193; 560/190; 560/197; 560/198; 560/199; 549/229; 549/305; 558/276
[58] Field of Search .................... 560/190, 193, 560/197, 198, 199; 549/229, 305; 558/276

[56] References Cited

PUBLICATIONS

Serval et al., Journal of Pharmacology and Experimental Therapeutics, vol. 260, No. 3, pp. 1093–1100 1992.
Kvittingen et al., Biotechnology Letters, vol. 13, No. 1, pp. 13–18.
Lindell et al., Tetrahedron Letters, vol. 31, No. 37, pp. 5381–5484.

Primary Examiner—Joseph Conrad
Assistant Examiner—Barbara S. Frazier
Attorney, Agent, or Firm—Oblon, Spivak, McClelland, Maier, & Neustadt, P.C.

[57] ABSTRACT

A compound of the formula (I) or its pharmaceutically acceptable salt or ester:

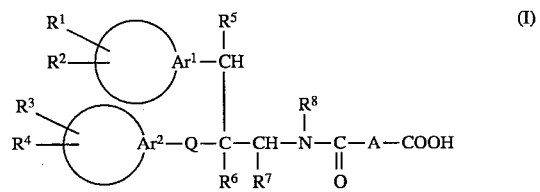

and intermediates thereof.

6 Claims, No Drawings

SUBSTITUTE AMIC ACID DERIVATIVES

This is a division of application Ser. No. 08/471,081 filed on Jun. 6, 1995, allowed Aug. 10, 1995, as U.S. Pat. No. 5,488,149 which is a continuation of application Ser. No. 08/193,850 filed Feb. 9, 1994, abandoned.

The present invention relates to novel substituted amic acid derivatives, a process for their production and their use. More particularly, the substituted amic acid derivatives of the present invention have squalene synthase-inhibitory activities and are thus useful for treatment and prophylaxis of hypercholesterolemia, hyperlipemia and arteriosclerosis. Further, the substituted amic acid derivatives of the present invention have antifungal activities and are thus useful also as therapeutic and preventive agents for fungus infectious diseases.

In recent years, increases of arteriosclerosis and accompanying coronary and cerebral disorders due to changes in the eating habits and an increase of old aged population, have been pointed out. Various factors are thought to predipose to development of arteriosclerosis. However, an increase of cholesterol level in blood is one of the most major risk factors, and it is known that an agent for reducing cholesterol level in blood is effective for the treatment and prophylaxis of arteriosclerosis (Agents Used to Treat Hyperlipidemia, Drug Evaluations 6th. edition, 903–926 (1986)).

The biosynthesis of cholesterol in vivo is generally as follows.

Presently commercially available lovastatin, pravastatin and simvastatin are excellent hypocholesterolemic agents which selectively inhibit 3-hydroxy-3-methylglutaryl-CoA (hereinafter referred to simply as HMG-CoA) reductase and thus block the biosynthesis of cholesterol. However, these HMG-CoA reductase inhibitors inhibit relatively early stage in the cholesterol biosynthesis pathway and thus have a drawback that they also inhibit the biosynthesis of ubiquinone, dolichol, isopentenyl t-RNA, etc. which are essential for organism.

On the other hand, squalene synthase is an enzyme which works at relatively late stage in the pathway, as compared with the HMG-CoA reductase, and an agent capable of inhibiting the squalene synthase is expected to be a safer hypocholesterolemic agent with less side effects.

Further, if an agent is capable of inhibiting the squalene synthase in a biosynthesis system of sterol which is an essential constituting component of a fungus cell membrane and thus capable of inducing a cell membrane disorder and suppressing the growth of fungus, such an agent may be developed as an antifungal agent.

As compounds having squalene synthase inhibitory activities, compounds disclosed in Japanese Unexamined Patent Publication No. 279589/1992, U.S. Pat. No. 5,135,935, PCT Publication No. 92/15579 and European Patent 513760, etc., are known. However, they still have some problems to be solved before they can be used in the field of medical treatment.

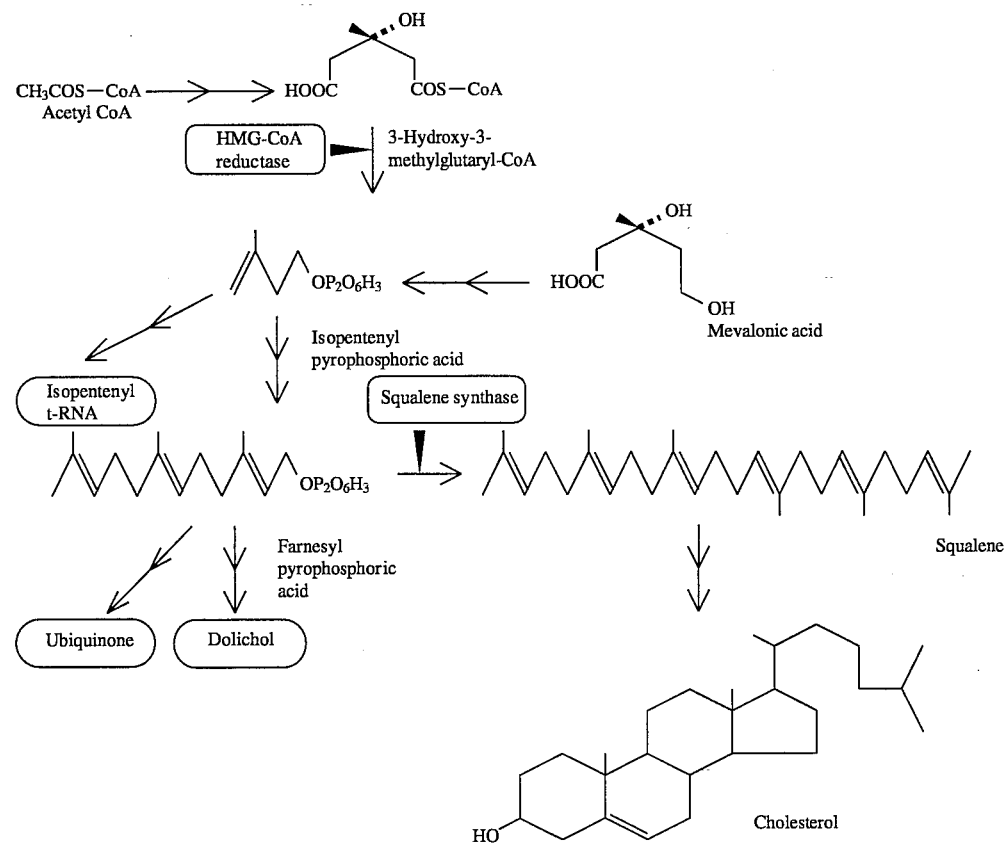

As compounds having the most resembled structure to that of compounds of the present invention, a group of compounds disclosed in J. Med. Chem., 10, 717 (1967) may be mentioned, and this literature discloses that such compounds have cholesterol-lowering activities. However, the group of compounds disclosed in the literature are characterized in that they have a maleamic acid structure, and the mode of action in their cholesterol-lowering activities is different from the squalene synthase-inhibitory activities. Therefore, the disclosed compounds are fundamentally different from the compounds of the present invention.

It is an object of the present invention to provide a therapeutic and prophylaxis agent for hypercholesterolemia, hyperlipemia and arteriosclerosis, which is safe and effective and has less side effects than the conventional drugs by virtue of its squalene synthase inhibitory activities. Another object of the present invention is to provide an antifungal agent more useful than the conventional antifungal agents by inhibiting the squalene synthase in the sterol biosynthesis system of fungus.

The present inventors have found that a compound of the formula (I):

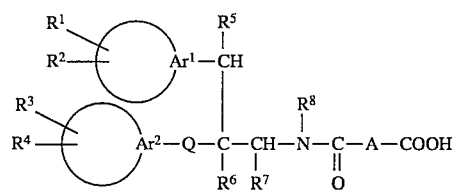

wherein each of

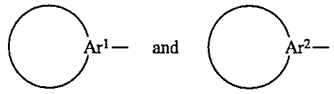

which are the same or different, is an aryl group or a heteroaromatic ring group; A is a $C_{3-8}$ linear saturated or unsaturated aliphatic hydrocarbon group which may have substituent(s) selected from the group consisting of a lower alkyl group, a hydroxyl group, a lower alkoxy group, a carboxyl group, an aryl group and an aralkyl group; Q is a single bond or a group of the formula —CO—O—, —O—CO—, —CH$_2$CH$_2$—, —CH=CH—, —OCH$_2$—, —SCH$_2$—, —CH$_2$O— or —CH$_2$S—; each of $R^1$, $R^2$, $R^3$ and $R^4$ which are the same or different, is a hydrogen atom, a halogen atom, a lower alkyl group, a hydroxyl group, a lower alkoxy group, or an aryl or heteroaromatic ring group which may have substituent(s) selected from the group consisting of a halogen atom, a lower alkyl group and a lower alkoxy group; each of $R^5$, $R^6$ and $R^7$ which are the same or different, is a hydrogen atom or a lower alkyl group; and $R^8$ is a hydrogen atom, a lower alkyl group, a lower alkenyl group, a lower alkynyl group or an aralkyl group, provided that when Q is a single bond,

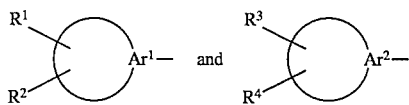

are not simultaneously 4-chlorophenyl groups, has squalene synthase inhibitory activities and is thus useful for the treatment and prophylaxis of hypercholesterolemia, hyperlipemia and arteriosclerosis, and further that the same compound has antifungal activities and is thus useful also as a therapeutic agent and a preventive agent for fungus infectious diseases. The present invention has been accomplished on the basis of these discoveries.

Thus, the present invention provides the compound of the formula (I), its pharmaceutically acceptable salt or ester, a process for its production and its use.

Further, the present invention provides the following compounds as intermediates:

A compound of the formula (II'):

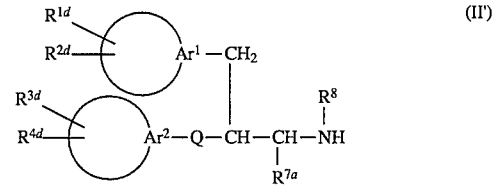

wherein

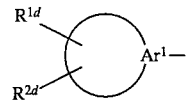

is a group of the formula

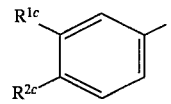

(wherein each of $R^{1c}$ and $R^{2c}$ which are the same or different, is a hydrogen atom, a halogen atom, a lower alkyl group or a lower alkoxy group) or a naphthyl group;

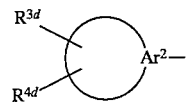

is a group of the formula

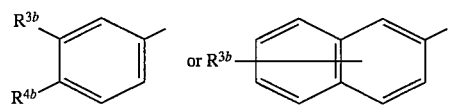

(wherein $R^{3b}$ is a hydrogen atom, a halogen atom, a lower alkyl group or a lower alkoxy group; and $R^{4b}$ is a hydrogen atom, a halogen atom, a lower alkyl group, a lower alkoxy group, or an aryl or heteroaromatic ring group which may have substituent(s) selected from the group consisting of a halogen atom, a lower alkyl group and a lower alkoxy group, provided that when Q is a single bond, $R^{4b}$ is an aryl or heteroaromatic ring group which may have substituent(s) selected from the group consisting of a halogen atom, a lower alkyl group and a lower alkoxy group); Q is a single bond or a group of the formula —CO—O—, —O—CO—, —CH$_2$CH$_2$—, —CH=CH—, —OCH$_2$—, —SCH$_2$—, —CH$_2$O— or —CH$_2$S—; $R^{7a}$ is a lower alkyl group; and $R^8$ is a hydrogen atom, a lower alkyl group, a lower alkenyl group, a lower alkynyl group or an aralkyl group.

A compound of the formula (III-b$^1$):

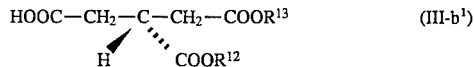

wherein each of $R^{12}$ and $R^{13}$ which are the same or different, is a carboxyl-protecting group, or the formula (III-b$^2$):

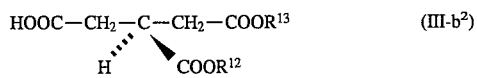

wherein $R^{12}$ and $R^{13}$ are as defined above.

Now, the present invention will be described in detail with reference to the preferred embodiments.

Firstly, the symbols and terms used in this specification will be explained.

The lower alkyl group means a $C_{1-6}$ linear or branched alkyl group, which may, for example, be a methyl group, an ethyl group, a propyl group, an isopropyl group, a butyl group, a sec-butyl group, a tert-butyl group, a pentyl group or a hexyl group. Among them, a methyl group or an ethyl group is preferred.

The halogen atom may be a fluorine atom, a chlorine atom, a bromine atom or an iodine atom. For example, a fluorine atom or a chlorine atom is preferred.

The lower alkoxy group means a $C_{1-6}$ alkoxy group or alkylenedioxy group, which may, for example, be a methoxy group, an ethoxy group, a propoxy group, a butoxy group, a tert-butoxy group, a methylenedioxy group or an ethylenedioxy group. Among them, a methoxy group, an ethoxy group or a methylenedioxy group is preferred.

The aryl group means a phenyl group, a naphthyl group or an anthryl group. A phenyl group or a naphthyl group is preferred.

The heteroaromatic ring group means a 5-membered or 6-membered monocyclic aromatic heterocyclic group containing one or two heteroatoms, which are the same or different, selected from the group consisting of an oxygen atom, a nitrogen atom and a sulfur atom, or a fused aromatic heterocyclic group having such a monocyclic aromatic heterocyclic group fused with the above-mentioned aryl group or having the same or different such monocyclic aromatic heterocyclic groups fused with each other, which may, for example, be a pyrrolyl group, an imidazolyl group, a pyrazolyl group, a pyridyl group, a pyrazinyl group, a pyrimidinyl group, a pyridazinyl group, an oxazolyl group, an isoxazolyl group, a furyl group, a thienyl group, a thiazolyl group, an isothiazolyl group, an indolyl group, a benzofuranyl group, a benzothienyl group, a benzimidazolyl group, a benzoxazolyl group, a benzisoxazolyl group, a benzothiazolyl group, a benzisothiazolyl group, an indazolyl group, a purinyl group, a quinolyl group, an isoquinolyl group, a phthalazinyl group, a naphthylidinyl group, a quinoxalinyl group, a quinazolinyl group, a cinnolinyl group or a pteridinyl group. Among them, a furyl group, a thienyl group, a pyridyl group, an oxazolyl group, a thiazolyl group, a benzofuranyl group, a benzothienyl group, a benzoxazolyl group, a benzothiazolyl group or a quinolyl group is preferred.

The lower alkenyl group means a $C_{3-6}$ linear or branched alkenyl group, which may, for example, be an allyl group, a 2-butenyl group, a 3-butenyl group, a 3-methyl-2-butenyl group, a 2-pentenyl group or a 2-hexenyl group. Among them, an allyl group or a 2-butenyl group is preferred.

The lower alkynyl group means a $C_{3-6}$ linear or branched alkynyl group, which may, for example, be a propargyl group, a 2-butynyl group, a 3-butynyl group, a 2-pentynyl group or a 4-methyl-2-pentynyl group. Among them, a propargyl group or a 2-butynyl group is preferred.

The aralkyl group means the above-mentioned lower alkyl group or lower alkenyl group, preferably lower alkyl group, which has the above-mentioned aryl group which may be substituted by the above-mentioned halogen atom, lower alkyl group or lower alkoxy group, which may, for example, be a benzyl group, a phenethyl group, a 3-phenylpropyl group, a 4-chlorobenzyl group, a 3-chlorobenzyl group, a 3,4-dimethylbenzyl group, a 4-chlorophenethyl group, a 1-naphthylmethyl group, a 2-naphthylmethyl group, a 1-(2-naphthyl)ethyl group, a 3-(4-chlorophenyl)-propyl group, a 3-phenyl-2-propenyl group or a 3-(4-chlorophenyl)-2-propenyl group. Among them, a benzyl group, a phenethyl group, a 4-chlorobenzyl group, a 3,4-dimethylbenzyl group, a 2-naphthylmethyl group, a 1-(2-naphthyl)ethyl group or a 3-phenyl-2-propenyl group is preferred. Particularly preferred is a benzyl group, a 2-naphthylmethyl group or a 1-(2-naphthyl)ethyl group.

The saturated aliphatic hydrocarbon group may, for example, be a trimethylene group, a tetramethylene group, a pentamethylene group, a hexamethylene group, a heptamethylene group or an octamethylene group. For example, a trimethylene group, a tetramethylene group or a pentamethylene group is preferred.

The unsaturated aliphatic hydrocarbon group means an unsaturated aliphatic hydrocarbon group having at least one, preferably one or two double bonds, at optional positions on the carbon chain, which may, for example, be a propenylene group, a 1-butenylene group, a 2-butenylene group, a 1,3-butadienylene group, a 1-pentenylene group, a 2-pentenylene group, a 1,3-pentadienylene group, a 1,4-pentadienylene group, a 1-hexenylene group, a 2-hexenylene group, a 3-hexenylene group, a 1,3-hexadienylene group, a 1,4-hexadienylene group, a 1,5-hexadienylene group, a 1,3,5-hexatrienylene group, a 1-heptenylene group, a 2-heptenylene group, a 3-heptenylene group, a 1,3-heptadienylene group, a 1,4-heptadienylene group, a 1,5-heptadienylene group, a 1,6-heptadienylene group, a 1,3,5-heptatrienylene group, a 1-octenylene group, a 2-octenylene group, a 3-octenylene group, a 4-octenylene group, a 1,3-octadienylene group, a 1,4-octadienylene group, a 1,5-octadienylene group, a 1,6-octadienylene group, a 1,7-octadienylene group, a 2,4-octadienylene group, a 2,5-octadienylene group, a 2,6-octadienylene group, a 3,5-octadienylene group, a 1,3,5-octatrienylene group, a 2,4,6-octatrienylene group or a 1,3,5,7-octatetraenylene group. Among them, a propenylene group, a 1-butenylene group, a 1,3-butadientylene group or a 1-pentenylene group is preferred.

The salt of the compound of the formula (I) means a pharmaceutically acceptable common salt, which may, for example, be a base-addition salt of the terminal carboxyl group or a carboxyl group when such a carboxyl group is present on the saturated or unsaturated aliphatic hydrocarbon group represented by A in the formula (I), or an acid-addition salt of a basic heteroaromatic ring when such a basic heteroaromatic ring is present.

The base-addition salt may, for example, be an alkali metal salt such as a sodium salt or a potassium salt; an alkaline earth metal salt such as a calcium salt or a magnesium salt; an ammonium salt; or an organic amine salt such as a trimethylamine salt, a triethylamine salt, a dicyclohexylamine salt, an ethanolamine salt, a diethanolamine salt, a triethanolamine salt, a procaine salt or an N,N'-dibenzylethylenediamine salt.

The acid-addition salt may, for example, be an inorganic acid salt such as a hydrochloride, a sulfate, a nitrate, a phosphate or a perchlorate; an organic acid salt such as a maleate, a fumarate, a tartrate, a citrate, an ascorbate or a trifluoroacetate; or a sulfonic acid salt such as a methanesulfonate, an isethionate, a benzenesulfonate or a p-toluenesulfonate.

The ester of the compound of the formula (I) means a pharmaceutically acceptable common ester of the terminal carboxyl group or of a carboxyl group when such a carboxyl group is present on the saturated or unsaturated aliphatic hydrocarbon group represented by A in the formula (I), which may, for example, be an ester with a lower alkyl group such as a methyl group, an ethyl group, a propyl group, an isopropyl group, a butyl group, a sec-butyl group or a tert-butyl group, an ester with a lower alkenyl group such as an allyl group or a 2-butenyl group, an ester with a lower alkanoyloxy lower alkyl group such as an acetoxymethyl group, a pivaloyloxymethyl group or a 1-pivaloyloxyethyl group, an ester with a lower alkoxycarbonyloxy lower alkyl group such as a 1-(ethoxycarbonyloxy)ethyl group or a 1-(cyclohexyloxycarbonyloxy)ethyl group, an ester with a carbamoyloxy lower alkyl group such as a carbamoyloxymethyl group, an ester with a phthalidyl group, or an ester with a (5-substituted-2-oxo-1,3-dioxol-4-yl)methyl group such as a (5-methyl-2-oxo-1,3-dioxol-4-yl)methyl group.

Further, when a hydroxyl group is present at the γ- or δ-position of the terminal carboxyl group or a carboxyl group when such a carboxyl group is present on the saturated or unsaturated aliphatic hydrocarbon group represented by A in the formula (I), such a hydroxyl group and a carboxyl group may form an intramolecular ester i.e. a 5-membered or 6-membered lactone ring.

The hydroxyl-protecting group may, for example, be a lower alkylsilyl group such as a trimethylsilyl group or a tert-butyldimethylsilyl group; a lower alkoxymethyl group such as a methoxymethyl group or a 2-methoxyethoxymethyl group; a tetrahydropyranyl group; an aralkyl group such as a benzyl group, a p-methoxybenzyl group, a 2,3-dimethoxybenzyl group, an o-nitrobenzyl group, a p-nitrobenzyl group or a trityl group; or an acyl group such as a formyl group or an acetyl group. Particularly preferred is a methoxymethyl group, a tetrahydropyranyl group, a trityl group, a tert-butyldimethylsilyl group or an acetyl group.

The carboxyl-protecting group may, for example, be a lower alkyl group such as a methyl group, an ethyl group, a propyl group, an isopropyl group or a tert-butyl group; a halo-substituted lower alkyl group such as a 2,2,2-trichloroethyl group or a 2,2,2-trifluoroethyl group; a lower alkanoyloxyalkyl group such as an acetoxymethyl group, a propionyloxymethyl group, a pivaloyloxymethyl group, a 1-acetoxyethyl group or a 1-pivaloyloxyethyl group; a lower alkoxycarbonyloxyalkyl group such as a 1-(methoxycarbonyloxy)ethyl group, a 1-(ethoxycarbonyloxy)ethyl group or a 1-(isopropoxycarbonyloxy)ethyl group; a lower alkenyl group such as a 2-propenyl group, a 2-chloro-2-propenyl group, a 3-methoxycarbonyl-2-propenyl group, a 2-methyl-2-propenyl group, a 2-butenyl group or a cinnamyl group; an aralkyl group such as a benzyl group, a p-methoxybenzyl group, a 3,4-dimethoxybenzyl group, an o-nitrobenzyl group, a p-nitrobenzyl group, a benzhydryl group, a bis(p-methoxyphenyl)methyl group or a trityl group; a (5-substituted-2-oxo-1,3-dioxol-4-yl)methyl group such as a (5-methyl-2-oxo-1,3-dioxol-4-yl)methyl group; a lower alkylsilyl group such as a trimethylsilyl group or a tert-butyldimethylsilyl group; an indanyl group; a phthalidyl group; or a methoxymethyl group. Particularly preferred is a methyl group, an ethyl group, a tert-butyl group, a 2-propenyl group, a benzyl group, a p-methoxybenzyl group, a benzhydryl group or a trityl group.

The compound of the formula (I) includes a compound of the formula (I-1):

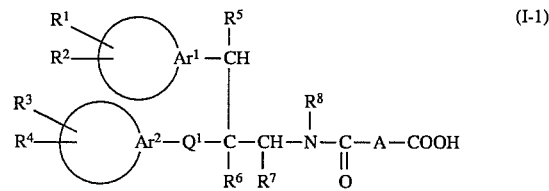

wherein each of

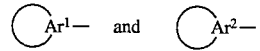

which are the same or different, is an aryl group or a heteroaromatic ring group; A is a $C_{3-8}$ linear saturated or unsaturated aliphatic hydrocarbon group which may have substituent(s) selected from the group consisting of a lower alkyl group, a hydroxyl group, a lower alkoxy group, a carboxyl group, an aryl group and an aralkyl group; $Q^1$ is a single bond; each of $R^1$, $R^2$, $R^3$ and $R^4$ which are the same or different, is a hydrogen atom, a halogen atom, a lower alkyl group, a hydroxyl group, a lower alkoxy group, or an aryl or heteroaromatic ring group which may have substituent(s) selected from the group consisting of a halogen atom, a lower alkyl group and a lower alkoxy group; each of $R^5$, $R^6$ and $R^7$ which are the same or different, is a hydrogen atom or a lower alkyl group; and $R^8$ is a hydrogen atom, a lower alkyl group, a lower alkenyl group, a lower alkynyl group or an aralkyl group, provided that

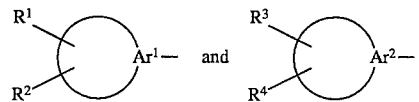

are not simultaneously 4-chlorophenyl groups, and a compound of the formula (I-2):

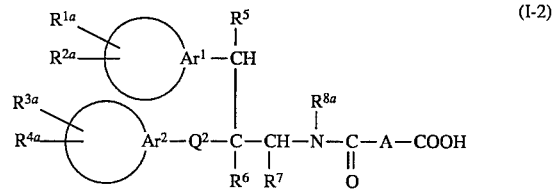

wherein each of

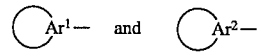

which are the same or different, is an aryl group or a heteroaromatic ring group; A is a $C_{3-8}$ linear saturated or unsaturated aliphatic hydrocarbon group which may have substituent(s) selected from the group consisting of a lower alkyl group, a hydroxyl group, a lower alkoxy group, a carboxyl group, an aryl group and an aralkyl group; $Q^2$ is a group of the formula —CO—O—, —O—CO—, —CH$_2$CH$_2$—, —CH=CH—, —OCH$_2$—, —SCH$_2$—, —CH$_2$O— or —CH$_2$S—; each of $R^{1a}$, $R^{2a}$, $R^{3a}$ and $R^{4a}$ which are the same or different, is a hydrogen atom, a halogen atom, a lower alkyl group, a hydroxyl group or a lower alkoxy group; and each of $R^5$, $R^6$, $R^7$ and $R^{8a}$ which are the same or different, is a hydrogen atom or a lower alkyl group.

Among the compounds of the formula (I), particularly preferred is a compound of the formula (I-a):

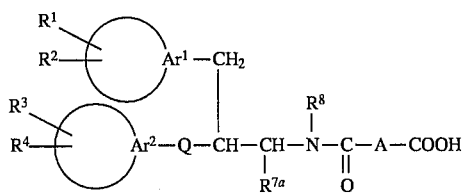

wherein each of

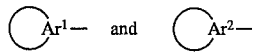

which are the same or different, is an aryl group or a heteroaromatic ring group; A is a $C_{3-8}$ linear saturated or unsaturated aliphatic hydrocarbon group which may have substituent(s) selected from the group consisting of a lower alkyl group, a hydroxyl group, a lower alkoxy group, a carboxyl group, an aryl group and an aralkyl group; Q is a single bond or a group of the formula —CO—O—, —O—CO—, —CH$_2$CH$_2$—, —CH═CH—, —OCH$_2$—, —SCH$_2$—, —CH$_2$O— or —CH$_2$S—; each of $R^1$, $R^2$, $R^3$ and $R^4$ which are the same or different, is a hydrogen atom, a halogen atom, a lower alkyl group, a hydroxyl group, a lower alkoxy group, or an aryl or heteroaromatic ring group which may have substituent(s) selected from the group consisting of a halogen atom, a lower alkyl group and a lower alkoxy group; $R^{7a}$ is a lower alkyl group; and $R^8$ is a hydrogen atom, a lower alkyl group, a lower alkenyl group, a lower alkynyl group or an aralkyl group, provided that when Q is a single bond,

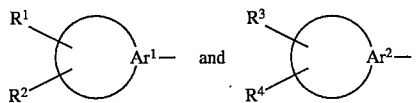

are not simultaneously 4-chlorophenyl groups.

Further, the compound of the formula (I) of the present invention may have stereoisomers such as optical isomers, diastereomers or geometrical isomers, depending upon the form of its substituents. The compound of the formula (I) of the present invention includes all of such stereoisomers and their mixtures. Among them, a compound with a steric configuration of the formula (I-a$^1$):

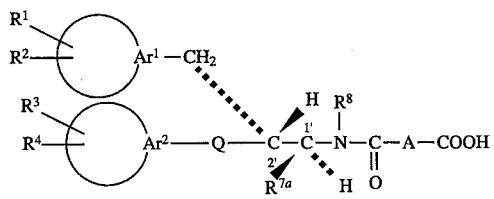

wherein

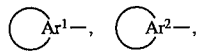

A, Q, $R^1$, $R^2$, $R^3$, $R^4$, $R^{7a}$ and $R^8$ are as defined above, or a compound with a steric configuration of the formula (I-a$^2$):

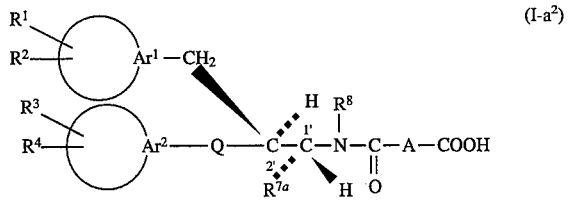

wherein

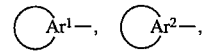

A, Q, $R^1$, $R^2$, $R^3$, $R^4$, $R^{7a}$ and $R^8$ are as defined above, is preferred. Namely, preferred is a compound in which the steric configuration on the carbon atoms at the 1'-position and 2'-position is a (1'S, 2'S) configuration or a (1'R, 2'R) configuration when Q is a single bond or a group of the formula —CH$_2$CH$_2$— or —CH═CH—, or a (1'S, 2'R) configuration or a (1'R, 2'S) configuration when Q is a group of the formula —CO—O—, —O—CO—, —OCH$_2$—, —SCH$_2$—, —CH$_2$O— or —CH$_2$S—. Particularly preferred is a compound of the formula (I-a$^1$) i.e. a compound wherein the steric configuration on the carbon atoms at the 1'-position and 2'-position are a (1'S, 2'S) configuration when Q is a single bond or —CH$_2$CH$_2$— or —CH═CH—, or a (1'S, 2'R) configuration when Q is —CO—O—, —O—CO—, —OCH$_2$—, —SCH$_2$—, —CH$_2$O— or —CH$_2$S—. Here, the 1'-position and 2'-position are the positions indicated in the above formulas (I-a$^1$) and (I-a$^2$).

When Q is a group of the formula —CH═CH—, there exist E-isomer (trans isomer) and Z-isomer (cis isomer) as geometrical isomers based on the group. Preferred is E-isomer.

The $C_{3-8}$ linear saturated or unsaturated aliphatic hydrocarbon group which may have substituent(s) selected from the group consisting of a lower alkyl group, a hydroxyl group, a lower alkoxy group, a carboxyl group, an aryl group and an aralkyl group, for A, means the above-mentioned saturated aliphatic hydrocarbon group or the above-mentioned unsaturated aliphatic hydrocarbon group, which is unsubstituted or which may have substituent(s) at an optical position for substitution, and such substituent may be at least one, preferably one or two members, which are the same or different, selected from the group consisting of a lower alkyl group, a hydroxyl group, a lower alkoxy group, a carboxyl group, an aryl group and an aralkyl group.

Q means a single bond or a group of the formula —CO—O—, —O—CO—, —CH$_2$CH$_2$—, —CH═CH—, —OCH$_2$—, —SCH$_2$—, —CH$_2$O— or —CH$_2$S—. Among them, a single bond or a group of the formula —CO—O—, —CH$_2$CH$_2$—, —CH═CH—, —OCH$_2$—, —SCH$_2$— or —CH$_2$O— is preferred.

More preferred is a compound of the formula (I-b):

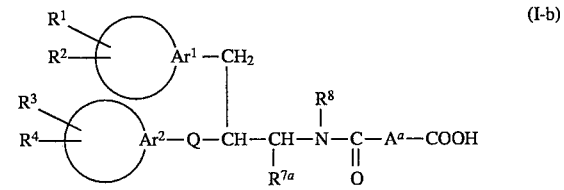

wherein each of

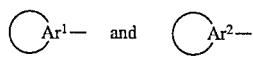

which are the same or different, is an aryl group or a heteroaromatic ring group; $A^a$ is a group of the formula —$(CH_2)_m$—$C(R^9)(R^{10})$—$(CH_2)_n$— (wherein $R^9$ is a hydrogen atom, a lower alkyl group, a hydroxyl group or a lower alkoxy group; $R^{10}$ is a hydrogen atom, a lower alkyl group, an aryl group, an aralkyl group or a carboxyl group; m is an integer of from 1 to 3; and n is an integer of from 1 to 4) or a group of the formula —$(CH_2)_q$—CH=CH— (wherein q is an integer of from 1 to 6); Q is a single bond or a group of the formula —CO—O—, —O—CO—, —$CH_2CH_2$—, —CH=CH—, —$OCH_2$—, —$SCH_2$—, —$CH_2O$— or —$CH_2S$—; each of $R^1$, $R^2$, $R^3$ and $R^4$ which are the same or different, is a hydrogen atom, a halogen atom, a lower alkyl group, a hydroxyl group, a lower alkoxy group, or an aryl or heteroaromatic ring group which may have substituent(s) selected from the group consisting of a halogen atom, a lower alkyl group and a lower alkoxy group; $R^{7a}$ is a lower alkyl group; and $R^8$ is a hydrogen atom, a lower alkyl group, a lower alkenyl group, a lower alkynyl group or an aralkyl group, provided that when Q is a single bond,

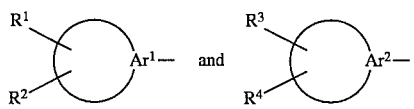

are not simultaneously 4-chlorophenyl groups.

$R^9$ is preferably a hydrogen atom or a hydroxyl group. Particularly preferred is a hydrogen atom.

$R^{10}$ is preferably a lower alkyl group, a lower alkoxy group or a carboxyl group. Particularly preferred is a methyl group, an ethyl group, a propyl group, a methoxy group, an ethoxy group or a carboxyl group.

Each of m and n which are the same or different, is preferably 1 or 2, and q is preferably 1 or 2.

In the formula (I),

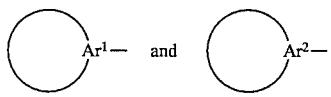

which are the same or different, is an aryl group or a heteroaromatic ring group; each of $R^1$, $R^2$, $R^3$ and $R^4$ which are the same or different, is a hydrogen atom, a halogen atom, a lower alkyl group, a hydroxyl group, a lower alkoxy group, or an aryl or heteroaromatic ring group which may have substituent(s) selected from the group consisting of a halogen atom, a lower alkyl group and a lower alkoxy group, provided that when Q is a single bond,

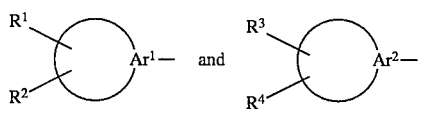

are not simultaneously 4-chlorophenyl groups.

In the formula (I), $R^1$ and $R^2$ which are the same or different, may substitute at optional positions for substitution on the aryl or heteroaromatic ring group of the formula

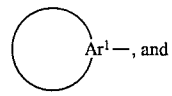

$R^3$ and $R^4$ which are the same or different, may substitute at optional positions for substitution on the aryl or heteroaromatic ring group of the formula

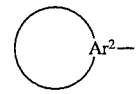

The aryl or heteroaromatic ring group which may have substituent(s) selected from the group consisting of a halogen atom, a lower alkyl group and a lower alkoxy group, for $R^1$, $R^2$, $R^3$, $R^4$, means the above-mentioned aryl or heteroaromatic ring group, which is unsubstituted or which has a substituent at an optional position for substitution, and the substituent is one or more members, preferably one or two members, which are the same or different, selected from the group consisting of a halogen atom, a lower alkyl group and a lower alkoxy group. Among them, preferred is an unsubstituted phenyl group, a naphthyl group, or a heteroaromatic ring group such as a pyridyl group, an oxazolyl group or a thienyl group; a halogenated phenyl group such as a chlorophenyl group, a bromophenyl group or a fluorophenyl group; a lower alkylphenyl group such as a methylphenyl group, an ethylphenyl group, a propylphenyl group or a tert-butylphenyl group; or a lower alkoxyphenyl group such as a methoxyphenyl group, an ethoxyphenyl group, a tert-butoxyphenyl group or a methylenedioxyphenyl group. Particularly preferred is a phenyl group, a naphthyl group, a pyridyl group, an oxazolyl group, a thienyl group, a chlorophenyl group, a fluorophenyl group, a methylphenyl group, a methoxyphenyl group or a methylenedioxyphenyl group.

Further, among compounds of the formula (I), preferred is a compound wherein the group of the formula

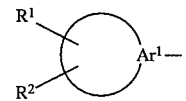

is a group of the formula

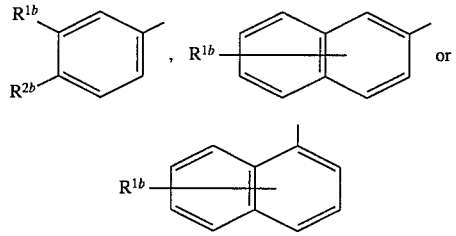

wherein each of $R^{1b}$ and $R^{2b}$ which are the same or different, is a hydrogen atom, a halogen atom, a lower alkyl group, a lower alkoxy group, or an aryl or heteroaromatic ring group which may have substituent(s) selected from the group consisting of a halogen atom, a lower alkyl group and a lower alkoxy group, such as a phenyl group, a 3-chlorophenyl group, a 4-chlorophenyl group, a 4-fluorophenyl group, 4-methylphenyl group, a 3,4-dichlorophenyl group, a 4-methoxyphenyl group, a 3-bromophenyl group, a 3-biphenylyl group, a 4-biphenylyl group, a 4'-chloro-4-biphenylyl group, a 2-fluoro-4-biphenylyl group, a 6-fluoro-3-biphenylyl group, a 3-(2naphthyl)phenyl group, a 3-(1-naphthyl)phenyl group, a 4-(2-naphthyl)phenyl group, a 1-naphthyl group or a 2-naphthyl group. More preferred is a compound wherein said group is a group of the formula

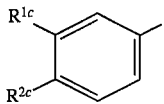

(wherein each of $R^{1c}$ and $R^{2c}$ which are the same or different, is a hydrogen atom, a halogen atom, a lower alkyl group or a lower alkoxy group) or a naphthyl group, such as a phenyl group, a 3-chlorophenyl group, a 4-chlorophenyl group, a 4-fluorophenyl group, a 4-methylphenyl group, a 3,4-dichlorophenyl group, a 4-methoxyphenyl group, a 3-bromophenyl group, a 1-naphthyl group or a 2-naphthyl group. Particularly preferred is a compound wherein the said group is a 3,4-dichlorophenyl group, a 4-chlorophenyl group, a 1-naphthyl group or a 2-naphthyl group.

Among compounds of the formula (I), preferred is a compound wherein the group of the formula

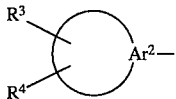

is a group of the formula

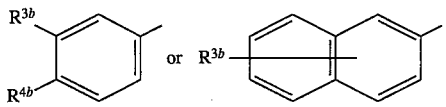

wherein $R^{3b}$ is a hydrogen atom, a halogen atom, a lower alkyl group or a lower alkoxy group; and $R^{4b}$ is a hydrogen atom, a halogen atom, a lower alkyl group, a lower alkoxy group, or an aryl or heteroaromatic ring group which may have substituent(s) selected from the group consisting of a halogen atom, a lower alkyl group and a lower alkoxy group, particularly such as a 4-biphenylyl group, a phenyl group, a 4-chlorophenyl group, a 4-methylphenyl group, a 4-bromophenyl group, a 4-tert-butylphenyl group, a 4-methoxyphenyl group, a 3-chlorophenyl group, a 2-naphthyl group, a 4'-chloro-4-biphenylyl group, a 4-(3-thienyl)phenyl group, a 4-(3-pyridyl)phenyl group, a 3'-chloro-4-biphenylyl group, a 3,4-dichlorophenyl group, a 3,4-difluorophenyl group, a 3,4-dimethylphenyl group, a 3-chloro-4-methylphenyl group, a 4-chloro-3-methylphenyl group, a 3,4-dimethoxyphenyl group, a 3,4-methylenedioxyphenyl group, a 3-bromophenyl group, a 4-(2-naphthyl)phenyl group, a 2-fluoro-4-biphenylyl group, a 4-(2-furyl)phenyl group, a 3',4'-methylenedioxy-4-biphenylyl group, a 2'-fluoro-4-biphenylyl group, a 2'-methoxy-4-biphenylyl group or a 4-(5-oxazolyl)phenyl group is preferred. When Q is a single bond, said group is preferably a 4-biphenylyl group, a 2-naphthyl group, a 4'-chloro-4-biphenylyl group, a 4-(3-thienyl)phenyl group, a 4-(3-pyridyl)phenyl group, a 3'-chloro-4-biphenylyl group, a 3,4-dichlorophenyl group, a 4-(2-naphthyl)phenyl group, a 2-fluoro-4-biphenylyl group, a 4-(2-furyl)phenyl group, a 3',4'-methylenedioxy-4-biphenylyl group, a 2'-fluoro-4-biphenylyl group, a 2'-methoxy-4-biphenylyl group or a 4-(5-oxazolyl)phenyl group.

Further, among compounds of the formula (I), preferred is a compound wherein when Q is a group of the formula —CO—O—, —O—CO—, —CH$_2$CH$_2$—, —CH=CH—, —OCH$_2$—, —SCH$_2$—, —CH$_2$O— or —CH$_2$S—, the group of the formula

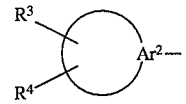

is a group of the formula

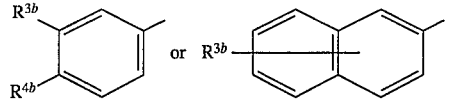

wherein each of $R^{3b}$ and $R^{4c}$ which are the same or different, is a hydrogen atom, a halogen atom, a lower alkyl group or a lower alkoxy group. Particularly preferred is the compound wherein said group is a 2-naphthyl group, a 3,4-difluorophenyl group, a 3,4-dichlorophenyl group, a 3,4-dimethylphenyl group, a 3-chloro-4-methylphenyl group, a 4-chloro-3-methylphenyl group, a 3,4-dimethoxyphenyl group or a 3,4-methylenedioxyphenyl group.

$R^{1b}$ and $R^{3b}$ on the naphthyl groups may substitute at optional positions for substitution on the respective naphthyl groups.

Further, in the formula (I), each of $R^5$, $R^6$ and $R^7$ which are the same or different, is a hydrogen atom or a lower alkyl group; and $R^8$ is a hydrogen atom, a lower alkyl group, a lower alkenyl group, a lower alkynyl group or an aralkyl group.

Preferred as $R^5$ and $R^6$ is a hydrogen atom, a methyl group or an ethyl group. Particularly preferred is a hydrogen atom.

As $R^7$, a lower alkyl group is preferred, and a methyl group, an ethyl group or a propyl group is more preferred. Particularly preferred is a methyl group.

As $R^8$, a hydrogen atom, a lower alkyl group or an aralkyl group is preferred, and a hydrogen atom, a methyl group, an ethyl group, a propyl group, a benzyl group, a 3,4-dimethylbenzyl group, 4-chlorobenzyl group, a 3,4-dichlorobenzyl group, a 1-naphthylmethyl group, a 2-naphthylmethyl group or a 1-(2-naphthyl)ethyl group is more preferred. Particularly preferred is a hydrogen atom, a methyl group, an ethyl group, a benzyl group, a 2-naphthylmethyl group or a 1-(2-naphthyl)ethyl group.

Particularly preferred as $R^8$ is a hydrogen atom or a lower alkyl group. When Q is a single bond, $R^8$ is preferably an aralkyl group in addition to a hydrogen atom or a lower alkyl group.

Now, a process for producing the compound of the present invention will be described.

The compound of the formula (I) of the present invention can be prepared, for example, by the following process.

Namely, the compound of the formula (I) can be prepared by a process which comprises reacting a compound of the formula (II):

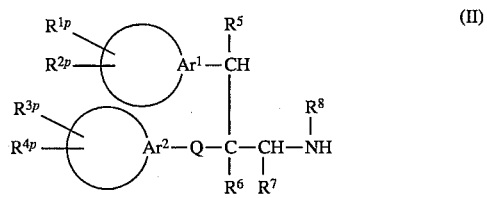

wherein

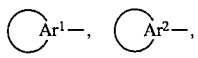

Q, $R^5$, $R^6$, $R^7$ and $R^8$ are as defined above; and each of $R^{1p}$, $R^{2p}$, $R^{3p}$ and $R^{4p}$ which are the same or different, is a hydrogen atom, a halogen atom, a lower alkyl group, a hydroxyl group which may be protected, a lower alkoxy group, or an aryl or heteroaromatic ring group which may have substituent(s) selected from the group consisting of a halogen atom, a lower alkyl group and a lower alkoxy group, provided that when Q is a single bond,

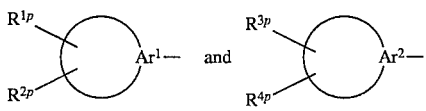

are not simultaneously 4-chlorophenyl groups, with a carboxylic acid of the formula (III) or its reactive derivative:

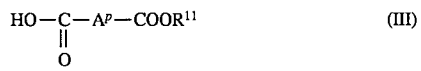

wherein $A^p$ is a $C_{3-8}$ linear saturated or unsaturated aliphatic hydrocarbon group which may have substituent(s) selected from the group consisting of a lower alkyl group, a lower alkoxy group, an aryl group, an aralkyl group, and a hydroxyl and carboxyl group which may be protected; and $R^{11}$ is a hydrogen atom or a carboxyl-protecting group, to form a compound of the formula (IV):

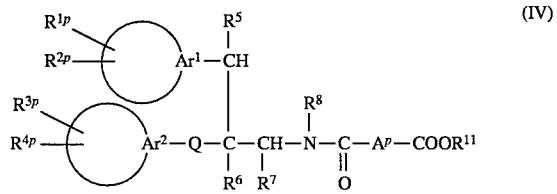

wherein

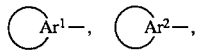

$A^p$, Q, $R^{1p}$, $R^{2p}$, $R^{3p}$, $R^{4p}$, $R^5$, $R^6$, $R^7$, $R^8$ and $R^{11}$ are as defined above, and if necessary, removing any protecting group.

As the reactive derivative of the carboxylic acid of the formula (III), an acid halide, a mixed acid anhydride, an active ester or an active amide may, for example, be used.

When the carboxylic acid of the formula (III) is used, it is preferred to conduct the reaction in the presence of a condensing agent such as N,N'-dicyclohexyl carbodiimide or 1-ethyl-3-(3-dimethylaminopropyl)carbodiimide.

The reaction of the compound of the formula (II) with the carboxylic acid of the formula (III) or its reactive derivative, is conducted usually by using 1 mol or an excess molar amount, preferably from 1 to 5 mols, of the carboxylic acid of the formula (III) or its reactive derivative, per mol of the compound of the formula (II).

The reaction is conducted usually in an inert solvent. The inert solvent may, for example, be a halogenated hydrocarbon such as methylene chloride, chloroform, carbon tetrachloride, dichloroethane or trichloroethylene; an ether such as ethyl ether, tetrahydrofuran or dioxane; an aromatic hydrocarbon such as benzene, toluene, chlorobenzene or xylene; an aprotic polar solvent such as dimethylformamide, acetonitrile, acetone, ethyl acetate or hexamethylphosphoric triamide, or a mixture of such solvents.

The reaction temperature is usually from −70° C. to the boiling point of the solvent used for the reaction, preferably from −20° C. to 100° C.

The reaction time is usually from 5 minutes to 7 days, preferably from 10 minutes to 24 hours.

The above reaction can be conducted in the presence of a base to facilitate the reaction. Especially when an acid halide or a mixed acid anhydride is used as the reactive derivative of the carboxylic acid of the formula (III), it is preferred to conduct the reaction in the presence of an inorganic base such as sodium hydroxide, potassium hydroxide, calcium hydroxide, sodium carbonate, potassium carbonate or sodium hydrogencarbonate, or an organic base such as triethylamine, N-ethyldiisopropylamine, pyridine, 4-dimethylaminopyridine or N,N-dimethylaniline.

Such a base is used usually in an amount of 1 mol or an excess molar amount, preferably from 1 to 5 mols, per mol of the reactive derivative of the carboxylic acid of the formula (III).

The acid halide of the compound of the formula (III) can be obtained by reacting the carboxylic acid of the formula (III) with a halogenating agent in accordance with a conventional method. As the halogenating agent, thionyl chloride, phosphorus trichloride, phosphorus pentachloride, phosphorus oxychloride, phosphorus tribromide, oxalyl chloride or phosgene may, for example, be used.

The mixed acid anhydride of the compound of the formula (III) can be obtained by reacting the carboxylic acid of the formula (III) with an alkyl chlorocarbonate such as ethyl chlorocarbonate or with an aliphatic carboxylic acid chloride such as acetyl chloride, in accordance with a conventional method. Further, an intramolecular acid anhydride may be formed between carboxyl groups at both terminals, or when in the formula (III), a carboxyl group is present on the saturated or unsaturated aliphatic hydrocarbon group for $A^p$, an intramolecular acid anhydride may be formed between such a carboxyl group and a carboxyl group to be involved in the reaction, to constitute a reactive derivative of the carboxylic acid.

The active ester of the compound of the formula (III) can be prepared by reacting the carboxylic acid of the formula (III) with an N-hydroxy compound such as N-hydroxysuccinimide, N-hydroxyphthalimide or 1-hydroxybenzotriazole, or a phenol compound such as a 4-nitrophenol, 2,4-dinitrophenoi, 2,4,5-trichlorophenol or pentachlorophenol, in the presence of a condensing agent such as N,N'-dicyclohexylcarbodiimide or 1-ethyl-3-(3-dimethylaminopropyl)carbodiimide in accordance with a conventional method.

The active amide of the compound of the formula (III) can be prepared by reacting the carboxylic acid of the formula (III) with e.g. 1,1'-carbonyldiimidazole or 1,1'-carbonylbis(2-methylimidazole) in accordance with a conventional method.

When a hydroxyl group is present on the group of the formula

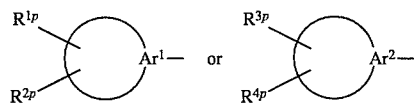

in the formula (II) or on the saturated or unsaturated aliphatic hydrocarbon group for $A^p$ in the formula (III) and when a carboxyl group is present on the compound of the formula (III), it is preferred to conduct the reaction after appropriately protecting such a hydroxyl group or a carboxyl group and remove the protecting group after the reaction.

After completion of the reaction, conventional treatment is conducted to obtain a crude product of the compound of the formula (IV). The compound of the formula (IV) may or may not be purified in accordance with a conventional method, and if necessary, reactions for removing protecting groups such as a hydroxyl group and a carboxyl group, are appropriately conducted to obtain a compound of the formula (I).

Removal of protecting groups may vary depending upon their types, but can be conducted in accordance with the methods disclosed in a literature (Protective Groups in Organic Synthesis, T. W. Greene, John Wiley & Sons (1981)) or methods similar thereto, for example by solvolysis employing an acid or a base, by chemical reduction employing a metal hydride complex or by hydrogenation employing a palladium-carbon catalyst or Raney nickel.

Isolation or purification of the compound of the formula (I) obtained by the above method may be conducted by conventional separating methods such as column chromatography employing silica gel or adsorbent resin, liquid chromatography, solvent extraction or recrystallization-re-precipitation individually or in a proper combination.

The compound of the formula (I) can be converted to a pharmaceutically acceptable salt or ester by a conventional method. Reversely, conversion of the salt or ester to the free carboxylic acid can also be conducted in accordance with a conventional method.

The compound of the formula (II) and the compound of the formula (III) may be commercially available or can be prepared in accordance with the methods disclosed in literatures (J. Med. Chem., 10, 717 (1967); ibid., 725; J. Chem. Soc. Perkin I (1978), 1636; Chem. Lett., 191 (1980); ibid., 375 (1984); J. Chem. Soc. Chem. Commun. (1984), 579; J. Am. Chem. Soc., 104, 5716 (1982)) or methods similar thereto, or in accordance with the following processes or methods disclosed in Examples and Reference Examples.

PROCESS A

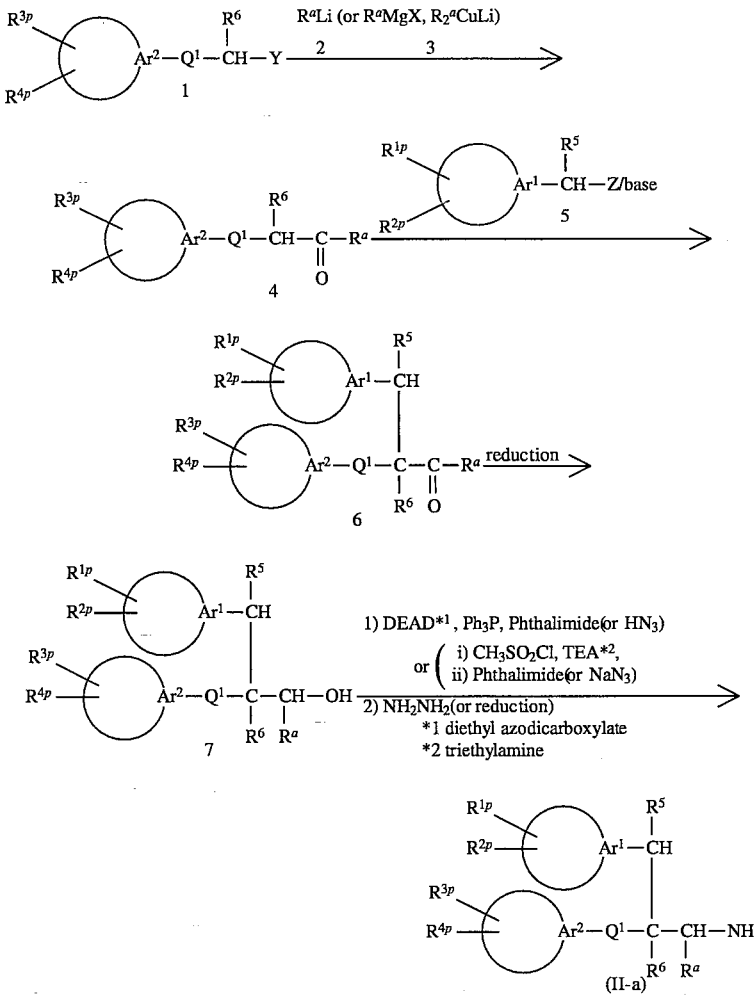

In the above formulas,

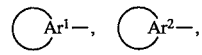

$Q^1$, $R^{1p}$, $R^{2p}$, $R^{3p}$, $R^{4p}$, $R^5$ and $R^6$ are as defined above; X is a halogen atom; Y is a cyano group, a carboxyl group, a lower alkoxycarbonyl group, a chloroformyl group or an N-methoxy-N-methylcarbamoyl group; Z is a leaving group selected from the group consisting of a chlorine atom, a bromine atom, an iodine atom, a methanesulfonyloxy group, a trifluoromethanesulfonyloxy group and a p-toluenesulfonyloxy group; and $R^a$ is a lower alkyl group.

Process A is a process for producing a compound of the formula (II-a) i.e. a starting material compound for producing a compound of the formula (I) wherein Q is a single bond and $R^7$ is a lower alkyl group.

By this process, the desired compound (II-a) can be produced by reacting firstly a nitrile or a carboxylic acid derivative of the formula 1 with an alkyl lithium of the formula 2 or an alkyl Grignard reagent (or an alkyl Gilman reagent) of the formula 3 to obtain a ketone compound 4, then reacting an alkylating agent of the formula 5 to the ketone compound 4 to produce an alkyl compound 6, then reacting a reducing agent such as a metal hydride complex to the alkyl compound 6 to produce an alcohol compound 7, then reacting to the alcohol compound 7, diethyl azodicarboxylate, triphenylphosphine and phthalimide (or hydrogen azide), or methanesulfonyl chloride and triethylamine, followed by reacting phthalimide in the presence of a base (or sodium azide) to obtain a phthalimide-protected form of an amine compound (or an azide compound) (II-a), and finally reacting thereto hydrazine (or a reducing agent) to remove the phthalimide group (or reducing the azide group).

The above reaction steps will be described in detail referring to suitable reaction conditions, etc.

The first step of synthesizing the ketone compound 4 is conducted usually by reacting 1 mol or an excess molar amount, preferably from 1 to 5 mols of the alkyl lithium 2 or the alkyl Grignard reagent (or the alkyl Gilman reagent in the case where the substituent Y of the compound 1 is a chloroformyl group) 3 to 1 mol of the starting material compound 1 in a solvent inert to the reaction such as tetrahydrofuran, ethyl ether or benzene, if necessary followed by hydrolysis under an acidic condition.

The reaction temperature is usually from −80° C. to the boiling point of the solvent used for the reaction, preferably from −70° C. to 50° C. The reaction time is usually from 5 minutes to 48 hours, preferably from 30 minutes to 24 hours.

When the substituent Y in the formula of the starting material compound 1 is a cyano group, it may be necessary to conduct a hydrolytic reaction under an acidic condition after completion of the reaction, and such a hydrolytic reaction is conducted in e.g. methanol, ethanol, tetrahydrofuran or a solvent mixture thereof with water in the presence of an acid such as hydrochloric acid, sulfuric acid or p-toluenesulfonic acid. The reaction temperature is usually from 0° C. to the boiling point of the solvent used for the reaction, and the reaction time is from 30 minutes to 24 hours.

The step of converting the ketone compound 4 obtained by the above reaction to the alkyl compound 6, can be conducted by reacting an equimolar amount or an excess molar amount, preferably from 1 to 2 mols, of the alkylating agent of the formula 5 to the ketone compound 4 in the presence of a base in an inert solvent which does not adversely affect the reaction or without using any solvent.

The inert solvent may, for example, be an ether such as ethyl ether, tetrahydrofuran or dioxane; an aromatic hydrocarbon such as benzene, toluene or xylene; an aprotic polar solvent such as dimethylformamide, dimethyl sulfoxide or hexamethylphosphoric triamide, or a mixture of such solvents.

The base to be used for this reaction, may, for example, be an alkali metal hydride such as sodium hydride, lithium hydride or potassium hydride; a lithium amide such as lithium amide, lithium diisopropylamide or lithium bis(trimethylsilyl)amide; an alkyllithium such as methyllithium, butyllithium or tert-butyllithium; an alkali metal alkoxide such as sodium methoxide, sodium ethoxide or potassium tert-butoxide; or an alkali metal hydroxide such as sodium hydroxide, potassium hydroxide or lithium hydroxide. The base is used usually in an amount of 1 mol or an excess molar amount, preferably from 1 to 5 mols, per mol of the starting material alkylating agent 5.

The reaction temperature is usually from −100° C. the boiling point of the solvent used for the reaction, preferably from −80° C. to 100° C. The reaction time is usually from 10 minutes to 48 hours, preferably from 30 minutes to 24 hours.

The reaction for reducing the compound 6 obtained by the above reaction to the alcohol compound 7 can be conducted usually by using a metal hydride complex such as sodium borohydride, diisobutylaluminum hydride, lithium aluminum hydride or by catalytic reduction lithium tri-sec-butylborohydride (L-selectride™), or employing e.g. a palladium-carbon catalyst or a Raney nickel catalyst, in an inert solvent which does not adversely affect the reaction.

When the metal hydride complex is used as the reducing agent, such a reducing agent is used usually in an amount of 1 mol or an excess molar amount, preferably from 1 to 5 mols, per mol of the starting material compound 6.

The inert solvent to be used in this reaction may be suitably selected depending upon the type of the reducing agent.

For example, when the reducing agent is sodium borohydride, an inert solvent, such as an alcohol such as methanol or ethanol; an ether such as dimethoxyethane, dioxane, tetrahydrofuran or diglyme; an aprotic polar solvent such as dimethylformamide or dimethylacetamide, or water, or a solvent mixture thereof, may be used, and particularly preferred is an alcohol such as methanol or ethanol.

For example, when the reducing agent is diisobutylaluminum hydride, an inert solvent, such as an ether such as dimethyl ether, ethyl ether, diisopropyl ether, dibutyl ether, dimethoxyethane, dioxane, tetrahydrofuran or diglyme; an aliphatic hydrocarbon such as pentane, hexane, heptane or cyclohexane; an aromatic hydrocarbon such as benzene or toluene; a halogenated hydrocarbon such as methylene chloride, or a solvent mixture thereof, may be used, and particularly preferred is toluene or methylene chloride.

For example, when the reducing agent is lithium aluminum hydride or lithium tri-sec-butylborohydride, an inert solvent, such as an ether such as dimethyl ether, ethyl ether, diisopropyl ether, dibutyl ether, dimethoxyethane, dioxane, tetrahydrofuran or diglyme; an aliphatic hydrocarbon such as pentane, hexane, heptane or cyclohexane; or an aromatic hydrocarbon such as benzene or toluene, or a solvent mixture thereof, may be used, and particularly preferred is ethyl ether or tetrahydrofuran.

For the catalytic reduction, the solvent is preferably an alcohol such as methanol or ethanol.

The reaction conditions vary depending upon the stability and the susceptibility to the reduction reaction of the starting material ketone compound 6, the type of the reducing agent and the type of the solvent. However, the reaction temperature is usually from −80° C. to 100° C., preferably from −70° C. to 40° C., and the reaction time is usually from 5 minutes to 2 days, preferably from 30 minutes to 24 hours.

For the step of producing the desired amine compound (II-a) from the alcohol compound 7, various synthetic methods and reaction conditions well known in organic synthetic chemistry for converting alcohol compounds to amines, may be employed. For example, it is possible to employ a Mitsunobu reaction using diethyl azodicarboxylate, triphenylphosphine and phthalimide (or hydrogen azide) or a method which comprises sulfonylation with a sulfonylation agent such as methanesulfonyl chloride in the presence of a base such as triethylamine, then reacting phthalimide in the presence of a base (or sodium azide), and then treating the obtained phthalimide compound with hydrazine (or reducing the azide compound).

The above reactions are conducted usually in a solvent inert to the reaction. The inert solvent may, for example, be tetrahydrofuran, dimethoxyethane, benzene or toluene in the case of the above-mentioned Mitsunobu reaction; methylene chloride, chloroform, tetrahydrofuran, benzene, ethyl acetate or dimethylformamide in the case of the sulfonylation followed by the reaction with phthalimide (or sodium azide); an alcohol such as methanol or ethanol in the next step of the phthalimide-removing reaction with hydrazine; an ether such as ethyl ether or tetrahydrofuran in the case where a metal hydride complex is used as the reducing agent in the reduction reaction of the azide compound; water-containing tetrahydrofuran in the case where phosphine reduction is conducted with triphenylphosphine or the like; and an alcohol such as methanol or ethanol in the reduction by catalytic reduction.

With respect to the amounts of the reagents to be used, in the above Mitsunobu reaction, each of diethyl azodicarboxylate, triphenylphosphine and phthalimide (or hydrogen azide) is used in an amount of 1 mol or an excess molar amount, preferably from 1 to 5 mols, per mol of the starting material alcohol compound 7. In the reaction with the phthalimide (or sodium azide) after the sulfonylation, the sulfonylation agent such as methanesulfonyl chloride is used in an amount of 1 mol or an excess molar amount, preferably from 1 to 2 mols, per mol of the alcohol compound 7, and the base such as triethylamine used at that time is usually in an amount of 1 mol or an excess molar amount, preferably from 1 to 2 mols, per mol of the sulfonylation agent. In the next step of the reaction with phthalimide in the presence of a base (or sodium azide), 1 mol or an excess molar amount, preferably from 1 to 5 mols of each of phthalimide and the base (or sodium azide) is used per mol of the starting material sulfonylation agent. Here, the base to be used together with phthalimide is preferably sodium carbonate or potassium carbonate. Otherwise, without using such a base, a sodium salt or a potassium salt of phthalimide may be used by itself. Then, in the reaction for removing the phthalimide group with hydrazine, hydrazine is used in an amount of 1 mol or an excess molar amount, preferably from 1 to 10 mols, per mol of the phthalimide compound as the starting material compound. In the reduction reaction of the azide compound with a metal hydride complex or with triphenylphosphine, the reducing agent is used usually in an amount of 1 mol or an excess molar amount, preferably from 1 to 2 mols, per mol of the azide compound as the starting material compound.

With respect to the reaction conditions, in the case of the above Mitsunobu reaction, the reaction temperature is usually from $-70°$ C. to $100°$ C., preferably from $-20°$ C. to $50°$ C., and the reaction time is usually from 5 minutes to 48 hours, preferably from 30 minutes to 24 hours. In the reaction for removing the phthalimide group by hydrazine, the reaction temperature is usually from $0°$ C. to the boiling point of the solvent used for the reaction, preferably from room temperature to $100°$ C., and the reaction time is usually from 5 minutes to 48 hours, preferably from 30 minutes to 24 hours. In the reaction for converting the azide compound to the amine compound by reduction, when a metal hydride complex is used as the reducing agent, the reaction temperature is usually from $-70°$ C. to $150°$ C. preferably from $-20°$ C. to $50°$ C., and the reaction time is usually from 5 minutes to 48 hours, preferably from 10 minutes to 10 hours. When triphenylphosphine is used as the reducing agent, the reaction temperature is usually from room temperature to the boiling point of the solvent used for the reaction, preferably from $30°$ C. to $100°$ C. and the reaction time is usually from 10 minutes to 48 hours, preferably from 30 minutes to 24 hours. Further, in the case of the reduction by catalytic reduction, the reaction temperature is usually from $0°$ C. to $100°$ C. preferably from room temperature to $50°$ C., and the reaction time is usually from 10 minutes to 48 hours, preferably from 10 minutes to 24 hours.

Further, in this process, it is also possible to react an alkylating agent of the formula 5 to the nitrile or carboxylic acid derivative of the formula 1 to preliminarily produce an alkyl compound and then to react an alkyl lithium of the formula 2 or an alkyl Grignard reagent (or an alkyl Gilman reagent) of the formula 3 to the alkyl compound to obtain a compound of the formula 6. Such a reaction can be conducted under the conditions similar to the above Process A. Accordingly, the reaction conditions described for the above Process A may be used as the reaction conditions for this reaction.

The compounds of the formulas 1 and 2 may be commercially available or can be produced by a proper combination of the methods disclosed in Examples and Reference Examples, or conventional methods or methods similar thereto.

PROCESS B

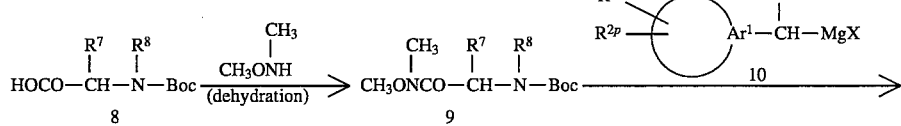

-continued
PROCESS B

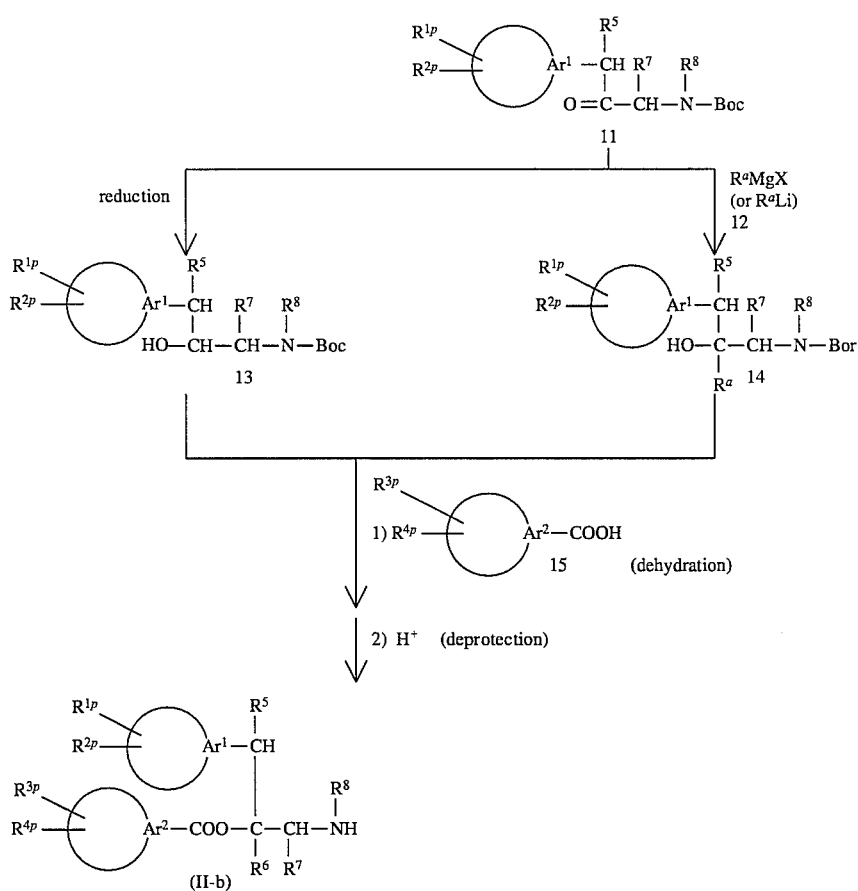

In the above formulas,

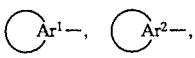

$R^{1p}$, $R^{2p}$, $R^{3p}$, $R^{4p}$, $R^5$, $R^6$, $R^7$, $R^8$, $R^a$ and X are as defined above, and Boc represents a tert-butoxycarbonyl group.

Process B is a process for producing a compound of the formula (II-b) i.e. an intermediate useful for the production of an ester derivative of the formula (I) wherein Q is a group of the formula —CO—O—.

By this process, the desired compound (II-b) can be produced by firstly reacting N,O-dimethylhydroxylamine to the carboxylic acid of the formula 8 or its reactive derivative to obtain an active amide compound 9, then reacting a Grignard reagent of the formula 10 to the amide compound to obtain a ketone compound 11, then reacting a reducing agent such as a metal hydride complex or a Grignard reagent (or an alkyl lithium) of the formula 12 to the ketone compound to obtain an alcohol compound 13 or 14, then reacting a carboxylic acid of the formula 15 or its reactive derivative to the alcohol compound 13 or 14 to obtain an ester compound, and finally removing the tert-butoxycarbonyl group as the protecting group for the amino group.

The above reaction steps will be described in detail referring to suitable reaction conditions, etc.

The first step of producing the active amide compound 9 can be conducted usually by reacting 1 mol or an excess molar amount of N,O-dimethylhydroxylamine or its hydrochloride to 1 mol of the carboxylic acid 8 or its reactive derivative, in a solvent inert to the reaction, such as tetrahydrofuran, methylene chloride or dimethylformamide. As the specific reaction conditions for this reaction, various conditions for the above-mentioned reaction of the compound of the formula (II) with the carboxylic acid of the formula (III) or its reactive derivative, may be used without change.

The step of producing the ketone compound 11 from the active amide compound 9, can be conducted usually by reacting the Grignard reagent of the formula 10 in an amount of 1 mol or an excess molar amount, preferably from 1 to 2 mols, per mol of the active amide compound 9, in a solvent inert to the reaction, such as ethyl ether, tetrahydrofuran or benzene.

The reaction temperature is usually from −80° C. to the boiling point of the solvent used for the reaction, preferably from −20° C. to 40° C. and the reaction time is usually from 5 minutes to 48 hours, preferably from 30 minutes to 10 hours.

The step of reducing the ketone compound 11 to the alcohol compound 13, can be conducted usually by using a metal hydride complex such as sodium borohydride, diisobutylaluminum hydride, lithium aluminum hydride or lithium tri-sec-butylborohydride (L-selectride™), or by catalytic reduction employing e.g. a palladium-carbon catalyst or a Raney nickel catalyst, in an inert solvent which does not adversely affect the reaction.

When the metal hydride complex is used as the reducing agent, such a reducing agent is employed usually in an amount of 1 mol or an excess molar amount, preferably from 1 to 5 mols, per mol of the starting material compound 11.

The inert solvent to be used for this reaction, may be suitably selected depending upon the type of the reducing agent.

For example, when the reducing agent is sodium borohydride, an inert solvent, such as an alcohol such as methanol or ethanol; an ether such as dimethoxyethane, dioxane, tetrahydrofuran or diglyme; or an aprotic polar solvent such as dimethylformamide or dimethylacetamide, or water, or a solvent mixture thereof, may be used. Particularly preferred is an alcohol such as methanol or ethanol.

For example, when the reducing agent is diisobutylaluminum hydride, an inert solvent, such as an ether such as dimethyl ether, ethyl ether, diisopropyl ether, dibutyl ether, dimethoxyethane, dioxane, tetrahydrofuran or diglyme; an aliphatic hydrocarbon such as pentane, hexane, heptane or cyclohexane; an aromatic hydrocarbon such as benzene or toluene; a halogenated hydrocarbon such as methylene chloride or chloroform, or a solvent mixture thereof, may be used. Particularly preferred is toluene or methylene chloride.

For example, when the reducing agent is lithium aluminum hydride or lithium tri-sec-butylborohydride, an inert solvent, such as an ether such as dimethyl ether, ethyl ether, diisopropyl ether, dibutyl ether, dimethoxyethane, dioxane, tetrahydrofuran or diglyme; an aliphatic hydrocarbon such as pentane, hexane, heptane or cyclohexane; or an aromatic hydrocarbon such as benzene or toluene, or a solvent mixture thereof, may be used. Particularly preferred is ethyl ether or tetrahydrofuran.

For the catalytic reduction, the solvent is preferably an alcohol such as methanol or ethanol.

The reaction temperature and the reaction time vary depending upon the stability and the susceptibility to the reduction reaction of the starting material ketone compound 11, the type of the reducing agent and the type of the solvent. However, the reaction temperature is usually from −80° C. to 100° C., preferably from −70° C. to 40° C. and the reaction time is usually from 5 minutes to 2 days, preferably from 30 minutes to 24 hours.

The step of producing the alcohol compound 14 from the ketone compound 11, can be conducted usually by reacting the Grignard reagent (or an alkyllithium) of the formula 12 in an amount of 1 mol or an excess molar amount, preferably from 1 to 5 mols, per mol of the ketone compound 11, in a solvent inert to the reaction, such as tetrahydrofuran, ethyl ether or benzene.

The reaction temperature is usually from −80° C. to the boiling point of the solvent used for the reaction, preferably from −70° C. to 50° C. The reaction time is usually from 5 minutes to 48 hours, preferably from 30 minutes to 24 hours.

The step of producing the compound of the formula (II-b) from the alcohol compound 13 or 14, can be conducted usually by reacting the carboxylic acid of the formula 15 or its reactive derivative in an amount of an equimolar amount or an excess molar amount to the alcohol compound 13 or 14 and then subjecting the resulting ester compound to the protecting group-removal reaction i.e. the tert-butoxycarbonyl group-removing reaction.

The first step of this reaction i.e. the step of producing the ester compound by reacting the carboxylic acid of the formula 15 or its reactive derivative to the alcohol compound 13 or 14, can be conducted under the same conditions as those for the above-mentioned reaction of the compound of the formula (II) with the carboxylic acid of the formula (III) or its reactive derivative.

The next step of the protecting group-removal reaction is conducted usually by reacting an acid such as trifluoroacetic acid, formic acid, hydrochloric acid, sulfuric acid or p-toluenesulfonic acid in the absence or presence of a solvent inert to the reaction. For example, the ester compound obtained in the above reaction is, by itself or after dissolving it in an inert solvent such as methylene chloride or anisole, reacted with an excess amount of an organic acid such as trifluoroacetic acid or formic acid usually at a temperature of from −20° C. to 100° C., preferably from 0° C. to room temperature, for 5 minutes to 48 hours, preferably from 30 minutes to 24 hours, or treated in methanol, ethanol, tetrahydrofuran or a solvent mixture thereof with water in the presence of a mineral acid or an organic acid such as hydrochloric acid, sulfuric acid or p-toluenesulfonic acid prepared to have a low concentration usually at a temperature of from 0° C. to the boiling point of the solvent used for the reaction, preferably from 0° C. to 100° C., for from 5 minutes to 48 hours, preferably from 30 minutes to 24 hours.

The compounds of the formulas 8, 10, 12 and 15 may be commercially available, or can be produced by a proper combination of the methods disclosed in Examples and Reference Examples, or conventional methods or methods similar thereto.

PROCESS C

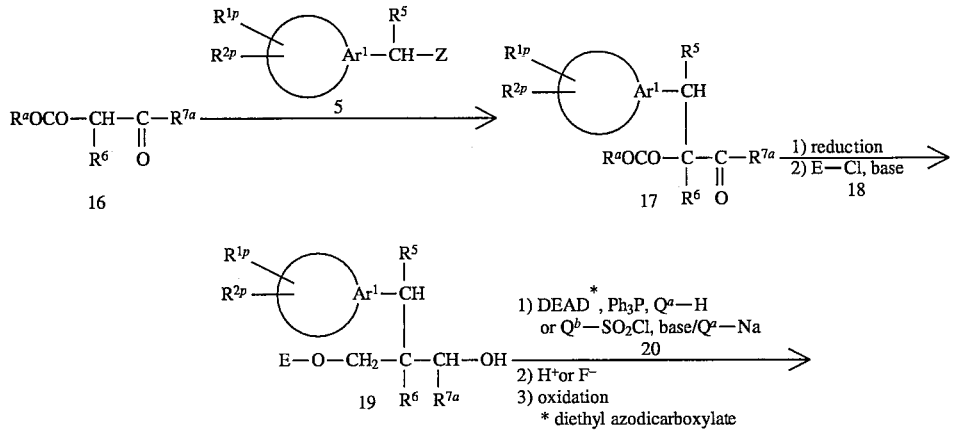

PROCESS C (-continued)

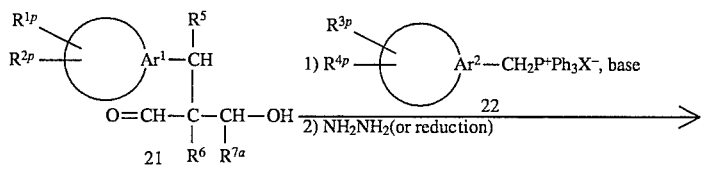

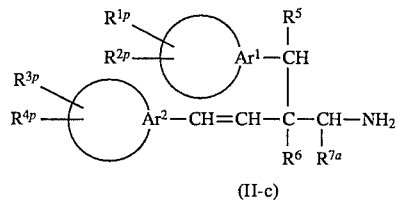

(II-c)

In the above formulas,

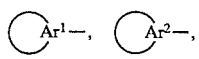

$R^{1p}$, $R^{2p}$, $R^{3p}$, $R^{4p}$, $R^5$, $R^6$, $R^{7a}$, $R^a$, X and Z are as defined above, and E is a trityl group or a tert-butyldimethylsilyl group; $Q^a$ is a phthalimide group or an azide group; and $Q^b$ is a methyl group, a phenyl group or a p-tolyl group.

Process C is a process for producing a compound of the formula (II-c) i.e. an intermediate useful for the production of a vinylene derivative of the formula (I) wherein Q is a group of the formula —CH=CH—.

According to this process, the desired compound (II-c) can be produced by firstly reacting an alkylating agent of the formula 5 to the β-ketoacid derivative of the formula 16 to obtain an alkyl compound 17, reacting a reducing agent such as a metal hydride complex to the alkyl compound 17 to obtain an alcohol, selectively protecting only a primary hydroxyl group of the resulting alcohol product to obtain a compound of the formula 19, reacting to the compound 19 diethyl azodicarboxylate, triphenylphosphine and phthalimide (or hydrogen azide), or a sulfonylation agent of the formula 20 to sulfonylate the secondary hydroxyl group, and then reacting phthalimide in the presence of a base (or sodium azide) thereto to obtain a phthalimide compound (or an azide compound), then removing the protecting group for the primary hydroxyl group, followed by oxidation to obtain the aldehyde compound 21, then reacting a Wittig reagent of the formula 22 to the aldehyde compound 21 to obtain a vinylene derivative, and then reacting hydrazine thereto to remove the phthalimide group, or to reduce the azide group.

The above reaction steps will be described in detail referring to suitable reaction conditions.

The first step of producing the alkyl compound 17 from the β-ketoacid derivative 16, can be conducted usually by reacting the alkylating agent of the formula 5 in an amount of 1 mol or an excess molar amount, preferably from 1 to 2 mols, per mol of the β-ketoacid derivative 16 in the presence of a base in an inert solvent which does not adversely affect the reaction.

Such an inert solvent may, for example, be an ether such as ethyl ether, tetrahydrofuran or dioxane; an aromatic hydrocarbon such as benzene, toluene or xylene; an aprotic polar solvent such as dimethylformamide, dimethyl sulfoxide or hexamethylphosphoric triamide, or a solvent mixture thereof.

The base to be used in this reaction, may, for example, be an alkali metal hydride such as sodium hydride, lithium hydride or potassium hydride; an alkali metal amide such as lithium amide, lithium diisopropylamide, lithium bis(trimethylsilyl)amide or sodium bis(trimethylsilyl)amide; an alkyllithium such as methyllithium, butyllithium or tert-butyllithium; or an alkali metal alkoxide such as sodium methoxide, sodium ethoxide or potassium tert-butoxide.

The base is used usually in an amount of 1 mol or an excess molar amount, preferably from 1 to 5 mols, per mol of the starting material alkylating agent.

The reaction temperature is usually from −100° C. to the boiling point of the solvent used for the reaction, preferably from −80° C. to 100° C., and the reaction time is usually from 10 minutes to 48 hours, preferably from 30 minutes to 24 hours.

In the process for producing the compound of the formula 19 from the alkyl compound 17, the reduction reaction as the first step can be accomplished by reacting a metal hydride complex such as sodium borohydride, lithium borohydride, diisobutylaluminum hydride, lithium aluminum hydride or lithium tri-sec-butylborohydride (L-selectride™) in an inert solvent which does not adversely affect the reaction. With respect to the conditions for this reduction reaction, the conditions for reducing the compound 6 with the metal hydride complex to obtain the compound 7 in the above described Process A, may be used without change. In the present reaction, it is particularly preferred that the ketone group of the compound 17 is firstly reduced with sodium borohydride or lithium tri-sec-butylborohydride, and then the ester group is reduced with lithium borohydride or lithium aluminum hydride. Also with respect to the reaction conditions of this reaction, the reduction conditions in the above described Process A can be used without change.

Then, the step of producing the compound 19 by selectively protecting only the primary hydroxyl group of the alcohol compound obtained by the above reduction reaction, can be conducted by using a trityl group or a tert-butyldimethylsilyl group as the protecting group and by reacting 1 mol or an excess molar amount, preferably from 1 to 1.5 mols, of trityl chloride or tert-butyldimethylchlorosilane, to 1 mol of the alcohol compound in the presence of a base in an inert solvent which does not adversely affect the reaction.

The inert solvent may, for example, be methylene chloride, tetrahydrofuran or dimethylformamide, and the base may, for example, be triethylamine, 4-dimethylaminopyridine or imidazole.

The reaction temperature is usually from −20° C. to the boiling point of the solvent used for the reaction, preferably from 0° C. to room temperature, and the reaction time is usually from 10 minutes to 7 days, preferably from 30 minutes to 24 hours.

The step of producing the compound of the formula 21 from the compound of the formula 19, can be conducted by firstly effecting so-called Mitsunobu reaction in which diethyl azodicarboxylate, triphenylphosphine and phthalimide (or hydrogen azide) are reacted to the compound 19, or sulfonylating it with a sulfonylation agent of the formula 20 in the presence of a base such as triethylamine, and then reacting phthalimide in the presence of a base (or sodium azide) thereto, to convert the secondary hydroxyl group of the compound 19 to a phthalimide group or an azide group, and then removing the protecting group for the primary hydroxyl group represented by E, followed by oxidation.

The first step of converting the secondary hydroxyl group to the phthalimide group (or the azide group), can be conducted in the same manner as the step for producing the phthalimide-protected compound (or the azide compound) of the compound (II-a) by phthalimide-formation (or azide-formation) of the compound 7 in the above described Process A. Accordingly, with respect to the reaction conditions, the same reaction conditions as in Process A can be used.

The step of removing the protecting group of the primary hydroxyl group represented by E from the phthalimide compound (or the azide compound) obtained by the above reaction, can be conducted usually in a solvent inert to the reaction depending upon the type of the protecting group, for example, in the case where the protecting group is a trityl group, by treatment with an acid such as acetic acid, formic acid, trifluoroacetic acid, hydrochloric acid, sulfuric acid or p-toluenesulfonic acid, or in the case where the protecting group is a tert-butyldimethylsilyl group, by treatment with the same acid as above or with a fluoride such as tetrabutylammonium fluoride or potassium fluoride.

The solvent for the reaction varies depending upon e.g. the type of each reaction and the stability of the compound. However, when an acid is used for the treatment, methylene chloride, methanol, ethanol, tetrahydrofuran or a solvent mixture thereof with water may be used, and especially when acetic acid, formic acid or trifluoroacetic acid is used as the acid, it is preferred to conduct the reaction using such an acid itself or a mixture of such an acid with water, as the solvent. Further, when a fluoride such as tributylammonium fluoride or potassium fluoride is used, it is preferred to employ, for example, tetrahydrofuran, methylene chloride or dimethylformamide.

In either case of treatment with an acid or using a fluoride, the reaction temperature is usually from −20° C. to the boiling point of the solvent used for the reaction, preferably from −20° C. to 50° C., and the reaction time is usually from 10 minutes to 48 hours, preferably from 30 minutes to 24 hours.

The step of oxidizing the primary alcohol compound thus obtained to the aldehyde compound 21, is conducted usually by using e.g. pyridinium chlorochromate, pyridinium dichromate, sulfur trioxide pyridine complex, or oxalyl chloride and dimethyl sulfoxide (so called Swern oxidation condition), as an oxidizing agent, in a solvent inert to the reaction.

As the inert solvent, a halogenated hydrocarbon such as methylene chloride or chloroform, is usually preferred. The oxidizing agent is used usually in an amount of 1 mol or an excess molar amount, preferably from 1 to 2 mols, per mol of the starting material alcohol.

The reaction temperature is usually from −80° C. to the boiling point of the solvent used for the reaction, preferably from −80° C. to 0° C. when oxalyl chloride and dimethyl sulfoxide are used as the oxidizing agents, or from −20° C. to room temperature when other oxidizing agents are employed.

The reaction time is usually from 10 minutes to 48 hours, preferably from 30 minutes to 24 hours, irrespective of the type of the oxidizing agent.

The step of producing the compound of the formula (II-c) from the aldehyde compound 21, can be accomplished by reacting the aldehyde compound 21 with a Wittig reagent of the formula 22 to obtain a vinylene derivative, which is then reacted with hydrazine to remove the phthalimide group (or to reduce the azide group).

The first step of reacting the aldehyde compound 21 with the Wittig reagent of the formula 22, can be conducted usually by reacting 1 mol or an excess molar amount, preferably from 1 to 1.5 mols, of the Wittig reagent 22 to 1 mol of the aldehyde compound 21 in an inert solvent which does not adversely affect the reaction.

This reaction is usually preferably conducted in the presence of a base or by treating the Wittig reagent 22 with a base beforehand.

As such a base, an alkali metal hydride such as sodium hydride, lithium hydride or potassium hydride; an alkyllithium such as methyllithium, butyllithium or tert-butyllithium; an alkali metal alkoxide such as sodium methoxide, sodium ethoxide or potassium tert-butoxide; or an alkali metal hydroxide such as sodium hydroxide or potassium hydroxide, may, for example, be mentioned.

Such a base is used usually in an amount of 1 mol or an excess molar amount, preferably from 1 to 1.5 mols, per mol of the Wittig reagent of the formula 22.

The reaction temperature is usually from −100° C. to the boiling point of the solvent used for the reaction, preferably from −80° C. to 50° C., and the reaction time is usually from 10 minutes to 48 hours, preferably from 30 minutes to 24 hours.

Then, the step of reacting hydrazine to the vinylene derivative to remove the phthalimide group (or to reduce the azide group) to obtain the compound of the formula (II-c), can be conducted in the same manner as the step of producing the compound (II-a) by removing the phthalimide group of the phthalimide-protected compound (or reducing the azide group of the azide compound) of the compound (II-a) obtained by converting the compound 7 in the above described Process A. Accordingly, also with respect to the reaction conditions, the conditions for such a step can be used.

The compounds of the formulas 16 and 22 may be commercially available or can be produced by a proper combination, as the case requires, of the methods disclosed in Examples and Reference Examples, or conventional methods or methods similar thereto.

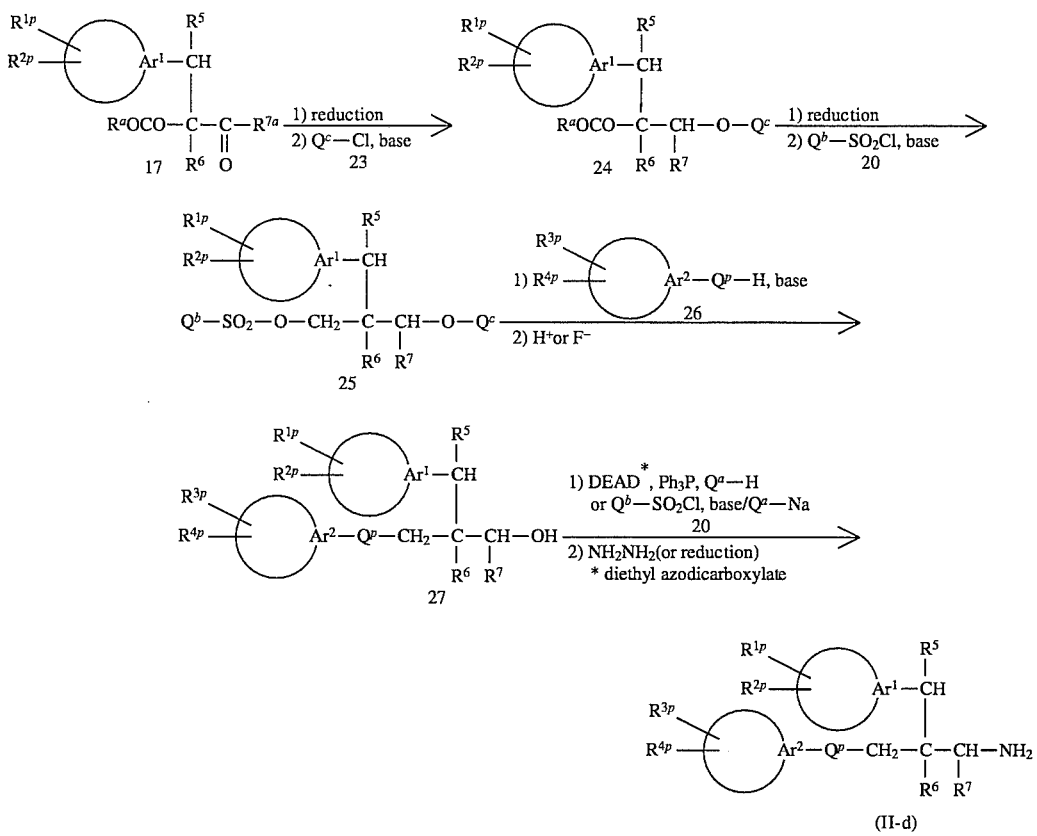

PROCESS D

In the above formulas,

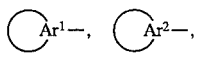

$R^{1p}, R^{2p}, R^{3p}, R^{4p}, R^5, R^6, R^7, R^a, Q^a$ and $Q^b$ are as defined above, $Q^c$ is a trityl group, a tetrahydropyranyl group, a methoxymethyl group or a tert-butyldimethylsilyl group; and $Q^p$ is an oxygen atom or a sulfur atom.

Process D is a process for producing a compound of the formula (II-d) i.e. an intermediate useful for the production of an ether derivative or a sulfide derivative of the formula (I) wherein Q is a group of the formula —O—CH$_2$— or —S—CH$_2$—, respectively.

According to this process, the desired compound (II-d) can be prepared by firstly reducing the ketone group of the compound of the formula 17 to a hydroxyl group with a metal hydride complex or the like, protecting the hydroxyl group to obtain a compound of the formula 24, reducing the ester group of the compound 24 to a hydroxymethyl group again with a metal hydride complex, sulfonylating the hydroxymethyl group with a sulfonylation agent of the formula 20 to obtain a compound of the formula 25, reacting a compound of the formula 26 to the compound 25 to obtain an ether compound or a sulfide compound, then removing the hydroxyl-protecting group to obtain a compound of the formula 27, reacting diethyl azodicarboxylate, triphenylphosphine and phthalimide (or hydrogen azide) to the compound 27, or sulfonylating it with a sulfonylation agent of the formula 20 in the presence of a base, followed by reacting phthalimide in the presence of a base (or sodium azide) to obtain a phthalimide compound (or an azide compound), and finally reacting hydrazine (or a reducing agent) thereto to remove the phthalimide group (or to reduce the azide group).

The above reaction steps will be described in detail referring to suitable reaction conditions.

The step of reducing the compound of the formula 17, can be conducted usually by using a metal hydride complex such as sodium borohydride or lithium tri-secbutylborohydride, in an inert solvent which does not adversely affect the reaction.

With respect to the reaction conditions, etc., in this reduction reaction, the conditions, etc. of the reduction reaction of the compound 17 in the above described Process C can be used without change.

The step of preparing the hydroxyl-protected compound 24 from the reduced compound obtained by the above reaction, can be conducted by using e.g. tert-butyldimethylchlorosilane, trityl chloride, chlorodimethyl ether or 2,3-dihydropyran usually in an inert solvent which does not adversely affect the reaction.

In the above reaction, when a chloride such as trityl chloride, chlorodimethyl ether or tert-butyldimethylchlorosilane, is used as the protecting reagent, the reaction conditions for the step of protecting the hydroxyl group after the reduction of compound 17 in the above described Process C can be applied usually without change. Further, when 2,3-dihydropyran is used as the protecting reagent, the reaction can be conducted usually by using a halogenated hydrocarbon such as methylene chloride or chloroform as the solvent in the presence of a catalyst such as p-toluenesulfonic acid or pyridinium p-toluenesulfonate.

2,3-Dihydropyran is used usually preferably in an excess amount to the starting material alcohol compound.

The reaction temperature is usually from −80° C. to the boiling point of the solvent used for the reaction, preferably from −20° C. to room temperature, and the reaction time is usually from 5 minutes to 48 hours, preferably from 30 minutes to 24 hours.

The step of producing a compound of the formula 25 from the compound of the formula 24, can be accomplished by firstly reducing the ester group of the compound 24 with e.g. a metal hydride complex such as lithium aluminum hydride or lithium borohydride in an inert solvent which does not adversely affect the reaction, and sulfonylating the hydroxyl group of the obtained alcohol compound with a sulfonylation agent of the formula 20 in the presence of a base in an inert solvent which does not adversely affect the reaction. These steps can be conducted in the same manner as the step of reducing the ester group of the compound 17 and the step of sulfonylating the compound 19 in the above described Process C. Accordingly, also with respect to the reaction conditions, similar conditions can be used.

The step of producing the compound of the formula 27 from the sulfonyloxy compound 25, can be conducted by reacting the compound of the formula 26 to the sulfonyloxy compound 25 in the presence of a base usually in an inert solvent which does not adversely affect the reaction to obtain an ether derivative or a sulfide derivative, and treating the ether derivative or the sulfide derivative with e.g. an acid or a fluoride usually in an inert solvent which does not adversely affect the reaction.

In the first step of etherification or sulfide-formation, as the inert solvent, e.g. methylene chloride, tetrahydrofuran, benzene or dimethylformamide is usually preferred, and as the base, e.g. sodium hydride, sodium hydroxide, potassium hydroxide, sodium carbonate or potassium carbonate is preferred.

With respect to the amount of the reagents to be used, it is usual that the compound of the formula 26 is 1 mol or an excess molar amount, preferably from 1 to 2 mols, per mol of the sulfonyloxy compound 25, and the base is 1 mol or an excess molar amount, preferably from 1 to 5 mols, per mol of the compound of the formula 26.

The reaction temperature is usually from −80° C. to the boiling point of the solvent used for the reaction, preferably from −20° C. to 100° C., and the reaction time is usually from 5 minutes to 48 hours, preferably from 30 minutes to 24 hours.

The process for producing the compound of the formula (II-d) from the alcohol compound 27, can be conducted by firstly treating the alcohol compound 27 with diethyl azodicarboxylate, triphenylphosphine and phthalimide (or hydrogen azide), or sulfonylating it with a sulfonylation agent of the formula 20 in the presence of a base such as triethylamine, followed by treating it with phthalimide in the presence of a base (or sodium azide) to convert it to a phthalimide compound (or an azide compound), and then treating the obtained phthalimide compound (or the azide compound) with hydrazine (or a reducing agent) usually in an inert solvent which does not adversely affect the reaction.

The above reactions can be conducted in the same manner as the reaction for introducing a phthalimide group (or an azide group) to the compound 7 or 19 and the reaction for removing the phthalimide group (or reducing the azide group) as the final step in the above described Processes A and C. Accordingly, also with respect to the reaction conditions, similar conditions can be used.

The compound of the formula 26 may be a commercially available or can be produced by a proper combination, as the case requires, of the methods disclosed in Examples and Reference Examples, conventional methods or methods similar thereto.

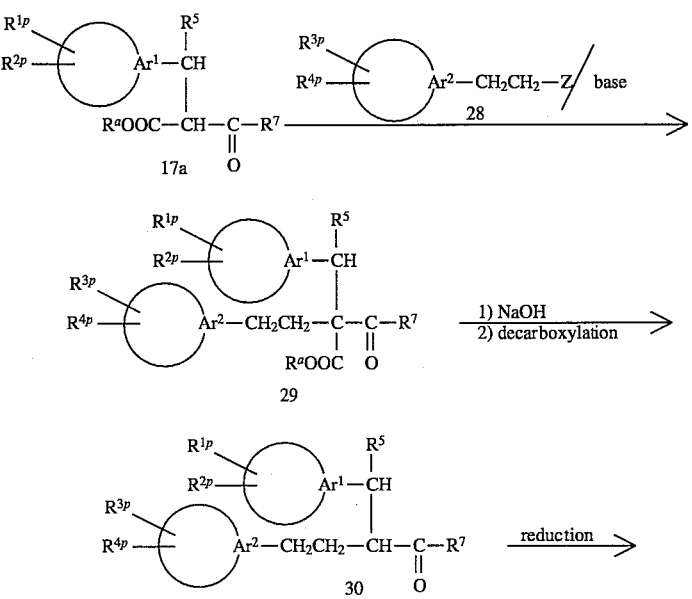

PROCESS E

-continued
PROCESS E

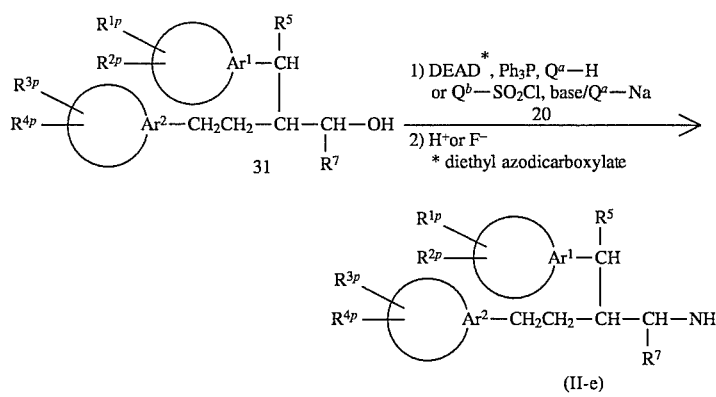

(II-e)

In the above formulas,

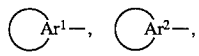

$R^{1p}$, $R^{2p}$, $R^{3p}$, $R^{4p}$, $R^5$, $R^6$, $R^7$, $R^a$, $Q^a$, $Q^b$ and Z are as defined above.

Process E is a process for producing a compound of the formula (II-e) i.e. an intermediate useful for the production of the ethylene derivative of the formula (I) wherein Q is a group of the formula —CH$_2$CH$_2$—, and $R^6$ is a hydrogen atom.

According to this process, the desired compound (II-e) can be produced by firstly reacting an alkylating agent of the formula 28 to the β-ketoacid derivative of the formula 17a to obtain an alkyl compound 29, then hydrolyzing the ester group of the alkyl compound, followed by decarboxylation to obtain a compound 30, reducing the compound 30 with a reducing agent such as a metal hydride complex to obtain an alcohol compound 31, then reacting to the obtained alcohol compound 31 diethyl azodicarboxylate, triphenylphosphine and phthalimide (or hydrogen azide), or sulfonylating the hydroxyl group with a sulfonylation agent of the formula 20 in the presence of a base, followed by reacting phthalimide thereto in the presence of a base (or sodium azide) to produce a phthalimide compound (or an azide compound), and finally reacting hydrazine (or a reducing agent) thereto to remove the phthalimide group (or to reduce the azide group).

The above reaction steps will be described in detail referring to suitable reaction conditions.

The first step of producing the alkyl compound 29 from the β-ketoacid derivative 17a, can be conducted in the same manner as the process of alkylating the β-ketoacid derivative 16 with an alkylating agent 5 in the above described Process C. Accordingly, also with respect to the reaction conditions, similar conditions can be used.

The steps of hydrolyzing the alkyl compound 29, followed by decarboxylation, can be conducted by reacting a base such as an alkali metal hydroxide or an alkali metal carbonate, such as sodium hydroxide, potassium hydroxide, lithium hydroxide, sodium carbonate or potassium carbonate, in an inert solvent which does not adversely affect the reaction, such as methanol, ethanol, propanol, tetrahydrofuran, dioxane or a solvent mixture thereof with water, to hydrolyze the ester group, treating the obtained alkali metal carboxylate with an acid to convert it to the free carboxylic acid, followed by heating preferably at a temperature of from 50° C. to 100° C., in a solvent which does not adversely affect the reaction, such as benzene, toluene, methanol, ethanol, tetrahydrofuran, dioxane, dimethylformamide or acetic acid. Here, the reaction time required for decarboxylation is usually from 1 minute to 48 hours, preferably from 10 minutes to 24 hours.

Then, the steps of reducing the ketone compound 30 thus obtained, with a reducing agent such as a metal hydride complex, to produce the alcohol compound 31, converting the alcohol compound thus obtained to a phthalimide compound (or an azide compound), and finally reacting hydrazine (or a reducing agent) thereto to obtain the desired compound (II-e), can be conducted in the same manner as the step of reducing the compound 6, 11 or 17 in the above described Processes A, B, C and D, to obtain the alcohol compound, and the step of forming the phthalimide or azide compound 7, 19 or 27 and subsequently removing the phthalimide group (reducing the azide group) in the above described Processes A, C and D. Accordingly, also with respect to the reaction conditions, similar conditions can be used.

The compound of the formula 28 may be commercially available or can be produced by a proper combination, as the case requires, of the methods disclosed in Examples and Reference Examples, or conventional methods or methods similar thereto.

PROCESS F

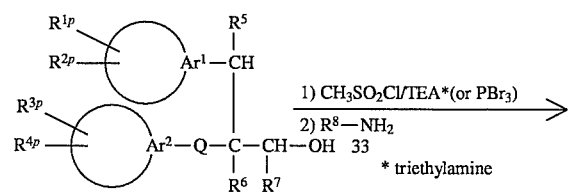

-continued
PROCESS F

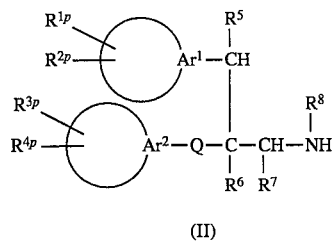

(II)

In the above formulas,

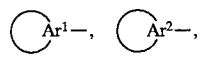

$Q, R^{1p}, R^{2p}, R^{3p}, R^{4p}, R^5, R^6, R^7$ and $R^8$ are as defined above Process F is a process for producing an amine product (II) from the compound of the formula 32.

According to this process, the desired amine compound (II) can be produced by reacting a sulfonating agent such as methanesulfonyl chloride to the alcohol compound of the formula 32 in the presence of a base, or reacting a halogenating agent such as thionyl chloride or phosphorus tribromide thereto, to convert the hydroxyl group in the formula to a leaving group, followed by reacting an amine compound of the formula 33.

The reaction for introducing the leaving group can be conducted usually by reacting 1 mol or an excess molar amount, preferably from 1 to 2 mols, of a sulfonating agent and a base to 1 mol of the alcohol compound 32 in an inert solvent such as methylene chloride, chloroform, benzene, tetrahydrofuran or ethyl acetate, or using 1 mol or an excess molar amount, preferably from 1 to 5 mols, of a halogenating agent.

The reaction temperature is usually from −70° C. to the boiling point of the solvent used for the reaction, preferably from −20° C. to 80° C., and the reaction time is usually from 5 minutes to 48 hours, preferably from 30 minutes to 24 hours.

Then, the step of reacting an amine compound 33 to the compound having the leaving group introduced, obtained by the above reaction, can be conducted usually by employing 1 mol or an excess molar amount, preferably from 1 to 50 mols, of the amine compound 33 per mol of the starting compound having the leaving group, in an inert solvent such as methylene chloride, chloroform, benzene, ethyl ether or tetrahydrofuran.

If necessary, this reaction can be conducted in the presence of a base other than the amine compound of the formula 33.

As such a base, an inorganic base such as sodium hydroxide, potassium hydroxide, calcium hydroxide, sodium carbonate, potassium carbonate or sodium hydrogencarbonate, or an organic base such as triethylamine, N-ethyldiisopropylamine, pyridine or N,N-dimethylaniline may, for example, be mentioned.

Such a base is used usually in an amount of 1 mol or an excess molar amount, preferably from 1 to 5 mols, per mol of the starting material compound.

The reaction temperature is usually from −50° C. to 150° C., preferably from −20° C. to 100° C., and the reaction time is usually from 5 minutes to 7 days, preferably from 10 minutes to 24 hours.

The compound of the formula 33 may be a commercially available or can be prepared by a proper combination, as the case requires, of the methods disclosed in Examples and Reference Examples, or conventional methods or methods similar thereto.

PROCESS G

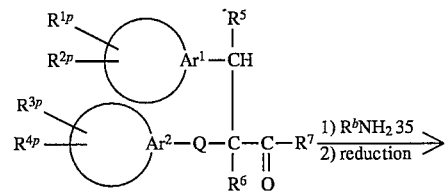

34

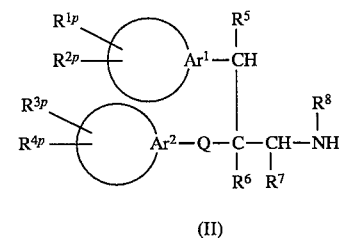

(II)

In the above formulas,

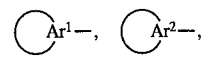

$Q R^{1p}, R^{2p}, R^{3p}, R^{4p}, R^5, R^6, R^7$ and $R^8$ are as defined above, and $R^b$ is a hydroxyl group, a lower alkyl group, a lower alkenyl group, a lower alkynyl group or an aralkyl group.

Process G is a process for preparing an amine compound (II) from the ketone compound of the formula 34.

According to this process, the desired compound (II) can be produced by reacting the compound of the formula 35 in an amount of 1 mol or an excess molar amount, preferably from 1 to 2 mols, per mol of the starting material carbonyl compound 34 usually in an inert solvent such as methanol, ethanol, benzene, ethyl ether or tetrahydrofuran, to preliminarily form an oxime or imine, which is then reduced.

The reaction temperature for the process for forming the above oxime or imine, is usually from 0° C. to the boiling point of the solvent used for the reaction, preferably from room temperature to 100° C. The reaction time is usually from 5 minutes to 48 hours, preferably from 30 minutes to 24 hours. After formation of the oxime or imine, the reaction solution may be used by itself for the next step of the reduction reaction, or the oxime compound or the imine compound may be isolated by evaporating the reaction solution or by using a conventional separation method and then subjected to the subsequent reduction reaction.

The reduction reaction can be conducted by using a metal hydride complex such as sodium borohydride, sodium cyanoborohydride or lithium aluminum hydride, or by catalytic reduction employing a palladium-carbon catalyst or a Raney nickel catalyst.

When the metal hydride complex is used as the reducing agent, the reducing agent may be used usually in an amount of 1 mol or an excess molar amount, preferably from 1 to 5 mols, per mol of the above-mentioned imine.

For this reduction reaction, a solvent is suitably selected for use depending upon the type of the reducing agent. For example, an inert solvent, such as an alcohol such as methanol or ethanol; an ether such as dimethyl ether, ethyl ether, diisopropyl ether, dibutyl ether, dimethoxyethane, dioxane, tetrahydrofuran or diglyme; an aliphatic hydrocarbon such as pentane, hexane, heptane or cyclohexane; or an aromatic hydrocarbon such as benzene, or toluene, or a solvent mixture thereof, may be used.

The reaction temperature is usually from 0° C. to room temperature, and the reaction time is usually from 1 hour to 6 hours.

The compound of the formula 34 can be prepared in accordance with the methods in the above described Process A or methods similar thereto, and the compound of the formula 35 may be commercially available or can be prepared by a proper combination, as the case requires, of conventional methods or methods similar thereto.

PROCESS H

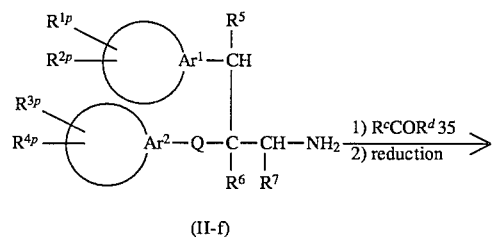

(II-f)

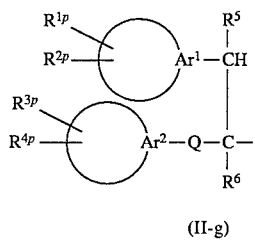

(II-g)

In the above formulas,

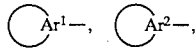

Q, $R^{1p}$, $R^{2p}$, $R^{3p}$, $R^{4p}$, $R^5$, $R^6$ and $R^7$ are as defined above, $R^c$ is a hydrogen atom, a lower alkyl group, a lower alkenyl group, a lower alkynyl group or an aralkyl group; $R^d$ is a hydrogen atom or a lower alkyl group; and $R^e$ is a lower alkyl group, a lower alkenyl group, a lower alkynyl group or an aralkyl group.

Process H is a process for producing a compound of the formula (II-g) i.e. an intermediate useful for the production of the compound of the formula (I) of the present invention wherein substituent $R^8$ on the nitrogen atom is a lower alkyl group, a lower alkenyl group, a lower alkynyl group or an aralkyl group.

According to this process, the desired compound (II-g) can be produced by reacting the compound of the formula 36 in an amount of 1 mol or an excess molar amount, preferably from 1 to 2 mols, to 1 mol of the compound of the formula (II-f) usually in an inert solvent such as methanol, ethanol, benzene, ethyl ether or tetrahydrofuran, to preliminarily form an imine, which is subsequently reduced.

The reaction temperature for the process for forming the above imine, is usually from 0° C. to the boiling point of the solvent used for the reaction, preferably from room temperature to 100° C. The reaction time is usually from 5 minutes to 48 hours, preferably from 30 minutes to 24 hours. After formation of the imine, the reaction solution may be used by itself to the subsequent step of the reduction reaction, or the imine compound may be isolated by evaporating the reaction solution or by means of a conventional separation method and then subjected to the subsequent reduction reaction.

The reduction reaction can be conducted by using a metal hydride complex such as sodium borohydride, sodium cyanoborohydride or lithium aluminum hydride, or by catalytic reduction employing a palladium-carbon catalyst or a Raney nickel catalyst.

When a metal hydride complex is used as the reducing agent, the reducing agent is usually in an amount of 1 mol or an excess molar amount, preferably from 1 to 5 mols, per mol of the above imine.

For such a reduction reaction, a solvent is suitably selected for use depending upon the type of the reducing agent. For example, an inert solvent, such as an alcohol such as methanol or ethanol; an ether such as dimethyl ether, ethyl ether, diisopropyl ether, dibutyl ether, dimethoxyethane, dioxane, tetrahydrofuran or diglyme; an aliphatic hydrocarbon such as pentane, hexane, heptane or cyclohexane; or an aromatic hydrocarbon such as benzene or toluene, or a solvent mixture thereof, may be employed.

The reaction temperature is usually from 0° C. to room temperature, and the reaction time is usually from 1 hour to 6 hours.

The compound of the formula 36 may be commercially available, or can be produced by a suitable combination, as the case requires, of the methods disclosed in Examples and Reference Examples, or conventional methods or similar methods thereof.

PROCESS I

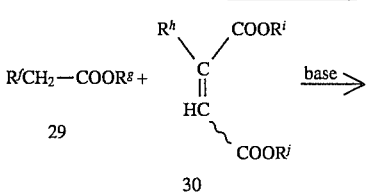

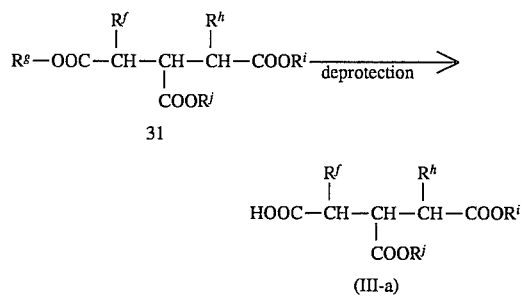

(III-a)

In the above formulas, each of $R^f$ and $R^h$ which are the same or different, is a hydrogen atom, a lower alkyl group, an aryl group or an aralkyl group; each of $R^i$ and $R^j$ which are the same or different, is a carboxyl-protecting group; and $R^g$ is a tert-butyl group, a benzyl group, a benzhydryl group or a trityl group.

Process I is a process for producing a carboxylic acid derivative of the formula (III-a) among the compounds of the above formula (III).

According to this process, the desired carboxylic acid derivative (III-a) can be produced by conducting a so-called Michael addition reaction which comprises reacting a maleic acid derivative or a fumaric acid derivative of the formula 30 to an ester derivative having a readily removable carboxyl-protecting group $R^g$, represented by the formula 29, in the presence of a base, and then removing the carboxyl-protecting group $R^g$ from the obtained Michael addition product 31 under a mild condition.

As the carboxyl-protecting group for $R^i$ and $R^j$, a lower alkyl group such as a tert-butyl group, or a benzhydryl group, is preferred.

The protecting group $R^g$ is preferably the one which can readily be removed under a mild condition of catalytic reduction or weakly acidic condition and which is stable under the Michael addition reaction condition, such as a tert-butyl group, a benzyl group, a benzhydryl group or a trityl group.

The above Michael addition reaction can be conducted by reacting the compound of the formula 30 in an amount of 1 mol or an excess molar amount, preferably from 1 to 2 mols, to 1 mol of the compound of the formula 29 in the presence of a base such as sodium hydride, butyllithium, lithium diisobutylamide or lithium bis(trimethylsilyl)amide usually in an inert solvent such as benzene, ethyl ether or tetrahydrofuran.

Such a base is used usually in an amount of 1 mol or a slightly excess molar amount, preferably from 1 to 1.5 mols, per mol of the compound of the formula 30.

The reaction temperature is usually from −100° C. to 100° C., preferably from −80° C. to room temperature, and the reaction time is usually from 5 minutes to 24 hours, preferably from 10 minutes to 10 hours.

The reaction conditions for the reaction for removing the protecting group from the compound of the formula 31 to form the desired carboxylic acid derivative (III-a), vary depending upon the type of the protecting group, etc. For example, when the protecting group is a tert-butyl group, a benzhydryl group or a trityl group, a method may be employed wherein the compound is treated with an acid such as acetic acid, formic acid, trifluoroacetic acid or hydrochloric acid, preferably within a temperature range of from −20° C. to 50° C. for from 10 minutes to 24 hours in the absence of a solvent or usually in an inert solvent such as methylene chloride, anisole, tetrahydrofuran, methanol or ethanol or a solvent mixture thereof with water.

For example, when the protecting group is a benzyl group, a benzhydryl group or a trityl group, a method may be employed wherein the compound is catalytically reduced with a catalyst such as a palladium-carbon catalyst or a Raney nickel catalyst preferably under a hydrogen pressure of from 1 to 20 kg/cm² preferably within a temperature range of from 0° C. to 40° C. for from 10 minutes to 24 hours usually in an inert solvent such as methanol, ethanol, water or acetic acid, or a solvent mixture thereof.

Among compounds of the formula (III-a), an optically active compound of the formula (III-b¹):

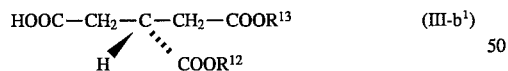
(III-b¹)

or the formula (III-b²):

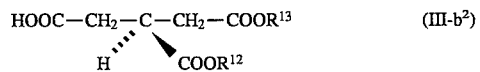
(III-b²)

wherein each of $R^{12}$ and $R^{13}$ which are the same or different, is a carboxyl-protecting group, can be obtained by reacting a racemic mixture of the compound of the formula (III-b):

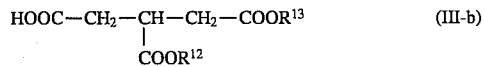
(III-b)

wherein $R^{12}$ and $R^{13}$ are as defined above, with cinchonidine or quinine to obtain a mixture of two diastereomers, then separating and collecting either one of the diastereomers by utilizing the difference in the solubility as between the two diastereomers, followed by recovering the free carboxylic acid by treating with an acid.

Separation of the diastereomer mixture may be conducted in an organic solvent such as carbon tetrachloride or isopropyl ether. Usually, the mixture of the diastereomers is dissolved in a solvent in a hot state, and the solution is gradually cooled to utilize the solubility difference for separation of the diastereomers.

Further, either one of the diastereomers thus obtained is treated with an acid such as hydrochloric acid to obtain an optically active compound of the formula (III-b¹) or (III-b²).

The compounds of the formula 29 and 30 may be commercially available or can be produced by a proper combination, as the case requires, of the methods disclosed in Examples and Reference Examples, or conventional methods or methods similar thereto.

A compound of the formula (II'):

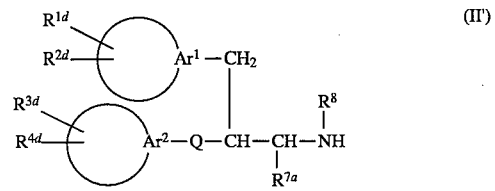
(II')

wherein

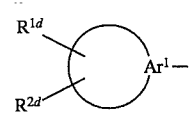

is a group of the formula

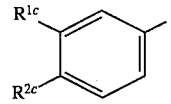

(wherein each of $R^{1c}$ and $R^{2c}$ which are the same or different, is a hydrogen atom, a halogen atom, a lower alkyl group or a lower alkoxy group) or a naphthyl group;

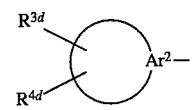

is a group of the formula

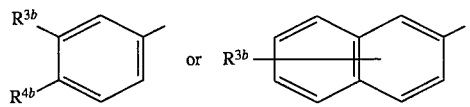

(wherein $R^{3b}$ is a hydrogen atom, a halogen atom, a lower alkyl group or a lower alkoxy group; and $R^{4b}$ is a hydrogen atom, a halogen atom, a lower alkyl group, a lower alkoxy group, or an aryl or heteroaromatic ring group which may have substituent(s) selected from the group consisting of a halogen atom, a lower alkyl group and a lower alkoxy group, provided that when Q is a single bond, $R^{4b}$ is an aryl or heteroaromatic ring group which may have substituent(s) selected from the group consisting of a halogen atom, a lower alkyl group and a lower alkoxy group); Q is a single bond or a group of the formula —CO—O—, —O—CO—, —CH₂CH₂—, —CH=CH—, —OCH₂—, —SCH₂—, —CH₂O— or —CH₂S—; $R^{7a}$ is a lower alkyl group; and $R^8$ is a hydrogen atom, a lower alkyl group, a lower alkenyl group, a lower alkynyl group or an aralkyl group, and a compound of the formula (III-b¹):

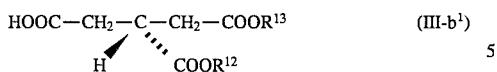

wherein each of $R^{12}$ and $R^{13}$ which are the same or different, is a carboxyl-protecting group, or the formula (III-b²):

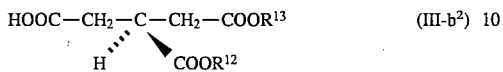

wherein $R^{12}$ and $R^{13}$ are as defined above, obtained by the above processes, are important intermediates useful for the production of the compound of the formula (I), and they are novel compounds not disclosed in any literatures.

The present invention is concerned also with the compound of the formula (II'), the compound of the formula (III-b¹) and the compound of the formula (III-b²).

Among compounds of the formula (II'), a compound of the formula (II'-1):

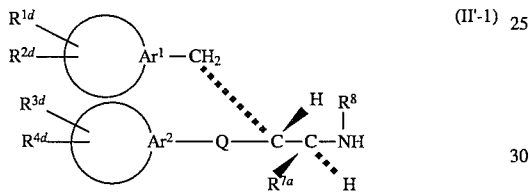

wherein

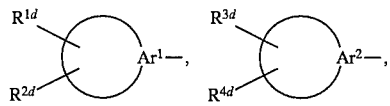

Q, $R^{7a}$ and $R^8$ are as defined above, or a compound of the formula (II'-2):

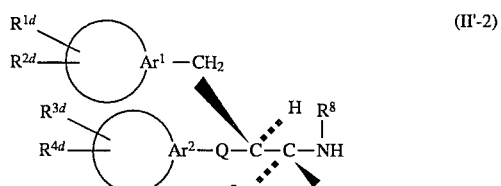

wherein

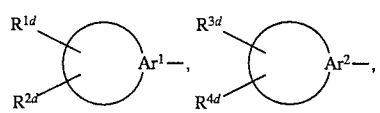

Q, $R^{7a}$ and $R^8$ are as defined above, is preferred. Particularly preferred is the compound of the formula (II'-1).

In the formula (II'),

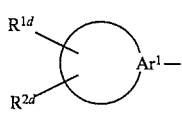

is a group of the formula

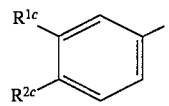

(wherein each of $R^{1c}$ and $R^{2c}$ which are the same or different, is a hydrogen atom, a halogen atom, a lower alkyl group or a lower alkoxy group) or a naphthyl group. Specifically, it may, for example, be a phenyl group, a 3-chlorophenyl group, a 4-chlorophenyl group, a 4-fluorophenyl group, a 4-methylphenyl group, a 3,4-dichlorophenyl group, a 4-methoxyphenyl group, a 3-bromophenyl group, a 1-naphthyl group or a 2-naphthyl group, preferably a 3,4-dichlorophenyl group, a 4-chlorophenyl group, a 1-naphthyl group or a 2-naphthyl group.

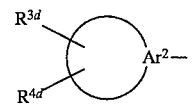

is a group of the formula

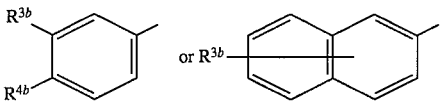

wherein $R^{3b}$ is a hydrogen atom, a halogen atom, a lower alkyl group or a lower alkoxy group; and $R^{4b}$ is a hydrogen atom, a halogen atom, a lower alkyl group, a lower alkoxy group, or an aryl or heteroaromatic ring group which may have substituent(s) selected from the group consisting of a halogen atom, a lower alkyl group and a lower alkoxy group, provided that when Q is a single bond, $R^{4b}$ is an aryl or heteroaromatic ring group which may have substituent(s) selected from the group consisting of a halogen atom, a lower alkyl group and a lower alkoxy group. Specifically, it may, for example, be a 4-biphenylyl group, a phenyl group, a 4-chlorophenyl group, a 4-methylphenyl group, a 4-bromophenyl group, a 4-tert-butylphenyl group, a 4-methoxyphenyl group, a 3-chlorophenyl group, a 2-naphthyl group, a 4'-chloro-4-biphenylyl group, a 4-(3-thienyl)phenyl group, a 4-(3-pyridyl)phenyl group, a 3'-chloro-4-biphenylyl group, a 3,4-dichlorophenyl group, a 3,4-difluorophenyl group, a 3,4-dimethylphenyl group, a 3-chloro-4-methylphenyl group, a 4-chloro-3-methylphenyl group, a 3,4-dimethoxyphenyl group, a 3,4-methylenedioxyphenyl group, a 3-bromophenyl group, a 4-(2-naphthyl)phenyl group, a 2-fluoro-4-biphenylyl group, a 4-(2-furyl)phenyl group, a 3',4'-methylenedioxy-4-biphenylyl group, a 2'-fluoro-4-biphenylyl group, a 2'-methoxy-4-biphenylyl group or a 4(5-oxazolyl)phenyl group. However, when Q in the formula (II') is a single bond, it may, for example, be a 4-biphenylyl group, a 2-naphthyl group, a 4'-chloro-4-biphenylyl group, a 4-(3-thienyl)phenyl group, a 4-(3-pyridyl)phenyl group, a 3'-chloro-4-biphenylyl group, a 3,4-dichlorophenyl group, a 4-(2-naphthyl)phenyl group, a 2-fluoro-4-biphenylyl group, a 4-(2-furyl)phenyl group, a 3',4'-methylenedioxy-4-biphenylyl group, a 2'-fluoro-4-biphenylyl group, a 2'-methoxy-4-biphenylyl group or a 4-(5-oxazolyl)phenyl group.

In the compound of the formula (III-b¹) or (III-b²), each of $R^{12}$ and $R^{13}$ which are the same or different, is a carboxyl-protecting group, which may, for example, be preferably a lower alkyl group such as a tert-butyl group, or a benzhydryl group. Particularly preferred is a tert-butyl group.

To demonstrate the usefulness of the compounds of the present invention, 50% inhibitory concentrations ($IC_{50}$ values) of the compounds of the present invention against the squalene synthase activities, were obtained.

Inhibitory activities against squalene synthase (1) Preparation of a microsome fraction A microsome fraction was prepared from human-hepatoma(Hep G2) cells by the method of Shechter et al disclosed in J. Biol. Chem., 267, 8628 (1992).

Namely, Hep G2 cells were homogenized in the presence of a 0.3M sucrose-1 mM DTT-1 mM EDTA-10mM Hepes buffer solution (pH 7.4) and various protease inhibitors, and subjected to centrifugal separation at 2000 x g for 5 minutes and 10000 x g for 15 minutes. The obtained supernatant was further subjected to centrifugal separation at 105000 x g for 60 minutes, whereupon the precipitated residue was obtained. This precipitated residue was suspended in the above buffer solution containing various protease inhibitors, and the suspension was further subjected to centrifugal separation at 105000 x g for 30 minutes to wash the precipitated residue. This washing operation was repeated three times. The finally obtained precipitated residue was taken as a microsome fraction, which was suspended in the above buffer solution containing no such various protease inhibitors, and the suspension was used for measuring the enzyme activities.

(2) Method for measuring squalene synthase activities

The enzymatic reaction of the squalene synthase was conducted in accordance with the method of Shechter et al disclosed in J. Biol. Chem., 267, 8628 (1992).

Namely, 1 µl of a dimethyl sulfoxide solution containing a compound of the present invention was added to a 50 µl of the reaction solution containing the microsome fraction prepared in the above step (1) (microsome fraction: 2–20 µg, 5 mM $MgCl_2$, 10 mM DTT, 2mM NADPH, 10 µM $^3$H]-farnesyl pyrophosphate, 100 mM phosphate buffer solution (pH 7.4)), and the mixture was shaked and reacted at 37° C. for 20 minutes. Separation of [$^3$H]-squalene formed in the reaction solution and [$^3$H]-farnesyl pyrophosphate, was conducted in accordance with the method of Tait et al disclosed in Anal. Biochem., 203, 310 (1992). The radio activity of [$^3$H]-squalene was measured by a liquid scintillation counter and taken as the enzyme activity. Then, a 50% inhibitory concentration ($IC_{50}$ value) of the compound of the present invention against the squalene synthase activity was obtained. The results are shown in the following Table.

| 50% inhibitory concentration against squalene synthase activity | |
|---|---|
| Compounds | $IC_{50}$ (nM) |
| Example 32 | 4.7 |
| Example 35 | 5.4 |
| Example 46 (2R-form) | 3.2 |
| Example 49 | 3.0 |
| Example 70 | 1.4 |
| Example 92 | 0.5 |
| Example 102 | 1.7 |
| Example 112 | 3.1 |

From the above results, it is evident that the compounds of the present invention have excellent squalene synthase inhibitory activities and thus are useful for the treatment and/or prophylaxis of hypercholesterolemia, hyperlipemia and arteriosclerosis.

Further, the compounds of the present invention have squalene synthase inhibitory activities against fungus, and they are useful also as antifungal agents.

The compound of the formula (I) of the present invention can be orally or parenterally administered, and it may be formulated into a formulation suitable for such administration, so that it can be used as a therapeutic or prophylactic agent for hypercholesterolemia, hyperlipemia or arteriosclerosis, or as an antifungal agent. To use the compound of the present invention for clinical purpose, it may be formulated into various formulations by an addition of pharmaceutically acceptable additives to meet the type of administration and then administered. As such additives, various additives which are commonly used in the field of drug formulations, may be used, including, for example, gelatin, lactose, saccharose, titanium oxide, starch, crystalline cellulose, hydroxypropylmethylcellulose, carboxymethylcellulose, corn starch, microcrystalline wax, white petrolatum, magnesium metasilicate aluminate, anhydrous calcium phosphate, citric acid, trisodium citrate, hydroxypropylcellulose, sorbitol, sorbitan fatty acid ester, polysorbate, sucrose fatty acid ester, polyoxyethylene hardened castor oil, polyvinylpyrrolidone, magnesium stearate, light silicic anhydride, talc, vegetable oil, benzyl alcohol, gum arabic, propylene glycol, polyalkylene glycol, cyclodextrin and hydroxypropylcyclodextrin, etc.

A drug formulation to be prepared as a mixture with such additives, may, for example, be a solid formulation such as a tablet, a capsule, a granule, a powder or a suppository; a liquid formulation such as a syrup, an elixir or an injection drug; and in the case of the antifungal agent, an aerosol, an ophthalmic solution, an ointment, an eye ointment, a suspension, an emulsion, a cream preparation, a liniment or a lotion, etc. These formulations can be prepared in accordance with conventional methods commonly employed in the field of drug formulations. Further, in the case of a liquid formulation, it may be of the type which is to be dissolved or suspended in water or in other suitable medium at the time of its use. Particularly, in the case of an injection drug, it may be dissolved or suspended in a physiological saline or in a glucose solution, and a buffering agent or a preserving agent may further be added.

These formulations may contain the compound of the present invention in a proportion of from 1.0 to 100 wt %, preferably from 1.0 to 60 wt % of the total amount.

These formulations may further contain therapeutically effective other compounds.

When the compound of the present invention is used as an antihyperlipemia agent, an anti-arteriosclerosis agent or an antihypercholesterolemia agent, its dose and the frequency of administration vary depending upon the sex, the age, the body weight and the diseased degree of the patient and the type and the range of the intended treating effects. However, in the case of an oral administration, it is preferred to administer from 0.01 to 20 mg/kg per day for an adult all at once or in a few times in a divided fashion. In the case of parenteral administration, it is preferred to administer from 0.001 to 2 mg/kg per day for an adult all at once or in a few times in a divided fashion.

When the compound of the present invention is used as an antifungal agent, the dose and the frequency of administration vary depending upon the sex, the age, the body weight and the diseased degree of the patient and the type and the scope of the intended treating effects. However, in the case of oral administration, it is usually preferred to administer from 0.1 to 20 mg/kg per day for an adult all at once or in a few times in a divided fashion. Further, in the case of parenteral administration, it is preferred to administer from 0.01 to 2 mg/kg per day for an adult all at once or in a few times in a divided fashion.

Now, the present invention will be described in further detail with reference to Examples and Reference Examples. However, it should be understood that the present invention is by no means restricted by such specific Examples.

EXAMPLE 1

Preparation of N-{(1RS, 2RS)-2-(4-biphenylyl)-3-(4-chlorophenyl)-1-methylpropyl}carbamoylmethylsuccinic acid 100 mg of (1RS, 2RS)-2-(4-biphenylyl)-3-(4-chlorophenyl)-1-methylpropylamine, 78 mg of di-tert-butyl carboxymethylsuccinate and 66 mg of 4-dimethylaminopyridine were dissolved in 3 ml of methylene chloride, and 52 mg of 1-ethyl-3-(3-dimethylaminopropyl)carbodiimide hydrochloride was added thereto with stirring under cooling with ice. The mixture was stirred overnight at room temperature. The reaction solution was poured into ice water and extracted by an addition of ethyl acetate. The extract solution was washed sequentially with 1N hydrochloric acid, a saturated sodium hydrogencarbonate aqueous solution and a saturated sodium chloride aqueous solution and dried over anhydrous sodium sulfate. The drying agent was separated by filtration. Then, the solvent was distilled off, and the residue was subjected to silica gel column chromatography (Wakogel™ C-200: 10g; hexane/ethyl acetate=5/1) to obtain 126 mg (yield: 77%) of a di-tert-butyl ester of the above-identified compound.

126 mg of the ester compound thus obtained was dissolved in 1 ml of methylene chloride, and 1 ml of trifluoroacetic acid was added thereto with stirring under cooling with ice. The mixture was stirred at room temperature for 2 hours. The reaction solution was concentrated under reduced pressure, and 2 ml of toluene was added to the residue. The mixture was again concentrated under reduced pressure, and the obtained residue was treated with benzene to obtain 75 mg (yield: 73%) of the above-identified compound as white crystalline powder having a melting point of from 167° to 169° C.

$^1$H-NMR(CDCl$_3$)δ: 1.01(3H, d, J=6.6 Hz), 2.47(1H, dt, J=5.6Hz, 15.1Hz), 2.60–2.95(5H, m), 3.05–3.15(1H, m), 3.20–3.30(1H, m), 4.30–4.35(1H, m), 6.92 (2H, d, J=8.3Hz), 7.13(2H, d, J=8.3Hz), 7.11(2H, d, J=7.5Hz), 7.30–736(1H, m), 7.43(1H, t, J=7.4Hz), 7.49(2H, d, J=8.0 Hz), 7.57 (2H, d, J=7.4 Hz).

Compounds of Examples 2 to 45 were prepared in the same manner in Example 1 except that (1RS, 2RS)-2-(4-biphenylyl)-3-(4-chlorophenyl)-1-methylpropylamine used as the starting material in the above reaction was changed to the corresponding amine compounds.

EXAMPLE 2

N-{(1RS, 2RS)-1-Methyl-2,3-diphenylpropyl}-carbamoylmethylsuccinic acid $^1$H-NMR(CD$_3$OD)δ: 0.90(3/2H, d, J=6.6Hz), 0.91(3/2H, d, J=6.6Hz), 2.41–2.88(6H, m), 3.11–3.30(2H, m), 4.25(1H, m), 6.88–7.25(8H, m).

EXAMPLE 3

N-{(1RS, 2RS)-2-(4-Chlorophenyl)-1-methyl-3-phenylpropyl}carbamoylmethylsuccinic acid $^1$H-NMR(CD$_3$OD)δ: 0.91(3/2H, d, J=6.8Hz), 0.92(3/2H, d, J=6.8 Hz), 2.40–2.95 (6H, m), 3.08–3.29(2H, m), 4.12–4.31(1H, m), 6.90–7.21(9H, m).

EXAMPLE 4

N-{(1RS, 2RS)-3-(4-Chlorophenyl)-1-methyl-2-phenylpropyl}carbamoylmethylsuccinic acid $^1$H-NMR(CD$_3$OD)δ0.89(3/2H, d, J=6.6 Hz), 0.90 (3/2 H, d, J=6.6Hz), 2.40–2.80(6H, m), 3.00–3.30(2H, m), 4.20(1H, m), 6.80–7.25(9H, m).

EXAMPLE 5

N-{(1RS, 2RS)-2-(4-Chlorophenyl)-1-methyl-3-(4-methylphenyl)propyl}carbamoylmethylsuccinic acid $^1$H-NMR(CDCl$_3$)δ: 0.96(3H, d, J=6.9Hz), 2.24(3H, s), 2.43(1H, ddd, J=1.7Hz, 4.8 Hz, 15.0Hz), 2.59–2.69(2H, m), 2.74–2.86(2H, m), 2.40–2.80(6H, m), 2.89–2.97(1H, m), 3.03(1H, dd, J=4.5Hz, 12.9Hz), 3.21–3.25(1H, m), 4.25–4.30(1H, m), 6.05–6.08(1H, m), 6.85(2H, d, J=7.6 Hz), 6.96(2H, d, J=8.3Hz), 7.02(2H, d, J=8.3Hz), 7.22(2H, d, J=7.6Hz).

EXAMPLE 6

N-{(1RS, 2RS)-2-(4-Chlorophenyl)-3-(4-fluorophenyl)-1-methylpropyl}carbamoylmethylsuccinic acid $^1$H-NMR(CDCl$_3$)δ: 0.96(3H, d, J=7.0Hz), 2.40–2.55(1H, m), 2.60–2.90(5H, m), 3.07(1H, d, J=11.4Hz), 3.20–3.30(1H, m), 4.27(1H, quint., J=7.0Hz), 6.78–6.90(5H, m), 6.98(2H, d, J=8.2Hz), 7.21(2H, d, J=8.2Hz).

EXAMPLE 7

N-{(1RS, 2RS)-3-(4-Biphenylyl)-2-(4-chlorophenyl)-1-methylpropyl}carbamoylmethylsuccinic acid $^1$H-NMR(CDCl$_3$)δ: 0.93(3H, d, J=6.7Hz), 2.33–2.47(1H, m), 2.55–2.99(5H, m), 3.01–3.13(1H, m), 3.18–3.32(1H, m), 4.18–4.36(1H, m), 6.12(1H, br.), 6.88–7.03(4H, m), 7.12–7.21(2H, m), 7.22–7.30(1H, m), 7.31–7.42(4H, m), 7.43–7.52(2H, m).

EXAMPLE 8

N-{(1RS, 2RS)-2-(4-Chlorophenyl)-3-(3-chlorophenyl)-1-methylpropyl}carbamoylmethylsuccinic acid $^1$H-NMR(CDCl$_3$)δ: 0.96(3H, d, J=6.4Hz), 2.45(1H, dd, J=4.5Hz, 15.5Hz), 2.64–2.83(4H, m), 2.87–2.95(1H, m), 3.06(1H, dd, J=4.1Hz, 13.3Hz), 3.24–3.31(1H, m), 4.29(1H, quint., J=2.6Hz), 6.11(1H, t, J=9.5Hz), 6.75–6.77(1H, m), 6.96–6.99(3H, m), 7.02–7.05(2H, m), 7.21(2H, d, J=7.8 Hz).

EXAMPLE 9

N-{(1RS, 2RS)-2-(4-Chlorophenyl)-3-(2-chlorophenyl)-1-methylpropyl}carbamoylmethylsuccinic acid $^1$H-NMR(CDCl$_3$)δ: 0.97(3/2H, d, J=6.6Hz), 0.98(3/2H, d, J=6.6Hz), 2.50(1H, dd, J=5.0Hz, 15.5Hz), 2.65–2.84(4H, m), 2.89–2.98(1H, m), 3.26–3.34(2H, m), 4.32–4.40(1H, m), 6.08(1H, br.), 6.68(1H, dt, J=2.0Hz, 7.9Hz), 6.91–7.06(2H, m), 6.97(2H, d, J=8.3Hz), 7.19(2H, d, J=8.3Hz), 7.23–7.27(1H, m).

EXAMPLE 10

N-{(1RS, 2RS)-2-(4-Chlorophenyl)-3-(4-methoxyphenyl)-1-methylpropyl}carbamoylmethylsuccinic acid $^1$H-NMR(CDCl$_3$)δ: 0.86–0.92(3H, m), 2.40(1H, dd, J=4.2Hz, 15.5Hz), 2.63–3.03(6H, m), 3.03–3.27(1H, m), 3.70(1H, s), 4.20–4.31(1H, m), 5.93(1H, t, J=7.8 Hz), 6.68(2H, dd, J=1.7Hz, 8.5Hz), 6.99(2H, d, J=8.1Hz), 7.21(2H, d, J=8.1Hz).

EXAMPLE 11

N-{(1RS, 2RS)-2-(4-Chlorophenyl)-1-methyl-3-(1-naphthyl)propyl}carbamoylmethylsuccinic acid $^1$H-NMR(CD$_3$OD)δ: 0.96(3/2H, d, J=6.0Hz), 0.97(3/2H, d, J=6.0Hz), 2.48–2.83(4H, m), 3.06–3.12(2H, m), 3.26–3.28(1H, m), 3.77(1H, dd, J=9.0Hz, 14.5Hz), 4.35–4.42(1H, m), 6.87(1H, d, J=7.5Hz), 6.97(2H, d, J=7.5Hz), 7.11 (1H, d, J=7.5Hz), 7.13(2H, d, J=6.0Hz), 7.40–7.53(2H, m), 7.58(1H, d, J=8.5Hz), 7.78(1H, d, J=8.5 Hz), 8.09(1H, d, J=8.5Hz).

EXAMPLE 12

N-{(1RS, 2RS)-2-(4-Chlorophenyl)-1-methyl-3-(2-naphthyl)propyl}carbamoylmethylsuccinic acid $^1$H-NMR(CDCl$_3$)δ: 0.92(3H, d, J=6.0Hz), 2.20–2.45(2H, m), 2.46–2.82(2H, m), 2.83–3.08(2H, m), 3.09–3.30(2H, m), 4.20–4.35(2H, m), 4.50–5.50(2H, br.), 6.25(1H, br.), 6.92 (2H, s), 7.08–7.20(3H, m), 7.34(3H, s), 7.48–7.75(3H, m).

EXAMPLE 13

N-{(1RS, 2RS)-3-(4-Chlorophenyl)-1-methyl-2-(4-methylphenyl)propyl}carbamoylmethylsuccinic acid $^1$H-NMR(CDCl$_3$)δ: 0.96(3H, d, J=6.9Hz), 2.29(3H, s), 2.44(1H, dt, J=5.0Hz, 15.0Hz), 2.50–2.90(5H, m), 2.98–3.09(1H, m), 3.19–3.29(1H, m), 4.27(1H, dq, J=3.3Hz, 6.6Hz), 6.89(2H, d, J=8.3Hz), 6.94(2H, d, J=8.1Hz), 7.05(2H, d, J=8.1Hz), 7.09(2H, d, J=8.3Hz).

EXAMPLE 14

N-{(1RS, 2RS)-2-(4-Bromophenyl)-3-(4-chlorophenyl)-1-methylpropyl}carbamoylmethylsuccinic acid $^1$H-NMR(CDCl$_3$)δ: 0.94(2H, d, J=6.6Hz), 2.47(1H, dt, J=5.6Hz, 15.2Hz), 2.62–2.82(5H, m), 3.07(1H, dd, J=3.0Hz, 10.0Hz), 3.24(1H, dt, J=6.3Hz, 13.1Hz), 4.25(1H, q, J=6.6Hz), 6.85(2H, d, J=8.3Hz), 6.92(2H, d, J=8.0Hz), 7.09(2H, d, J=8.3Hz), 7.36(2H, d, J=8.0Hz).

EXAMPLE 15

N-{(1RS, 2RS)-2-(4-tert-Butylphenyl)-3-(4-chlorophenyl)-1-methylpropyl}carbamoylmethylsuccinic acid $^1$H-NMR(CDCl$_3$)δ: 0.96(3H, d, J=6.6Hz), 1.28(9H, s), 2.45(1H, dt, J=5.0Hz, 14.9Hz), 2.59–2.89(5H, m), 2.98–3.08(1H, m), 3.20–3.30(1H, m), 4.25 (1H, q, J=6.6Hz), 6.89(2H, d, J=8.3Hz), 6.97(2H, d, J=8.3Hz), 7.08 (2H, d, J=7.4Hz), 7.25(2H, d, J=8.1Hz).

EXAMPLE 16

N-{(1RS, 2RS)-3-(4-Chlorophenyl)-2-(4-methoxyphenyl)-1-methylpropyl}carbamoylmethylsuccinic acid $^1$H-NMR(CDCl$_3$+CD$_3$OD)δ: 0.94(3H, d, J=6.6Hz), 2.45(1H, dt, J=6.0 Hz, 15.0Hz), 2.60–2.80(5H, m), 3.00–3.10(1H, m), 3.20–3.28 (1H, m), 3.78(3H, s), 4.20–4.28(1H, m), 6.78(2H, d, J=8.5 Hz), 6.86(2H, d, J=8.2Hz), 6.96(2H, d, J=8.5Hz), 7.08(2H, d, J=8.2Hz).

EXAMPLE 17

N-{(1RS, 2RS)-2-(3-Chlorophenyl)-3-(4-chlorophenyl)-1-methylpropyl}carbamoylmethylsuccinic acid $^1$H-NMR(CDCl$_3$)δ: 0.99(3H, d, J=6.5Hz), 2.43(1H, d, J=5.2Hz), 2.67–2.90(5H, m), 3.04(1H, dd, J=3.9Hz, 13.2Hz), 3.25–3.32(1H, m), 4.30(1H, q, J=6.7Hz), 5.94(1H, br.), 6.86–6.91(3H, m), 7.06(1H, s), 7.09–7.13(2H, m), 7.18(2H, d, J=3.5Hz).

EXAMPLE 18

N-{(1RS, 2RS)-3-(4-Chlorophenyl)-1-methyl-2-(1-naphthyl)propyl}carbamoylmethylsuccinic acid $^1$H-NMR(CDCl$_3$)δ: 0.94(3H, d, J=5.9Hz), 2.31–2.35(1H, m), 2.55–2.79(3H, m), 2.99–3.03(1H, m), 3.16–3.28(2H, m), 4.02–4.10(1H, m), 4.40–4.45(1H, m), 6.20–6.30(1H, m), 6.85(2H, d, J=8.0Hz), 6.87(2H, d, J=7.7Hz), 6.93(2H, d, J=7.7Hz), 6.95(2H, d, J=8.0Hz), 7.33–7.42(4H, m), 7.65–7.68(1H, m), 7.73–7.76(1H, m), 7.86–7.89(1H, m).

EXAMPLE 19

N-{(1RS, 2RS)-3-(4-Chlorophenyl)-1-methyl-2-(2-naphthyl)propyl}carbamoylmethylsuccinic acid $^1$H-NMR(CDCl$_3$)δ: 0.98(3H, d, J=6.6Hz), 2.40–2.50(1H, m), 2.56–2.86(3H, m), 2.92–3.16(3H, m), 3.24–3.36(1H, m), 4.39(1H, dq, J=7.1Hz, 14.1Hz), 6.10(1H, br.), 6.86(2H, br.d, J=8.0Hz), 7.01(1H, d, J=8.0Hz), 7.03(1H, d, J=8.0Hz), 7.23(2H, br.d, J=9.3Hz), 7.40–7.45 (3H, m), 7.68–7.79(3H, m).

EXAMPLE 20

N-{(1RS, 2RS)-3-(4-Chlorophenyl)-2-(4-hydroxyphenyl)-1-methylpropyl}carbamoylmethylsuccinic acid ¹H-NMR(CDCl₃)δ: 0.96(3H, d, J=6.3Hz), 2.44(1H, dt, J=4.8Hz, 14.6Hz), 2.60–2.86(5H, m), 2.96–3.06(1H, m), 3.18–3.28(1H, m), 4.16–4.26(1H, m), 6.71(2H, d, J=8.0Hz), 6.89(4H, d, J=8.4Hz), 7.08(2H, d, J=7.1Hz).

EXAMPLE 21

N-{(1RS, 2RS)-2-(4'-Chloro-4-biphenylyl)-3-(4-chlorophenyl)-1-methylpropyl}carbamoylmethylsuccinic acid ¹H-NMR(CDCl₃)δ: 0.99(3H, d, J=6.5Hz), 2.47(1H, dt, J=6.1Hz, 14.9Hz), 2.60–3.14(6H, m), 3.20–3.30(1H, m), 4.26–4.35(1H, m), 6.90(2H, d, J=8.4Hz), 7.14–7.19(4H, m), 7.39(2H, d, J=8.4Hz), 7.45(2H, d, J=7.3Hz), 7.50(2H, d, J=8.8Hz).

EXAMPLE 22

N-[(1RS, 2RS)-3-(4-Chlorophenyl)-1-methyl-2-{4-(3-thienyl)phenyl}propyl]carbamoylmethylsuccinic acid ¹H-NMR(CDCl₃)δ: 0.99(3H, d, J=6.6Hz), 2.43–2.88(6H, m), 3.04–3.14(1H, m), 3.20–3.30(1H, m), 4.26–4.36(1H, m), 6.90(2H, d, J=8.3Hz), 7.08(2H, d, J=8.3Hz), 7.09(2H, d, J=8.3 Hz), 7.30–7.40(2H, m), 7.44(1H, t, J=2.0Hz), 7.49(2H, d, J=8.3Hz).

EXAMPLE 23

N-[(1RS, 2RS)-3-(4-Chlorophenyl)-1-methyl-2-{4-(3-pyridyl)phenyl}propyl]carbamoylmethylsuccinic acid trifluoroacetate ¹H-NMR(CDCl₃)δ: 1.02(3H, d, J=6.9Hz), 2.47(1H, dt, J=5.5Hz, 15.4Hz), 2.60–2.96(3H, m), 3.00–3.16(2H, m), 3.18–3.28(1H, m), 4.28–4.38(1H, m), 6.93(2H, d, J=8.3Hz), 6.94(2H, d, J=8.0Hz), 7.09(2H, d, J=8.5Hz), 7.10(2H, d, J=8.6Hz), 7.24(2H, d, J=7.4Hz), 7.52(2H, d, J=8.3Hz), 7.53(2H, d, J=8.3Hz), 7.68–7.74(1H, m), 8.22–8.30(1H, m), 8.66(1H, d, J=4.9Hz), 9.00(1H, d, J=9.1Hz).

EXAMPLE 24

N-{(1RS, 2RS)-2-(3'-Chloro-4-biphenylyl)-3-(4-chlorophenyl)-1-methylpropyl}carbamoylmethylsuccinic acid ¹H-NMR(CDCl₃)δ: 0.99(3H, d, J=6.5Hz), 2.43–2.52(1H, m), 2.60–2.95(5H, m), 3.08–3.13(1H, m), 3.20–3.30(1H, m), 6.90(2H, d, J=8.3Hz), 7.08–7.15(4H, m), 7.29(1H, dt, J=1.7Hz, 7.5Hz), 7.35(1H, t, J=7.5Hz), 7.42–7.47(3H, m), 7.55(1H, t, J=1.7Hz).

EXAMPLE 25

N-{(1RS, 2RS)-2-(4-Chlorophenyl)-3-(3,4-dichlorophenyl)-1-methylpropyl}-carbamoylmethylsuccinic acid ¹H-NMR(CDCl₃)δ: 0.93(3H, d, J=6.5Hz), 2.40–2.55(1H, m), 2.60–2.91(5H, m), 2.98–3.10(1H, m), 3.20–3.36(1H, m), 4.15–4.32(1H, m), 6.51(1H, br.), 6.63–6.70(1H, m), 6.94(2H, d, J=8.2Hz), 7.05(1H, br.t, J=2.1Hz), 7.10–7.16(1H, m), 7.20(1H, d, J=8.2Hz).

EXAMPLE 26

N-{(1 RS, 2RS)-3-(4-Chlorophenyl)-2-(3,4-dichlorophenyl)-1-methylpropyl}-carbamoylmethylsuccinic acid ¹H-NMR(CDCl₃)δ: 0.95(3H, d, J=6.4Hz), 2.41–2.47(1H, m), 2.59–2.78(4H, m), 2.82–2.88(1H, m), 3.00–3.07(1H, m), 3.23–3.31(1H, m), 4.19–4.25(1H, m), 6.30–6.35(1H, m), 6.85(3H, dd, J=3.0Hz, 8.5Hz), 7.09(2H, dd, J=2.8 Hz, 8.5Hz), 7.14(1H, s), 7.29(1H, d, J=8.3Hz).

EXAMPLE 27

N-{(1RS, 2RS)-2-(3-Bromophenyl)-3-(4-chlorophenyl)-1-methylpropyl}carbamoylmethylsuccinic acid ¹H-NMR(CD₃OD)δ: 0.91(3/2H, d, J=6.6Hz), 0.92(3/2H, d, J=6.6Hz), 2.43–2.88(6H, m), 3.11–3.30(2H, m), 4.20(1H, m), 6.89(2H, d, J=8.1Hz), 7.02–7.20(4H, m), 7.24(1H, br.), 7.30(1H, br.d, J=7.8Hz).

EXAMPLE 28

N-{(1RS, 2RS)-2-(3-Biphenylyl)-3-(4-chlorophenyl)-1-methylpropyl}carbamoylmethylsuccinic acid ¹H-NMR(CD₃OD)δ: 0.95(3/2H, d, J=9.9Hz), 0.97(3/2H, d, J=9.9Hz), 2.40–2.97(6H, m), 3.15–3.30(2H, m), 4.30(1H, m), 6.90(2H, d, J=12.6Hz), 7.02–7.10(3H, m), 7.22–7.51(8H, m).

EXAMPLE 29

N-{(1RS, 2RS)-2-(4-Chlorophenyl)-3-(3,4-difluorophenyl)-1-methylpropyl}carbamoylmethylsuccinic acid ¹H-NMR(CDCl₃)δ: 0.95(3H, d, J=6.7Hz), 2.43–2.50(1H, m), 2.64–2.89(5H, m), 3.02–3.07(1H, m), 3.24–3.33(1H, m), 4.22–4.30(1H, m), 6.19(1H, m), 6.55–6.59(1H, m), 6.74–7.80(1H, m), 6.83–6.93(1H, m), 6.96(2H, d, J=8.3Hz), 7.21(2H, d, J=8.3Hz).

EXAMPLE 30

N-{(1RS, 2RS)-2-(4-Biphenylyl)-3-(3,4-dichlorophenyl)-1-methylpropyl}carbamoylmethylsuccinic acid ¹H-NMR(CDCl₃)δ: 1.02(3H, d, J=6.6Hz), 2.43–2.54(1H, m), 2.55–2.98(5H, m), 3.01–3.11(1H, m), 3.25–3.40(1H, m), 4.27–4.40(1H, m), 6.13–6.28(1H, m), 6.70–6.79(1H, m), 7.07–7.09(3H, m), 7.14(1H, dd, J=3.3Hz, 7.8 Hz), 7.32(1H, m), 7.40 (2H, m), 7.47(2H, d, J=7.8 Hz), 7.54(2H, m).

EXAMPLE 31

N-[(1RS, 2RS)-2-(4-Chlorophenyl)-1-methyl-3-{3-(3-thienyl)phenyl}propyl]carbamoylmethylsuccinic acid $^1$H-NMR(CDCl$_3$)δ: 0.93(3H, d, J=6.4Hz), 2.35–2.40(1H, m), 2.59–2.92(5H, m), 3.05–3.09(1H, m), 3.21–3.28(1H, m), 4.25–4.30(1H, m), 6.16–6.19(1H, m), 6.81–6.85(1H, m), 6.96(2H, d, J=7.5Hz), 7.11–7.15(2H, m), 7.18(2H, d, J=7.5Hz), 7.20–7.24(1H, m), 7.28–7.32(3H, m).

EXAMPLE 32

N-{(1RS, 2RS)-2-(4-Biphenylyl)-1-methyl-3-(2-naphthyl)propyl}carbamoylmethylsuccinic acid $^1$H-NMR(CDCl$_3$+CD$_3$OD)δ: 1.03(3H, d, J=6.9Hz), 2.40–2.50(1H, m), 2.60–2.80(3H, m), 3.00–3.15(2H, m), 3.20–3.35(2H, m), 4.30–4.40(1H, m), 7.10–7.80(16H, m).

EXAMPLE 33

N-[(1RS, 2RS)-3-(4-Chlorophenyl)-1-methyl-2-{4-(2-naphthyl)phenyl}propyl]carbamoylmethylsuccinic acid $^1$H-NMR(CDCl$_3$)δ: 1.02(3H, d, J=6.9Hz), 2.46(1/2H, J=5.9Hz), 2.51(1/2H, t, J=5.9Hz), 2.60–2.84(3H, m), 2.86–3.00 (2H, m), 3.06–3.18(1H, m), 3.21–3.32(1H, m), 4.29–4.39 (1H, m), 6.94(2H, d, J=8.6Hz), 7.11(2H, br.d), J=8.2Hz), 7.17(2H, d, J=8.4Hz), 7.62(2H, d, J=8.3 Hz), 7.45–7.54(2H, m), 7.72(1H, dd, J=1.6Hz, 8.5Hz), 7.84–7.92(3H, m), 8.20(1H, d, J=1.4Hz).

EXAMPLE 34

N-{(1RS, 2RS)-2-(4-Biphenylyl)-3-(4-chlorophenyl)-1-methylpropyl}-N-methylcarbamoylmethylsuccinic acid $^1$H-NMR(CDCl$_3$+CD$_3$OD)δ: 0.90–1.07(3H, m), 2.60–3.00(11H, m), 4.15–4.25 and 5.00–5.20(total 1H, m), 6.63–6.71(1H, m), 6.93–7.01(1H, m), 7.10–7.20(3H, m), 7.30–7.65(7H, m).

EXAMPLE 35

N-{(1RS, 2RS)-3-(4-Chlorophenyl)-2-(2-fluoro-4-biphenylyl)-1-methylpropyl}-carbamoylmethylsuccinic acid $^1$H-NMR(CDCl$_3$)δ: 1.01(3/2H, d, J=6.5 Hz), 1.02(3/2H, d, J=6.5 Hz), 2.45(1/2H, t, J=5.9Hz), 2.50(1/2H, t, J=5.9Hz), 2.61–2.96(5H, m), 3.00–3.18(1H, m), 3.20–3.31(1H, m), 4.24–4.34(1H, m), 6.86–6.95(2H, m), 6.93(2H, d, J=8.5Hz), 7.11(1H, d, J=7.0Hz), 7.12(1H, d, J=7.0Hz), 7.29–7.38(2H, m), 7.39–7.46(2H, m), 7.50–7.54(2H, m).

EXAMPLE 36

N-[(1RS, 2RS)-3-(4-Chlorophenyl)-2-{4-(2-furyl)phenyl}-1-methylpropyl]carbamoylmethylsuccinic acid $^1$H-NMR(CDCl$_3$)δ:0.97(3/2H, d, J=6.5Hz), 0.98(3/2H, d, J=6.5Hz), 2.43–2.90(6H, m), 3.20–3.30(1H, m), 4.25–4.35(1H, m), 6.46(1H, dd, J=1.6Hz, 3.5Hz), 6.61(1H, d, J=3.5Hz), 6.88(2H, d, J=8.6Hz), 7.05–7.10(4H, m), 7.55(2H, d, J=8.3Hz), 7.45(1H, d, J=1.6Hz).

EXAMPLE 37

N-{(1RS, 2RS)-2-(4-Chlorophenyl)-1-methyl-3-(4-pyridyl)propyl}carbamoyl-methylsuccinic acid trifluoroacetate $^1$H-NMR(CD$_3$OD)δ: 0.94(3/2H, d, J=6.8 Hz), 0.97(3/2H, d, J=6.8Hz), 2.40–2.80(4H, m), 3.00–3.30(3H, m), 3.40–3.60(1H, m), 4.15–4.30(1H, m), 7.13(2H, dd, J=1.3Hz, 8.6Hz), 7.25(2H, d, J=8.6Hz), 7.50–7.60(1H, m), 7.63(2H, d, J=6.4Hz), 8.53(2H, d, J=6.4Hz).

EXAMPLE 38

N-{(1RS, 2RS)-2-(4-Chlorophenyl)-3-(5-chloro-2-thienyl)-1-methylpropyl}-carbamoylmethylsuccinic acid $^1$H-NMR(CD$_3$OD)δ: 0.89(3/2H, d, J=6.6Hz), 0.91(3/2H, d, J=6.6Hz), 2.40–3.05(7H, m), 3.20–3.30(1H, m), 4.10–4.20(1H, m), 6.36(1/2H, d, J=3.6Hz), 6.37(1/2H, d, J=3.6Hz), 6.56(1/2H, d, J=3.6Hz), 6.58(1/2H, d, J=3.6Hz), 7.12(1H, d, J=8.7Hz), 7.13(1H, d, J=8.7Hz), 7.27(2H, d, J=8.7Hz).

EXAMPLE 39

N-{(1RS, 2RS)-2-(4-Chlorophenyl)-1-methyl-3-(8-quinolyl)propyl}carbamoylmethylsuccinic acid trifluoroacetate $^1$H-NMR(CD$_3$OD)δ: 0.98(3/2H, d, J=6.6Hz), 1.00(3/2H, d, J=6.6Hz), 2.45–2.82(5H, m), 3.30–3.70(2H, m), 3.80–4.00(1H, m), 4.20–4.40(1H, m), 6.95–7.20(4H, m), 7.45–7.60 (2H, m), 7.75–7.95(2H, m), 8.65–8.80(1H, m), 9.03 (1 H, dd, J=1.7Hz, 4.9Hz).

EXAMPLE 40

N-{(1RS, 2RS)-3-(7-Benzo[b]thienyl)-2-(4-chlorophenyl)-1-methylpropyl}-carbamoylmethylsuccinic acid $^1$H-NMR(CD$_3$OD)δ: 0.95(3H, d, J=6.8 Hz), 2.40–2.80(4H, m), 3.00–3.50(4H, m), 4.20–4.40(1H, m), 6.79.(1H, t, J=6.6Hz), 7.00–7.22(5H, m), 7.29(1/2H, d, J=5.5Hz), 7.30(1/2H, d, J=5.5Hz), 7.46(1/2H, d, J=5.5Hz), 7.47(1/2H, d, J=5.5Hz), 7.55(1H, d, J=8.0Hz).

EXAMPLE 41

N-{(1RS, 2RS)-3-(4-Chlorophenyl)-1-methyl-2-(3',4'-methylenedioxy-4-biphenylyl)-propyl}carbamoylmethyl, succinic acid $^1$H-NMR(CDCl$_3$)δ: 0.99(3/2H, d, J=6.9Hz), 1.00(3/2H, d, J=6.9Hz), 2.44(1/2H, t, J=6.1Hz), 2.49(1/2H, t, J=6.9Hz), 2.61–2.89(6H, m), 3.04–3.30(2H, m), 4.24–4.36(1H, m), 5.99(2H, s), 6.85–6.88(1H, m), 7.02–7.05(2H, m), 6.91(2H, d, J=8.6Hz), 7.08–7.19(4H, m), 7.40(2H, d, J=8.6Hz).

EXAMPLE 42

N-{(1RS, 2RS)-2-(5-Benzo[b]thienyl)-3-(4-chlorophenyl)-1-methylpropyl}carbamoylmethylsuccinic acid $^1$H-NMR(CD$_3$OD)δ: 0.90(3/2H, d, J=6.7Hz), 0.93(3/2H, d, J=6.7Hz), 3.10–3.30(2H, m), 4.20–4.40(1H, m), 6.84(2H, d, J=8.4Hz), 6.90–7.22(4H, m), 7.25(1/2H, d, J=5.4Hz), 7.26(1/2H, d, J=5.4Hz), 7.48(1H, d, J=5.4Hz), 7.50(1H, s), 7.76(1H, d, J=8.3Hz).

EXAMPLE 43

N-{(1RS, 2RS)-3-(4-Chlorophenyl)-2-(2'-fluoro-4-biphenylyl)-1-methylpropyl}-carbamoylmethylsuccinic acid $^1$-NMR(CDCl$_3$+CD$_3$OD)δ: 1.01(3H, d, J=6.5Hz), 2.47(1H, dt, J=6.0Hz, 15.1Hz), 2.61–2.70(2H, m), 2.77(1H, dt, J=6.8Hz, 17.2Hz), 2.85–3.13(3H, m), 3.20–3.30(1H, m), 4.26–4.36(1H, m), 6.93(2H, d, J=8.3Hz), 7.11(2H, d, J=8.6Hz), 7.14(2H, d, J=8.1Hz), 7.18(1H, d, J=8.0Hz), 7.21(1H, d, J=7.6Hz), 7.28–7.35(1H, m), 7.40–7.46(1H, m), 7.45(2H, d, J=6.8 Hz).

EXAMPLE 44

N-{(1RS, 2RS)-3-(4-Chlorophenyl)-2-(2'-methoxy-4-biphenylyl)-1-methylpropyl}carbamoylmethylsuccinic acid $^1$H-NMR(CDCl$_3$)δ: 1.02(3H, d, J=6.5Hz), 2.45(1H, dt, J=5.9Hz, 15.1Hz), 2.59–2.71(2H, m), 2.76(1H, dr, J=7.4Hz, 17.1Hz), 2.89–3.10(3H, m), 3.81(3H, s), 4.26–4.36(1H, m), 6.96(2H, d, J=8.2Hz), 7.01(2H, d, J=7.3Hz), 7.03(1H, d, J=6.6Hz), 7.11(2H, d, J=8.2Hz), 7.29–7.34(2H, m), 7.43 (2H, d, J=8.3Hz).

EXAMPLE 45

N-[(1RS, 2RS)-3-(3,4-Dichlorophenyl)-1-methyl-2-{4-(5-oxazolyl)phenyl}propyl]carbamoyl-methylsuccinic acid $^1$H-NMR(CD$_3$OD)δ: 0.94(3/2H, d, J=6.6Hz), 0.95(3/2H, d, J=6.6Hz), 2.40–3.00(6H, m), 3.10–3.30(2H, m), 4.20–4.35(1H, m), 6.85(1H, d, J=8.3Hz), 7.10–7.25(4H, m), 7.45(1H, s), 7.62(2H, d, J=8.3Hz), 7.20(1H, s).

EXAMPLE 46

Preparation of (2S)- and (2R)-2-[N-{(1S, 2S)-2-(4-biphenylyl)-3-(4-chlorophenyl)-1-methylpropyl}-carbamoylmethyl]succinic acid 112 mg of (1S, 2S)-2-(4-biphenylyl)-3-(4-chlorophenyl)-1-methylpropylamine obtained in Example 114, 170 mg of dibenzhydryl carboxymethylsuccinate and 41 mg of 4-dimethylaminopyridine were dissolved in 2 ml of methylene chloride, and 41 mg of 1-ethyl-3-(3-dimethylaminopropyl)carbodiimide hydrochloride was added thereto with stirring under cooling with ice. The mixture was stirred at room temperature overnight. The reaction solution was developed in a column packed with 5 g of silica gel, and the column was washed with ethyl acetate. Then, eluates were put together and evaporated to dryness under reduced pressure. The residue was subjected to medium pressure liquid chromatography (Lobar column™, size B, Lichroprep™ Si60F, manufactured by Merck Co.); hexane/ethyl acetate=10/1), whereby two types of products which are diastereomers to each other were separated and purified to obtain the above-identified two compounds in the form of the respective dibenzhydryl esters in an amount of 92 mg (yield: 33%) as the first eluate component and 77 mg (yield: 28%) as the later eluate component.

Of the two types of dibenzhydryl esters thus obtained, 92 mg of the compound obtained as the first eluate component by the medium liquid chromatography treatment was dissolved in 1 ml of chloroform together with 20 mg of anisole, and 1 ml of trifluoroacetic acid was added thereto with stirring under cooling with ice. The mixture was stirred at room temperature for one hour. The reaction solution was evaporated to dryness under reduced pressure, and the residue was treated with benzene, to obtain 49 mg (yield: 89%) of the above identified compound with the absolute configuration at the 2-position of succinic acid being S, as white crystalline powder having a melting point of from 186° to 188° C. and $[\alpha]_D^{20}$=+135.7° (c=1.0, methanol).

$^1$H-NMR(CDCl$_3$+CD$_3$OD)δ: 0.99(3H, d, J=5.5Hz), 2.45(1H, dd, J=6.1Hz, 14.8Hz), 2.58–2.79(3H, m), 2.80–2.92(2H, m), 3.01–3.18(1H, m), 3.20–3.32(1H, m), 4.24–4.36(1H, m), 6.90(2H, d, J=8.2Hz), 7.09(2H, d, J=8.3Hz), 7.12(2H, d, J=8.0Hz), 7.29–7.36(1H, m), 7.39–7.45(2H, m), 7.47(2H, d, J=8.3Hz), 7.55–7.59(2H, m).

Likewise, using the later eluate component (77 mg) obtained by the medium liquid chromatography treatment, as the starting material dibenzhydryl ester, the same reaction as above was carried out to obtain 39 mg (yield: 85%) of the above identified compound with the absolute configuration at the 2-position of succinic acid being R, as white crystalline powder having a melting point of from 191° to 193° C. and $[\alpha]_D^{20}$=+129.3° (c=0.5, methanol).

EXAMPLE 47

Preparation of (2S)-2-[N-{(1S, 2S)-2-(4-biphenylyl)-3(3,4-dichlorophenyl)-1-methylpropyl}-carbamoylmethyl]succinic acid 5.33 g of (1S, 2S)-2-(4-biphenylyl)-3-(3,4-dichlorophenyl)-1-methylpropylamine obtained in Example 115, 3.78 g of di-tert-butyl (2S)-carboxymethylsuccinate obtained in Example 116 and 3.84 g of 4-dimethylaminopyridine were dissolved in 75 ml of methylene chloride, and 3.01 g of 1-ethyl-3-(3-dimethylaminopropyl)carbodiimide hydrochloride was added thereto with stirring under cooling with ice. The mixture was stirred at room temperature for 12 hours. The reaction solution was diluted with methylene chloride, then sequentially washed with 1N hydrochloric acid, a saturated sodium hydrogencarbonate aqueous solution and a saturated sodium chloride aqueous solution and dried over anhydrous magnesium sulfate. The drying agent was separated by filtration, and then the solvent was distilled off under reduced pressure. The residue was dissolved in 8 ml of methylene chloride, and then 230 ml of hexane was added thereto, whereupon the precipitate was collected by filtration to obtain 7.54 g (yield: 90%) of a di-tert-butyl ester of the above-identified compound.

7.54 g of the ester compound thus obtained was dissolved in 25 ml of methylene chloride, and 50 ml of trifluoroacetic acid was added thereto with stirring under cooling with ice. The mixture was stirred at room temperature for 20 hours. The reaction solution was concentrated under reduced pressure, and then 30 ml of toluene was added to the residue. Concentration under reduced pressure was again repeated, and the obtained residue was recrystallized from a solvent mixture comprising 12 ml of methanol, 65 ml of methylene chloride and 290 ml of hexane to obtain 4.95 g (yield: 79%) of the above-identified compound as white crystalline powder having a melting point of from 176° to 177° C. and $[\alpha]_D^{20}$=+129° (c=1.0, methanol).

¹H-NMR(CD₃OD)δ: 0.98(3H, d, J=6.5Hz), 2.54(1H, dd, J=7.0Hz, 15.5Hz), 2.62(1H, dd, J=5.8 Hz, 17.0Hz), 2.69(1H, dd, J=7.0Hz, 15.5Hz), 2.74(1H, dd, J=7.5Hz, 17.0Hz), 2.78–2.92(2H, m), 3.17(1H, br.d, J=9.9Hz), 3.23–3.27(1H, m), 4.25(1H, dq, J=6.5Hz, 9.0Hz), 6.86(1H, dd, J=2.1Hz, 8.4Hz), 7.11(1H, d, J=2.1Hz), 7.15(2H, d, J=8.3Hz), 7.21(1H, d, J=8.4Hz), 7.25–7.32(1H, m), 7.36–7.42(2H, m), 7.51(2H, d, J=8.3Hz), 7.54–7.58(2H, m).

Compounds of Examples 48 to 51 were prepared in the same manner as in Example 47 except that (1S, 2S)-2-(4-biphenylyl)-3-(3,4-dichlorophenyl)-1-methylpropylamine used as the starting material in the above reaction was changed to the corresponding optically active amine compounds.

EXAMPLE 48

(2S)-2-[N-{(1S, 2S)-3-(3,4-Dichlorophenyl)-2-(2-fluoro4-biphenylyl)-1-methylpropyl}-carbamoylmethyl]succinic acid mp 170°–171° C.

¹H-NMR(CD₃OD)δ: 0.99(3H, d, J=6.9 Hz), 2.53(1H, dd, J=6.9 Hz, 15.6 Hz), 2.61(1H, dd, J=6.0 Hz, 17.1 Hz), 2.69(1H, dd, J=6.9 Hz, 15.6 Hz), 2.74(1H, dd, J=7.5 Hz, 17.1 Hz), 2.82(1H, dd, J=11.7 Hz, 12.6 Hz), 3.12–3.28(1H, m), 4.23(1H, dq, J=6.9 Hz, 8.7 Hz), 6.91(1H, dd, J=1.8 Hz, 8.1 Hz), 6.95(1H, s), 6.99(1H, s), 7.16(1H, d, J=1.8 Hz), 7.26(1H, d, J=7.8 Hz), 7.29–7.43(4H, m), 7.46–7.51(2H, m).

EXAMPLE 49

(2S)-2-[N-{(1S, 2S)-2-(4-Biphenylyl)-3-(3,4-dichlorophenyl)-1-methylpropyl}-N-methylcarbamoylmethyl]succinic acid mp 166.5°–167.5° C.

¹H-NMR(CD₃OD)δ: 0.92–1.04(3H, m), 2.64–3.12(10H, m), 3.39–3.41(1H, m) 4.12–4.23, 5.00–5.18(total 1H, m), 6.62–6.70(1H, m), 6.93–7.02(1H, m), 7.09–7.19(3H, m), 7.29–7.38(1H, m) 7.39–7.54(4H, m), 7.55–7.60(2H, m).

EXAMPLE 50

(2S)-2-[N-Benzyl-N-{(1S, 2S)-2-(2-fluoro-4-biphenylyl)-3(3,4-dichlorophenyl)-1-methylpropyl}carbamoylmethyl]succinic acid mp 105°–107° C.

¹H-NMR(CDCl₃)δ: 0.96–1.08(3H, m), 2.50–3.00(6H, m), 3.12–3.60(2H, m), 4.17–4.20(1H, m), 4.51(2H, s), 6.15(1/4H, dd, J=1.5 Hz, 8.1 Hz), 6.27(1/4H, d, J=1.5 Hz), 6.61(3/4H, dd, J=1.5 Hz, 8.1 Hz), 6.76–6.92(11/4H, m), 7.02(1/4H, d, J=8.1 Hz), 7.14(3/4H, d, J=8.1 Hz), 7.24–7.45(9H, m), 7.47–7.53(2H, m).

EXAMPLE 51

(2S)-2-[N-{(1S, 2S)-3-(3,4-Dichlorophenyl)-2-(2-fluoro-4-biphenylyl)-1-methylpropyl}-N-methylcarbamoylmethyl]succinic acid mp 165°–166° C.

¹H-NMR(CD₃OD)δ: 0.92–1.08(3H, m), 2.63–3.14(7H, m), 2.85–2.95(3H, m), 4.12–5.15(1H, m), 6.69–6.75(1H, m), 6.90–7.03(3H, m), 7.20(1H, d, J=8.4 Hz), 7.30–7.48(4H, m), 7.50–7.57(2H, m).

EXAMPLE 52

Preparation of (2S)-2-[N-{(1S, 2S, 3E)-2-(3,4-dichlorobenzyl)-1-methyl-4-(2-naphthyl)-3-butenyl}carbamoylmethyl]succinic acid 633 mg of (1S, 2S, 3E)-2-(3,4-dichlorobenzyl)-1-methyl-4-(2-naphthyl)-3-butenylamine obtained in Example 124, 591 mg of di-tert-butyl (2S)-carboxymethylsuccinate obtained in Example 116 and 250 mg of 4-dimethylaminopyridine were dissolved in 10 ml of methylene chloride, and 393 mg of 1-ethyl-3-(3-dimethylaminopropyl)carbodiimide hydrochloride was added thereto. The mixture was stirred at room temperature for 2 hours. The reaction solution was diluted with ethyl acetate, then sequentially washed with 1N hydrochloric acid, a saturated sodium hydrogencarbonate aqueous solution and a saturated sodium chloride aqueous solution and dried over anhydrous magnesium sulfate. The drying agent was separated by filtration, and then the solvent was distilled off under reduced pressure. The residue was subjected to silica gel column chromatography (Wakogel™ C-200, 25 g; hexane/ethyl acetate=5/1+3/1) to obtain 920 mg (yield: 84%) of a di-tert-butyl ester of the above-identified compound.

920 mg of the ester compound thus-obtained was added to 8 ml of formic acid, and the mixture was stirred at room temperature for 4 hours. Then, formic acid was distilled off under reduced pressure. The residue was treated with a liquid mixture of ethyl ether and hexane. Then, the precipitate was collected by filtration and recrystallized from a liquid mixture of chloroform/methanol/hexane to obtain 400 mg (yield: 53%) of the above-identified compound as white crystalline powder having a melting point of from 161° to 163° C. and $[\alpha]_D^{20}$=+86.6° (c=1.0, methanol)

¹H-NMR(CDCl₃)δ: 1.19(3H, d, J=6.8 Hz), 2.45–2.75(6H, m), 2.92–2.99(1H, m), 3.16–3.40(1H, m), 3.99–4.04(1H, m), 6.16(1H, dd, J=8.5 Hz, 16.0 Hz), 6.31(1H, d, J=16.0 Hz), 7.11(1H, dd, J=2.0 Hz, 8.5 Hz), 7.33(1H, d, J=7.9 Hz), 7.37–7.44(3H, m), 7.56(1H, dd, J=1.5 Hz, 8.5 Hz), 7.63(1H, br.d), 7.73–7.78(3H, m).

Compounds of Examples 53 to 55 were prepared in the same manner as in Example 52 except that (1S, 2S, 3E)-2-(3,4-dichlorobenzyl)-1-methyl-4-(2-naphthyl)-3-butenylamine and/or di-tert-butyl (2S)-carboxymethylsuccinate used as the starting materials in the above reaction were changed to N-{(1S, 2S, 3E)-2-(3,4-dichlorobenzyl)-1-methyl-4-(2-naphtnyl)-3-butenyl}methylamine and/or 5-(tert-butoxycarbonyl)-4-pentenoic acid.

EXAMPLE 53

(2S)-2-[N-{(1S, 2S, 3E)-2-(3,4-Dichlorobenzyl)-1-methyl-4-(2-naphthyl)-3-butenyl}-N-methylcarbamoylmethyl]succinic acid ¹H-NMR(CDCl₃)δ: 1.15(3H, d, J=6.5 Hz), 2.45–2.96(7H, m), 2.86(3H, s), 3.36–3.45(1H, m), 4.74–4.79(1H, m), 5.99(1H, dd, J=9.4 Hz, 16.0 Hz), 6.32(1H, d, J=16.0 Hz), 6.89–6.94(1H, m), 7.19–7.20(1H, m), 7.24–7.28(1H, m), 7.40–7.51(3H, m), 7.59–7.61(1H, m), 7.74–7.78(3H, m).

EXAMPLE 54

(2E)-5-[N-{(1S, 2S, 3E)-2-(3,4-Dichlorobenzyl)-1-methyl4-(2-naphthyl)-3-butenyl}carbamoyl]-2-pentenoic acid ¹H-NMR(CDCl₃)δ: 1.18(3H, d, J=6.9 Hz), 2.30(2H, t, J=7.2 Hz), 2.54–2.71(4H, m), 2.78–2.89(1H, m), 4.10–4.23(1H, m), 5.45(1H, d, J=9.0 Hz), 5.85(1H, d, J=15.6

Hz), 6.08(1H, dd, J=9.0 Hz, 15.9 Hz), 6.39(1H, d, J=15.6 Hz), 6.99(1, dd, J=2.1 Hz, 8.1 Hz), 7.03(1H, dt, J=6.9 Hz, 15.6HZ), 7.26(1H, s), 7.28(1H, d, J=8.4 Hz), 7.40–7.47(2H, m), 7.51(1H, dd, J=1.8 Hz, 8.4 Hz), 7.62(1H, s), 7.75–7.79(3H, m).

EXAMPLE 55

(2E)-5-[N-{(1S, 2S, 3E)-2-(3,4-Dichlorobenzyl)-1-methyl-4-(2-naphthyl)-3-butenyl}-N-methyl-carbamoyl]-2-pentenoic acid $^1$H-NMR(CDCl$_3$)δ: 1.16, 1.26(total 3H, d, J=7.2 Hz), 2.40–2.80(7H, m), 2.85, 2.93(total 3H, s), 3.79–3.87, 4.78–4.89(total 1H, m), 5.90(1H, dt, J=1.5 Hz, 15.6 Hz), 5.97–6.07(1H, m), 6.31(1H, d, J=15.6 Hz), 6.89–6.95(1H, m), 7.13(1H, dt, J=6.9 Hz, 15.6 Hz), 7.19–7.21(1H, m), 7.24–7.29(1H, m), 7.39–7.51(3H, m), 7.59, 7.61(total 1H, s), 7.74–7.81(3H, m).

EXAMPLE 56

Preparation of 4-[N-{(1RS, 2RS)-2-(4-biphenylyl)-1-methyl-3-(2-naphthyl)propyl}-carbamoyl]-3-methylbutanoic acid 36 mg of (1RS, 2RS)-2-(4-biphenylyl)-1-methyl-3-(2-naphthyl)propylamine hydrochloride and 21 mg of 3-methylglutaric anhydride were dissolved in 3 ml of methylene chloride, and 100 μl of triethylamine was added thereto. The mixture was stirred at room temperature overnight. The reaction solution was poured into ice water and then acidified by an addition of 1N hydrochloric acid. Then, the organic layer was separated. The organic layer was dried over anhydrous sodium sulfate, and then the solvent was distilled off under reduced pressure. The residue was subjected to silica gel column chromatography (Wakogel™ C-100, 10 g, methylene chloride→methylene chloride/methanol=30/1) to obtain 42 mg (yield: 96%) of the above identified compound as white foamy solid.

$^1$H-NMR(CDCl$_3$)δ: 1.03–1.14(6H, m), 2.08–2.30(2H, m), 2.30–2.49(3H, m), 3.10–3.30(3H, m), 4.39–4.52(1H, m), 5.46–5.53(1H, m), 7.15–7.29(3H, m), 7.30–7.59(10H, m), 7.61–7.77(3H, m).

Compounds of Examples 57 to 65 were prepared in the same manner as in Example 56 except that (1RS, 2RS)-2-(4-biphenylyl)-1-methyl-3-(2-naphthyl)propylamine and/or 3-methylglutaric anhydride used as the starting materials in the above reaction were changed to the corresponding amine compounds and/or acid anhydrides.

EXAMPLE 57

4-[N-{(1RS, 2RS)-2-(4-Biphenylyl)-3-(3,4-dichlorophenyl)-1-methylpropyl}carbamoyl]-butanoic acid $^1$H-NMR(CDCl$_3$)δ: 1.04(3H, d, J=6.8 Hz), 2.01(2H, m), 2.28(2H, t, J=7.2 Hz), 2.47(2H, t, J=6.8 Hz), 2.96–3.09(3H, m), 4.39(1H, m), 5.32(1H, m), 6.82(1H, br.d, J=8.6 Hz), 7.12–7.22(4H, m), 7.30–7.60(7H, m).

EXAMPLE 58

4-[N-{(1RS, 2RS)-2-(4-Biphenylyl)-3-(3,4-dichlorophenyl)-1-methylpropyl}-carbamoyl]-3-methylbutanoic acid $^1$H-NMR(CDCl$_3$)δ: 1.06–1.09(6H, m), 2.15–2.35(2H, m), 2.35–2.52(3H, m), 2.86–3.10(3H, m), 4.39(1H, m), 5.51(1H, br.d, J=9.4 Hz), 6.80(1H, br.d, J=8.0 Hz), 7.10–7.22(4H, m), 7.30–7.60(7H, m).

EXAMPLE 59

4-[N-{(1RS, 2RS)-2-(4-Biphenylyl)-1-methyl-3-(1-naphthyl)propyl}carbamoyl]-3-methylbutanoic acid $^1$H-NMR(CDCl$_3$+CD$_3$OD)δ: 1.03–1.13(6H, m), 2.05–2.23(2H, m), 2.24–2.48(3H, m), 3.11–3.21(1H, m), 3.68(1H, br.d, J=14.1 Hz), 4.49–4.58(1H, m), 7.00–7.07(1H, m), 7.12–7.25(2H, m), 7.32–7.37(1H, m), 7.39–7.60(8H, m), 7.60–7.77(1H, m), 7.80–7.86(1H, m), 8.02(1H, br.d, J=8.1 Hz).

EXAMPLE 60

4-[N-{(1RS, 2RS)-2-(4-Biphenylyl)-3-(3,4-dichlorophenyl)-1-methylpropyl}carbamoyl]-3,3-dimethylbutanoic acid $^1$H-NMR(CDCl$_3$)δ: 1.09(3H, s), 1.09(3H, d, J=6.9 Hz), 1.16(3H, s), 2.25(1H, d, J=13.8 Hz), 2.44(1H, d, J=12.3 Hz), 2.50(1H, d, J=12.3 Hz), 2.89–3.10(3H, m), 4.41(1H, m), 5.98(1H, m), 6.79(1H, dd, J=1.8 Hz, 8.4 Hz), 7.11(1H, d, J=1.8 Hz), 7.14(2H, d, J=8.2 Hz), 7.20(1H, d, J=8.4 Hz), 7.36(1H, br.d, J=7.2 Hz), 7.44(2H, m), 7.52(2H, d, J=8.2 Hz), 7.57(1H, br.d, J=7.2 Hz).

EXAMPLE 61

4-[N-{(1RS, 2RS)-2-(4-Biphenylyl)-3-(3,4-dichlorophenyl)-1-methylpropyl}-N-methylcarbamoyl]-3-methylbutanoic acid $^1$H-NMR(CDCl$_3$)δ: 0.90–1.07 (3H, m), 1.14(3H, d, J=6.3 Hz), 2.30–2.60(6H, m), 2.60–2.96(5H, m), 4.10–4.30 and 5.08–5.28 (total 1 H, m), 6.60–6.70(1H, m), 6.90–7.00(1H, m), 7.07–7.20(3H, m), 7.30–7.63(7H, m).

EXAMPLE 62

3-[N-{(1RS, 2RS)-2-(4-Biphenylyl)-3-(3,4-dichlorophenyl)-1-methylpropyl}carbamoyl methyl]pentanoic acid $^1$H-NMR(CDCl$_3$)δ: 0.96(3H, t, J=7.2 Hz), 1.03(3H, d, J=6.8 Hz), 1.42–1.48(2H, m), 2.21–2.39(3H, m), 2.41–2.51(2H, m), 2.87–2.97(2H, m), 3.06–3.09(1H, m), 4.36–4.41(1H, m), 5.69–5.72(1H, m), 6.76–6.81(1H, m), 7.10(1H, t, J=2.4 Hz), 7.13(2H, d, J=8.0 Hz), 7.18(1H, dd, J=2.0 Hz, 8.4 Hz), 7.33(1H, t, J=7.2 Hz), 7.43(2H, t, J=7.6 Hz), 7.50(2H, d, J=8.0 Hz), 7.57(2H, d, J=7.2 Hz).

EXAMPLE 63

3-[N-{(1RS, 2RS)-2-(4-Biphenylyl)-3-(3,4-dichlorophenyl)-1-methylpropyl}-carbamoylmethyl]-4-methylpentanoic acid $^1$H-NMR(CDCl$_3$)δ: 0.93(6H, d, J=6.8 Hz), 1.03(3H, d, J=6.6 Hz), 1.70–1.88(1H, m), 2.12–2.53(5H, m), 2.82–3.11(3H, m), 4.28–4.48(1H, m), 5.67(1H, br.d, J=9.0 Hz), 6.79(1H, dt, J=2.2 Hz, 8.4 Hz), 7.09–7.25(4H, m), 7.30–7.60(7H, m).

EXAMPLE 64

4-[N-{(1RS, 2RS)-2-(4-Biphenylyl)-3-(3,4-dichlorophenyl)-1-methylpropyl}carbamoyl]-3-benzylbutanoic acid $^1$H-NMR(CDCl$_3$)δ: 1.01(3/2H, d, J=6.8 Hz), 1.04(3/2H, d, J=6.8 Hz), 2.17–2.35(2H, m), 2.53–2.80(3H, m), 2.87–3.09(3H, m), 4.31–4.42(1H, m), 5.40–5.49(1H, m), 6.77(1H, dd, J=2.3 Hz, 8.3 Hz), 7.08–7.14(3H, m), 7.15–7.24(4H, m), 7.26–7.37(3H, m), 7.39–7.46(2H, m), 7.49(2H, d, J=8.1 Hz), 7.54–7.59(2H, m).

EXAMPLE 65

4-[N-{(1RS, 2RS)-2-(4-Biphenylyl)-3-(3,4-dichlorophenyl)-1-methylpropyl}carbamoyl]-3-hydroxy-3-methylbutanoic acid $^1$H-NMR(CDCl$_3$)δ: 1.05(3H, d, J=6.6 Hz), 1.38(3/2H, s), 1.40(3/2H, s), 2.40(1H, br.d, J=15.0 Hz), 2.50–2.64(3H, m), 2.84–2.99(2H, m), 3.00–3.12(1H, m), 4.32–4.45(1H, m), 5.95–6.12(1H, m), 6.77(1H, br.d, J=8.0 Hz), 7.08–7.14(3H, m), 7.18(1H, d, J=8.0 Hz), 7.33(1H, m), 7.42(2H, br.t, J=7.5 Hz), 7.50(2H, br.d, J=7.8 Hz), 7.56(2H, br.d, J=7.5 Hz).

EXAMPLE 66

Preparation of 5-[N-{(1S, 2S)-2-(4-biphenylyl)-3-(3,4-dichlorophenyl)-1-methoxypropyl}carbamoyl]pentanoic acid 24 mg of (1S, 2S)-2-(4-biphenylyl)-3-(3,4-dichlorophenyl)-1-methylpropylamine obtained in Example 115, 14 mg of monoethyl adipate and 10 mg of 4-dimethylaminopyridine were dissolved in 2 ml of methylene chloride, and 15 mg of 1-ethyl-3-(3-dimethyaminopropyl)carbodiimide hydrochloride was added thereto with stirring under cooling with ice. The mixture was stirred at room temperature for 3 hours. The reaction solution was diluted with ethyl ether, then sequentially washed with a 10% citric acid aqueous solution, a saturated sodium hydrogencarbonate aqueous solution and a saturated sodium chloride aqueous solution, and dried over anhydrous magnesium sulfate. Then, the solvent was distilled off under reduced pressure. The residue was purified by silica gel column chromatography (Wakogel™ C-200, 1 g, hexane/ethyl acetate=2/1), and 28 mg of the obtained amide compound was dissolved in 1 ml of methanol. Then, 0.5 ml of a 2N sodium hydroxide aqueous solution was added thereto, and the mixture was stirred at room temperature overnight. The reaction solution was acidified with 1N hydrochloric acid and then subjected to liquid separation by an addition of ethyl ether and water. The organic layer was collected by separation, then washed with a saturated sodium chloride aqueous solution and dried over anhydrous magnesium sulfate. The drying agent was separated by filtration, and then the solvent was distilled off. The residue was treated with a liquid mixture of isopropyl ether and ethyl ether to obtain 16 mg (yield: 49%) of the above-identified compound as white crystalline powder having a melting point of from 123° to 124° C. and [α]$_D^{20}$=+139° (c=1.0, methanol).

$^1$H-NMR(CDCl$_3$)δ: 1.03(3H, d, J=6.9 Hz), 1.70(4H, m), 2.21(2H, m), 2.41(2H, m), 2.88–2.98(3H, m), 4.36(1H, m), 5.33(1H, d, J=9.0 Hz), 6.82(1H, d, J=1.8 Hz, 8.3 Hz), 7.34(1H, m), 7.43(2H, m), 7.51(2H, d, J=8.3 Hz), 7.57(2H, m).

Compounds of Examples 67 to 71 were prepared in the same manner as in Example 66 except that (1S, 2S)-2-(4-biphenylyl)-3-(3,4-dichlorophenyl)-1-methylpropylamine and monoethyl adipate used as the starting materials in the above reaction were changed to the respective corresponding amine compounds and/or monoester derivatives.

EXAMPLE 67

8-[N-{(1RS, 2RS)-2-(4-Biphenylyl)-3-(3,4-dichlorophenyl)-1-methylpropyl}-carbamoyl]octanoic acid $^1$H-NMR(CDCl$_3$)δ: 1.03(3H, d, J=6.8 Hz), 1.34(6H, m), 1.63(4H, m), 2.17(2H, t, J=7.3 Hz), 2.34(2H, t, J=7.3 Hz), 2.91–3.09(3H, m), 4.38(1H, m), 5.23(1H, d, J=8.7 Hz), 6.82(1H, d, J=2.0 Hz, 8.3 Hz), 7.12–7.16(3H, m), 7.19(1H, d, J=8.3 Hz), 7.34(1H, m), 7.43(2H, m), 7.51(2H, d, J=8.4 Hz), 7.58(2H, m).

EXAMPLE 68

5-[N-{(1S, 2S)-3-(3,4-Dichlorophenyl)-2-(2-fluoro-4-biphenylyl)-1-methylpropyl}-carbamoyl]pentanoic acid biphenylyl $^1$H-NMR (CDCl$_3$)δ: 1.04(3H, d, J=6.9 Hz), 1.69–1.71(4H, m), 2.22(2H, t, J=6.8 Hz), 2.41(2H, t, J=6.3 Hz), 2.85–3.10(3H, m), 4.30–4.42(1H, m), 5.47(1H, d, J=8.8 Hz), 6.83(1H, dd, J=2.3 Hz, 8.4 Hz), 6.87–6.94(2H, m), 7.13(1H, d, J=2.3 Hz), 7.22(1H, d, J=8.4 Hz), 7.32–7.39(2H, m), 7.41–7.46(2H, m), 7.51–7.54(2H, m).

EXAMPLE 69

(E)-5-[N-{(1RS, 2RS)-2-(4-Biphenylyl)-3-(3,4-dichlorophenyl)-1-methylpropyl}-carbamoyl]-4-pentenoic acid $^1$H-NMR(CDCl$_3$)δ: 1.04(3H, d, J=6.8 Hz), 2.45–2.60(4H, br.), 2.90–3.15(3H, m), 4.35–4.55(1H, m), 5.40–5.50(1H, m), 5.78(1H, d, J=15.2 Hz), 6.80–6.95(2H, m), 7.10–7.65(11H, m).

EXAMPLE 70

(E)-5-[N-{(1S, 2S)-3-(3,4-Dichlorophenyl)-2-(2-fluoro-4-biphenylyl)-1-methylpropyl}-carbamoyl]-2-pentenoic acid $^1$H-NMR(CDCl$_3$)δ: 1.05(3H, d, J=6.7 Hz), 2.34(2H, t, J=7.0 Hz), 2.54–2.70(2H, m), 2.84–3.10(3H, m), 4.30–4.45(1H, m), 5.20–5.33(1H, m), 5.87(1H, d, J=15.7 Hz), 6.58–7.60(12H, m).

EXAMPLE 71

5-[N-{(1RS, 2RS)-2-(4-Biphenylyl)-1-methyl-3-(2-naphthyl)propyl}carbamoyl]pentanoic acid $^1$H-NMR(CDCl$_3$)δ: 1.06(3H, d, J=6.9 Hz), 1.64–1.66(4H, m), 2.13(2H, t, J=6.7 Hz), 3.10–3.28(3H, m), 4.37–4.49(1H, m), 5.29(1H, d, J=9.3 Hz), 7.18–7.22(3H, m), 7.28–7.43(5H, m), 7.48–7.57(5H, m), 7.64–7.74(3H, m).

EXAMPLE 72

Preparation of (2E)-5-[N-{(1S, 2S, 3E)-2-(3,4-dichlorobenzyl)-1-methyl-4-(2-naphthyl)-3-butenyl}carbamoyl]-3-methyl-2-pentenoic acid 2.06 g of (1S, 2S, 3E)-2-(3,4-dichlorobenzyl)-1-methyl-4-(2-naphthyl)-3-butenylamine hydrochloride obtained in Example 124, 1.20 g of (E)-5-(allyloxycarbonyl)-4-methyl-4-pentenoic acid obtained in Reference Example 6 and 1.12 g of 4-dimethylaminopyridine were dissolved in 100 ml of methylene-chloride, and 1.20 g of 1-ethyl-3-(3-dimethylaminopropyl)carbodiimide hydrochloride was added thereto with stirring under cooling with ice. The mixture was stirred at room temperature for 12 hours. The reaction solution was concentrated under reduced pressure. Then, ethyl acetate and 1N hydrochloric acid were added to the residue for liquid separation. The organic layer was collected by separation and then washed with a saturated sodium hydrogencarbonate aqueous solution and a saturated sodium chloride aqueous solution. The extract solution was dried over anhydrous magnesium sulfate, and then the solvent was distilled off under reduced pressure. The residue was treated with a liquid mixture of methylene chloride-hexane to obtain 2.28 g (yield: 82%) of an allyl ester of the above-identified compound as white crystalline powder.

2.28 g of the ester compound thus obtained was dissolved in 50 ml of tetrahydrofuran, and 0.91 g of dimedone and 0.49 g of tetrakis(triphenylphosphine)palladium were added thereto. The mixture was stirred at room temperature for 3 hours. The reaction solution was concentrated under reduced pressure. Then, the residue was subjected to liquid separation by an addition of methylene chloride and water. The organic layer was collected by separation and then dried over anhydrous magnesium sulfate. The drying agent was separated by filtration, and then the solvent was distilled off under reduced pressure. The residue was purified by silica gel column chromatography (Wakogel™ C-200, methylene chloride/methanol=100/1→50/1) and then recrystallized from a liquid mixture of methylene chloride-hexane to obtain 1.26 g (yield: 59%) of the above-identified compound as white crystalline powder having a melting point of from 146° to 148° C. and [α]$_D^{20}$=+63.8° (c=1.0, chloroform).

$^1$H-NMR(CDCl$_3$)δ: 1.20(3H, d, J=6.9 Hz), 2.18(3H, s), 2.33(2H, t, J=7.5 Hz), 2.53(2H, m), 2.57–2.74(2H, m), 2.83(1H, m), 4.18(1H, m), 5.39(1H, d, J=9.0 Hz), 5.70(1H, br.), 6.09(1H, dd, J=9.0 Hz, 15.3 Hz), 6.39(1H, d, J=15.3 Hz), 7.00(1H, dd, J=2.4 Hz, 8.4 Hz), 7.25–7.30(2H, m), 7.40–7.49(2H, m), 7.51(1H, dd, J=1.5 Hz, 8.4 Hz), 7.63(1H, br.), 7.75–7.81(3H, m).

EXAMPLE 73

Preparation of (3R)-4-[N-{(1S, 2S)-2-(4-biphenylyl)-3-(3,4-dichlorophenyl)-1-methylpropyl}carbamoyl]-3-methylbutanoic acid 1.40 g of (1S, 2S)-2-(4-biphenylyl)-3-(3,4-dichlorophenyl)-1-methylpropylamine obtained in Example 115, 0.61 g of methyl (R)-(+)-3-methylglutarate and 0.47 g of 4-dimethylaminopyridine were dissolved in 10 ml of methylene chloride, and 0.73 g of 1-ethyl-3-(3-dimethylaminopropyl)carbodiimide hydrochloride was added thereto with stirring under cooling with ice. The mixture was stirred at room temperature for 4 hours. The reaction solution was sequentially washed with 1N hydrochloric acid, a saturated sodium hydrogencarbonate aqueous solution and a saturated sodium chloride aqueous solution, and dried over anhydrous magnesium sulfate. The drying agent was separated by filtration, and then the solvent was distilled off under reduced pressure. The residue was subjected to silica gel column chromatography (Wakogel™ C-100, 200 g; hexane/ethyl acetate =2/1) to obtain 1.81 g (yield: 93%) of a methyl ester of the above-identified compound.

1.81 g of the ester compound thus obtained was dissolved in 50 ml of acetic acid, and 35 ml of concentrated hydrochloric acid was added thereto. The mixture was stirred at room temperature for 15 hours. The reaction solution was concentrated under reduced pressure. Then, ethyl acetate and water were added to the residue for extraction. The organic layer was collected by separation and dried over anhydrous magnesium sulfate. The drying agent was separated by filtration, and then the solvent was distilled off under reduced pressure. The residue was purified by silica gel column chromatography (Wakogel™ C-200, 200 g; methylene chloride/methanol=10/1) and the recrystallized from an aqueous methanol solution to obtain 1.18 g (yield: 67%) of the above-identified compound as colorless needles having a melting point of from 133° to 134.5° C. and [α]$_D^{20}$=+153° (c=1.0, methanol).

$^1$H-NMR(CDCl$_3$)δ: 1.04(3H, d, J=6.3 Hz), 1.09(3H, d, J=6.3 Hz), 2.17–2.35(2H, m), 2.35–2.54(3H, m), 2.88–3.09(3H, m), 4.30–4.39(1H, m), 5.50–5.60(1H, m), 6.79(1H, dd, J=2.1 Hz, 8.4 Hz), 7.11(1H, d, J=2.1 Hz), 7.13(2H, d, J=8.1 Hz), 7.19(1H, d, J=8.4 Hz), 7.33(1H, tt, J=1.5 Hz, 6.8 Hz), 7.43(2H, m), 7.51(2H, d, J=8.1 Hz), 7.57(2H, br.d, J=6.9 Hz).

Compounds of Examples 74 and 75 were prepared in the same manner as in Example 73 except that (1S, 2S)-2-(4-biphenylyl)-3-(3,4-dichlorophenyl)-1-methylpropylamine used as the starting material in the above reaction was changed to (1S, 2S)-2-(2-fluoro-4-biphenylyl)-3-(3,4-dichlorophenyl)-1-methylpropylamine or (1S, 2S, 3E)-2-(3,4-dichlorobenzyl)-1-methyl-4-(2-naphthyl)-3-butenylamine.

EXAMPLE 74

(3R)-4-[N-{(1S, 2S)-3-(3,4-Dichlorophenyl)-2-(2-fluoro-4-biphenylyl)-1-methylpropyl}-carbamoyl]-3-methylbutanoic acid $^1$H-NMR(CDCl$_3$)δ: 1.05(3H, d, J=6.5 Hz), 1.09(3H, d, J=6.3 Hz), 2.20(1H, dd, J=6.9 Hz, 13.2 Hz), 2.30(1H, dd, J=6.3 Hz, 14.1 Hz), 2.32–2.50(3H, m), 2.84–3.00(2H, m), 3.06(1H, dd, J=3.9 Hz, 12.6 Hz), 4.37(1H, q, J=6.5 Hz), 5.60(1H, d, J=6.8 Hz), 6.81(1H, dd, J=2.1 Hz, 8.1 Hz), 6.85–6.93(2H, m), 7.12(1H, d, J=2.0 Hz), 7.15–7.25(2H, m), 7.31–7.46(3H, m), 7.51–7.54(2H, m).

EXAMPLE 75

(3R)-4-[N-{(1S, 2S, 3E)-2-(3,4-Dichlorobenzyl)-1-methyl-4-(2-naphthyl)-3-butenyl}carbamoyl]-3-methylbutanoic acid mp 146°–147° C.

¹H-NMR(CDCl₃)δ: 1.04(3H, d, J=6.3 Hz), 1.19(3H, d, J=6.9 Hz), 2.11–2.30(3H, m), 2.35–2.47(2H, m), 2.57–2.68(2H, m), 2.94(1H, d, J=10.2 Hz), 4.03(1H, quint., J=6.6 Hz), 6.15(1H, dd, J=8.4 Hz, 15.3 Hz), 6.30(1H, d, J=15.3 Hz), 7.10(1H, d, J=8.1 Hz), 7.31–7.44(4H, m), 7.55(1H, d, J=8.7 Hz), 7.62(1H, s), 7.73–7.78(3H, m).

EXAMPLE 76

Preparation of (3R*)- and (3S*)-4-[N-{(1S, 2S)-2-(4-biphenylyl)-3-(3,4-dichlorophenyl)-1-methylpropyl}carbamoyl]-3-methoxybutanoic acid 324 mg of a 3-methoxyglutaric acid was dissolved in 3 ml of acetic anhydride, and the solution was heated at 90° C. for 2 hours and then evaporated to dryness under reduced pressure. The residue was dissolved in 10 ml of methylene chloride, and 214 mg of (1S, 2S)-2-(4-biphenylyl)-3-(3,4-dichlorophenyl)-1-methylpropylamine and 150 µl of triethylamine were added thereto. The mixture was stirred at room temperature for 5 hours. To the reaction solution, 5 ml of a 0.1N sodium hydroxide aqueous solution was added, and the mixture was stirred at room temperature for one hour and then acidified by an addition of 1N hydrochloric acid. The organic layer was collected by separation, washed with a saturated sodium chloride aqueous solution and then dried over anhydrous magnesium sulfate. The drying agent was separated by filtration, and the solvent was distilled off under reduced pressure. The residue was dissolved in 15 ml of acetone, and then 310 mg of diphenyldiazomethane was added thereto. The mixture was stirred at room temperature overnight. The solvent was distilled off under reduced pressure, and the residue was roughly purified by silica gel column chromatography (Wakogel™ C-100, 50 g; hexane/ethyl acetate=2/1) and then subjected to medium pressure liquid chromatography (Lobar column™, size B, Lichroprep™ Si60F, manufactured by Merck Co.; hexane/ethyl acetate=5/2) to obtain the above identified two compounds in the form of the respective benzhydryl esters in an amount of 49 mg as the first eluate component and 121 mg as the later eluate component.

The benzhydryl ester of the first eluate component thus obtained was subjected to removal of the protecting group with trifluoroacetic acid in the same manner as in Example 46 to obtain 27 mg (yield: 9.1%) of the above-identified compound with the unidentified absolute configuration at the 3-position of butanoic acid being termed R* as a matter of convenience. Likewise, the later eluate component was subjected to removal of the protecting group in the same manner to obtain 72 mg (yield: 24%) of the above-identified compound with the unidentified absolute configuration at the 3-position of butanoic acid being termed S* as a matter of convenience. Both compounds were white crystalline powders.

(3R*)-isomer
¹H-NMR(CDCl₃)δ: 1.03(3H, d, J=6.9 Hz), 2.52(1H, d, J=14.7 Hz), 2.54(1H, d, J=14.7 Hz), 2.64(1H, dd, J=4.0 Hz, 14.7 Hz), 2.72(1H, dd, J=4.6 Hz, 14.7 Hz), 2.86–2.97(2H, m), 3.09(1H, m), 3.36(3H, s), 4.05(1H, m), 4.39(1H, m), 6.12(1H, br.d, J=9.3 Hz), 6.78(1H, dd, J=2.1 Hz, 8.4 Hz), 7.10(1H, d, J=2.1 Hz), 7.13(2H, d, J=8.4 Hz), 7.18(1H, d, J=8.4 Hz), 7.33(1H, br.t, J=8.4 Hz), 7.43(2H, m), 7.50(2H, d, J=8.4 Hz), 7.56(2H, m).

(3S*)-isomer
¹H-NMR(CDCl₃)δ: 1.04(3H, d, J=6.9 Hz), 2.54(1H, dd, J=8.1 Hz, 14.7 Hz), 2.55–2.65(2H, m), 2.77(1H, dd, J=4.8 Hz, 14.7 Hz), 2.85–2.94(2H, m), 3.10(1H, m), 3.38(3H, s), 4.01(1H, m), 4.39(1H, m), 6.08(1H, m), 6.76(1H, dd, J=2.1 Hz, 8.0 Hz), 7.10(1H, d, J=2.1 Hz), 7.13(2H, d, J=8.1 Hz), 7.18(1H, d, J=8.0 Hz), 7.34(1H, br.t, J=7.2 Hz), 7.43(2H, m), 7.51(2H, d, J=8.1 Hz), 7.57(2H, br.d, J=7.2 Hz).

Compounds of Examples 77 and 78 were prepared in the same manner as in Example 76 except that 3-methoxyglutaric acid and/or (1S, 2S)-2-(4-biphenylyl)-3-(3,4-dichlorophenyl)-1-methylpropylamine used as the starting materials in the above reaction were changed to 3-phenylglutaric acid and (1RS, 2RS)-2-(4-biphenylyl)-3-(3,4-dichlorophenyl)-1-methylpropylamine or (1S, 2S, 3E)-2-(3,4-dichlorobenzyl)-1-methyl-4-(2-naphthyl)-3-butenylamine.

EXAMPLE 77

(3R*)- and (3S*)-4-[N-{(1S, 2S, 3E)-2-(3,4-Dichlorobenzyl)-1-methyl-4-(2-naphthyl)-3-butenyl}carbamoyl]-3-methoxybutanoic acid (3R*)-isomer
¹H-NMR(CDCl₃)δ: 1.20(3H, d, J=6.9 Hz), 2.45–2.75(6H, m), 2.78–2.90(1H, m), 3.28(3H, s), 3.95(1H, m), 4.18(1H, m), 6.08(1H, dd, J=9.0 Hz, 15.6 Hz), 6.38(1H, d, J=15.6 Hz), 6.99(1H, dd, J=2.1 Hz, 8.4 Hz), 7.25–7.30(2H, m), 7.40–7.53(3H, m), 7.62(1H, br), 7.73–7.81(3H, m).

(3S*)-isomer
¹H-NMR(CDCl₃)δ: 1.21(3H, d, J=6.9 Hz), 2.45–2.75(6H, m), 2.83(1H, m), 3.29(3H, s), 3.96(1H, m), 4.18(1H, m), 6.09 (1H, dd, J=9.0 Hz, 15.6 Hz), 6.31(1H, br.d, J=8.4 Hz), 6.40(1H, d, J=15.6 Hz), 7.00(1H, dd, J-2.1 Hz, 8.4 Hz), 7.27–7.31(2H, m), 7.40–7.54(3H, m), 7.63(1H, br), 7.74–7.82(3H, m).

EXAMPLE 78

(3R*)- and (3S*)-4-[N-{(1RS, 2RS)-2-(4-Biphenylyl)-3-(3,4-dichlorophenyl)-1-methylpropyl}carbamoyl]-3-phenylbutanoic acid (3R*)-isomer
¹H-NMR (CDCl₃)δ: 0.73(3H, d, J=6.8 Hz), 2.50(1H, br.dd, J=11.2 Hz, 14.0 Hz), 2.65–2.95(6H, m), 3.65(1H, m), 4.20(1H, m), 5.13(1H, br.d, J=9.0 Hz), 6.70(1H, dd, J=2.0 Hz, 8.2 Hz), 6.97–7.04(3H, m), 7.14–7.50(10H, m), 7.51–7.60(3H, m).

(3S*)-isomer
¹H-NMR(CDCl₃)δ: 0.88(3H, d, J=6.8 Hz), 2.49 (1H, dd, J=9.0 Hz, 13.8 Hz), 2.40–2.80(6H, m), 3.70(1H, m), 4.25(1H, m), 5.18(1H, br.d, J=8.8 Hz), 6.63(1H, dd, J=2.0 Hz, 8.2 Hz), 6.86–6.95(3H, m), 7.14(1H, d, J=8.2 Hz), 7.14–7.48(10H, m), 7.52–7.59(3H, m).

EXAMPLE 79

Preparation of sodium (4S)-4-[N-{(1RS, 2RS)-2-(4-biphenylyl)-3-(3,4-dichlorophenyl)-1-methylpropyl}carbamoyl]-4-hydroxybutanoate 18.5 mg of (1RS, 2RS)-2-(4-biphenylyl)-3-(3,4-dichlorophenyl)-1-methylpropylamine, 9,8 mg of (S)-(+)-5-oxo-2-tetrahydrofurancarboxylic acid and 10.1 mg of 1-hydroxybenzotriazole were dissolved in 1 ml of methylene chloride, and 14.4 mg of 1-ethyl-3-(3-dimethylaminopropyl)carbodiimide hydrochloride was added thereto. The mixture was stirred at room temperature for 2 hours. The reaction solution was diluted with ethyl acetate and then sequentially washed with 1N hydrochloric acid and a saturated sodium chloride aqueous solution and dried over anhydrous magnesium sulfate. The drying agent was separated by filtration, and the solvent was distilled off under reduced pressure. The residue was purified by medium pressure liquid chromatography (Lobar column™, size A, Lichroprep™ Si60F, manufactured by Merck Co.; hexane/ethyl acetate=1/1) to obtain 19 mg (yield: 79%) of a lactone of the above identified compound i.e. (2S)-N-{(1RS, 2RS)-2-(4-biphenylyl)-3-(3,4-dichlorophenyl)-1-methylpropyl}-5-oxotetrahydrofuran-2-carboxamide.

15 mg of the lactone compound thus obtained was dissolved in a liquid mixture of 0.5 ml of tetrahydrofuran and 0.5 ml of methanol, and 34 µl of a 1N sodium hydroxide aqueous solution was added thereto. The mixture was stirred at room temperature overnight. The reaction solution was evaporated to dryness under reduced pressure to obtain 16 mg of the above identified compound as white glassy solid.

$^1$H-NMR(CDCl$_3$)δ: 0.99(3/2H, d, J=6.6 Hz), 1.00(3/2H, d, J=6.6 Hz), 1.88–2.05(1H, m), 2.05–2.20(1H, m), 2.36–2.47(2H, m), 2.75–2.88(1H, m), 2.92–3.03(1H, m), 3.12–3.21(1H, m), 4.07–4.17(1H, m), 4.23–4.36(1H, m), 6.84–6.92(1H, m), 7.10–7.60(11H, m).

EXAMPLE 80

Preparation of sodium (3R, 5S)-5-[N-{(1S, 2S, 3E)-2-(3,4-dichlorobenzyl)-1-methyl-4-(2-naphthyl)-3-butenyl}carbamoyl]-3,5-dihydroxypentanoate 1.0 g of tert-butyl (3R, 5S)-5-methoxycarbonyl-3,5-O-isopropylidene-3,5-dihydroxypentanoate was dissolved in 10 ml of tetrahydrofuran, and 3.5 ml of a 1N sodium hydroxide aqueous solution was added thereto. The mixture was stirred at room temperature for one hour. The solvent was distilled off under reduced pressure. Then, the residue was dissolved in methylene chloride, and 1N hydrochloric acid was added to adjust pH to 3.5. Then, the organic layer was collected by separation. The extract solution was dried over anhydrous magnesium sulfate, and then the solvent was distilled off under reduced pressure. The residue was dissolved in 20 ml of methylene chloride, and 1.41 g of (1S, 2S, 3E)-2-(3,4-dichlorobenzyl)-1-methyl-4-(2-naphthyl)-3-butenylamine hydrochloride, 0.89 g of 4-dimethylaminopyridine and 0.73 g of 1-ethyl-3-(3-dimethylaminopropyl)carbodiimide hydrochloride were added with stirring under cooling with ice. The mixture was stirred at room temperature for 15 hours. Water and methylene chloride were added to the reaction solution for liquid separation. The organic layer was collected by separation and dried over anhydrous sodium sulfate. The drying agent was separated by filtration, and the solvent was distilled off under reduced pressure. The residue was purified by silica gel column chromatography (Wakogel™ C-200, 100 g; hexane/ethyl acetate=3/1→2/1) to obtain 1.66 g (yield: 76%) of tert-butyl (3R, 5S)-5-[N-{(1S, 2S, 3E)-2-(3,4-dichlorobenzyl)-1-methyl-4-(2-naphthyl)-3-butenyl}carbamoyl]-3,5-O-isopropylidene-3,5-dihydroxypentanoate.

1.65 g of the isopropylidene compound thus obtained was dissolved in a liquid mixture of 4 ml of 1N hydrochloric acid and 18 ml of tetrahydrofuran, and the solution was stirred at room temperature for 18 hours. Then, tetrahydrofuran was distilled off under reduced pressure. Ethyl acetate was added to the residual solution for liquid separation. The organic layer was collected by separation, and dried over anhydrous magnesium sulfate. The drying agent was separated by filtration, and the solvent was distilled off under reduced pressure. The residue was dissolved in a liquid mixture of 4 ml of a 1N sodium hydroxide aqueous solution and 20 ml of methanol, and the solution was stirred at room temperature for one hour. Methanol was distilled off under reduced pressure from the reaction solution. The residual solution was acidified by an addition of 5 ml of 1N hydrochloric acid and extracted by an addition of ethyl acetate. The extract solution was washed with a saturated sodium chloride aqueous solution, and then dried over anhydrous magnesium sulfate. The drying agent was separated by filtration, and then the solvent was distilled off under reduced pressure to obtain 1.36 g (yield: 97%) of a free acid of the above-identified compound.

1.32 g of the carboxylic acid compound thus obtained was dissolved in 15 ml of methylene chloride, and 0.37 g of 4-dimethylaminopyridine and 0.57 g of 1-ethyl-3-(3-dimethylaminopropyl)carbodiimide hydrochloride were added thereto. The mixture was stirred at room temperature for 4 hours. 30 ml of 1N hydrochloric acid and 30 ml of methylene chloride were added to the reaction solution for liquid separation. The organic layer was collected by separation and dried over anhydrous magnesium sulfate. The drying agent was separated by filtration, and then the solvent was distilled off under reduced pressure. The residue was purified by silica gel column chromatography (Wakogel™ C-200, 100 g; ethyl acetate/hexane=3/1→ethyl acetate) and then recrystallized from a liquid mixture of chloroform-hexane to obtain 0.83 g (yield: 65%) of (4R, 6S)-6-[N-{(1S, 2S, 3E)-2-(3,4-dichlorobenzyl)-1-methyl-4-(2-naphthyl)-3-butenyl}carbamoyl]-4-hydroxy-3,4,5,6-tetrahydro-2H-pyran-2-one as white crystalline powder having a melting point of from 192° to 193° C.

100 mg of the lactone compound thus obtained was dissolved in a liquid mixture of 2 ml of a 1N sodium hydroxide aqueous solution and 4 ml of methanol, and the solution was stirred at room temperature for one hour. Then, 1 ml of water was added to the reaction solution, and the formed precipitate was collected by filtration. The crystals were washed with ethyl ether and hexane and dried to obtain 41 mg (yield: 43%) of the above-identified compound as white crystalline powder having a melting point of from 210° to 212° C. and $[α]_D^{20}$=+91.1° (c=1.06, methanol).

$^1$H-NMR(CD$_3$OD)δ: 1 21(3H, d, J=6 6 Hz), 1 74–1 84(1H, m), 1.93–2.01(1H, m), 2.30(1H, dd, J=8.1 Hz, 15.3 Hz), 2.42(1H, dd, J=4.8 Hz, 15.3 Hz), 2.57–2.71(2H, m), 2.96(1H, q, J=9.3 Hz), 4.04(1H, quint., J=6.6 Hz), 4.14–4.21(1H, m), 4.23(1H, dd, J=3.9 Hz, 9.0 Hz), 6.15(1H, dd, J=8.7 Hz, 15.9 Hz), 6.34(1H, d, J=15.9 Hz), 7.11(1H, dd, J=1.8 Hz, 8.1 Hz), 7.33(1H, d, J=8.1 Hz), 7.35–7.44(3H, m), 7.56(1H, dd, J=1.5 Hz, 8.7 Hz), 7.63(1H, s), 7.72–7.78(3H, m).

A compound of Example 81 was prepared in the same manner as in Example 80 except that (1S, 2S, 3E)-2-(3,4-dichlorobenzyl)-1-methyl-4-(2-naphthyl)-3-butenylamine used as the starting material in the above reaction was changed to (1S, 2S)-3-(3,4-dichlorophenyl)-2-(2-fluoro-4-biphenylyl)-1-methylpropylamine.

EXAMPLE 81

Sodium (3R, 5S)-5-[N-{(1S, 2S)-3-(3,4-dichlorophenyl)-2-(2-fluoro-4-biphenylyl)-1-methylpropyl}carbamoyl]-3,5-dihydroxypentanoate $^1$H-NMR(CD$_3$OD)δ: 1.01(3H, d, J=6.9 Hz), 1.82(1H, ddd, J=7.6 Hz, 8.5 Hz, 14.3 Hz), 2.00(1H, ddd, J=3.9 Hz, 5.1 Hz, 14.3 Hz), 2.33(1H, dd, J=7.6 Hz, 15.0 Hz), 2.45(1H, dd, J=4.9 Hz, 15.0 Hz), 2.80(1H, dd, J=11.3 Hz, 13.3 Hz), 2.97–3.05(1H, m), 3.18(1H, dd, J=3.8 Hz, 13.3 Hz), 4.17–4.34(3H, m), 6.91(1H, dd, J=2.0 Hz, 8.4 Hz), 6.95–7.01(2H, m), 7.15(1H, d, J=2.0 Hz), 7.25(1H, d, J=8.4 Hz), 7.30–7.44(4H, m), 7.47–7.52(2H, m).

EXAMPLE 82

Preparation of sodium 5-[N-{(1R, 2R)-2-(4biphenylyl)-3-(3,4-dichlorophenyl)-1methylpropyl}carbamoyl]-2,3,4,5-tetrahydroxypentanoate and sodium 5-[N-{(1S, 2S)-2-(4-biphenylyl)-3-(3,4-dichlorophenyl)-1-methylpropyl}carbamoyl]-2,3,4,5-tetrahydroxypentanoate 34.6 mg of diethyl 2,3:4,5-di-O-isopropylidene-2,3,4,5-tetrahydroxyadipate was dissolved in a liquid mixture of 1 ml of ethanol and 0.2 ml of water, and 0.1 ml of a 1N sodium hydroxide aqueous solution was added thereto. The mixture was left to stand at room temperature overnight. The reaction solution was evaporated to dryness under reduced pressure. The residue was dissolved in 2 ml of dimethylformamide, and 37 mg of (1RS, 2RS)-2-(4-biphenylyl)-3-(3,4-dichlorophenyl)-1-methylpropylamine, 15 mg of 1-hydroxybenzotriazole and 21 mg of 1-ethyl-3-(3-dimethylaminopropyl)carbodiimide hydrochloride were added thereto. The mixture was stirred at room temperature for 2 hours. The reaction solution was diluted with ethyl acetate, then washed with water and dried over anhydrous magnesium sulfate. The drying agent was separated by filtration, and then the solvent was distilled off under reduced pressure. The residue was purified by medium pressure liquid chromatography (Lobar column™, size A, Lichroprep™ Si60F, manufactured by Merck Co.; hexane/ethyl acetate=5/1→2/1) to obtain 39 mg (yield: 58%) of ethyl (2R, 3S, 4S, 5R)-5-[N-{(1RS, 2RS)-2-(4-biphenylyl)-3-(3,4-dichlorophenyl)-1-methylpropyl}carbamoyl]-2,3:4,5-di-O-isopropylidene-2,3,4,5-tetrahydroxypentanoate.

39 mg of the di-O-isopropylidene compound thus obtained was dissolved in 2 ml of ethanol, and 70 μl of a 1N sodium hydroxide aqueous solution was added thereto. The mixture was left to stand at room temperature overnight. The reaction solution was evaporated to dryness under reduced pressure. A liquid mixture of 0.75 ml of acetic acid and 0.25 ml of water, was added to the residue, and the mixture was heated at 90° C. for 3 hours. The reaction solution was evaporated to dryness under reduced pressure. The residue was purified by silica gel column chromatography (Wakogel™ C-200, 5 g; ethyl acetate) to obtain 5 mg (yield: 16%) of 5-[2-[N-{(1R, 2R)-2-(4-biphenylyl)-3-(3,4-dichlorophenyl)-1-methylpropyl}carbamoyl]-1-hydroxyethyl]-3,4-dihydroxytetrahydrofuran-2-one and 4 mg (yield: 13%) of 5-[2-[N-{(1S, 2S)-2-(4-biphenylyl)-3-(3,4-dichlorophenyl)-1-methylpropyl}carbamoyl]-1-hydroxyethyl]-3,4-dihydroxytetrahydrofuran-2-one.

5 mg of the (1R, 2R)-isomer thus obtained was dissolved in 1 ml of methanol, and 11 μl of a 1N sodium hydroxide aqueous solution was added thereto. The mixture was stirred at room temperature for 30 minutes. The reaction solution was evaporated to dryness under reduced pressure to obtain the (1R, 2R)-isomer of the above-identified compound as white powder.

$^1$H-NMR(CD$_3$OD)δ: 1.02(3H, d, J=6.5 Hz), 2.85(1H, dd, J=11.1 Hz, 13.2 Hz), 2.95–3.05(1H, m), 3.21(1H, dd, J=3.6 Hz, 13.2 Hz), 3.97(1H, dd, J=1.2 Hz, 9.9 Hz), 4.01(1H, dd, J=0.9 Hz, 9.9 Hz), 4.21(1H, d, J=1.2 Hz), 4.26–4.38(1H, m), 4.46(1H, d, J=0.9 Hz), 6.88 (in, dd, J=1.8 Hz, 8.4 Hz), 7.13–7.25(4H, m), 7.26–7.33(1H, m), 7.36–7.44(2H, m), 7.50–7.60(4H, m).

Using the (1S, 2S)-isomer of the lactone as the starting material, the reaction was conducted in the same manner as above to obtain the (1S, 2S)-isomer of the above-identified compound.

$^1$H-NMR(CD$_3$OD)δ: 0.99(3H, d, J=7.0 Hz), 2.71–2.94(2H, m), 3.33–3.40(1H, m), 3.98(1H, dd, J=1.2 Hz, 9.9 Hz), 4.03(1H, dd, J=1.2 Hz, 9.9 Hz), 4.22(1H, d, J=1.2 Hz), 4.30–4.42(1H, m), 4.45(1H, d, J=1.2 Hz), 6.83(1H, dd, J=1.8 Hz, 8.1 Hz), 7.10–7.23(4H, m), 7.26–7.33(1H, m), 7.36–7.44(2H, m), 7.49–7.61(4H, m).

EXAMPLE 83

Preparation of N-{(1RS, 2RS)-3-(4-biphenylyl)-2-(4-chlorophenyl)-1-methylpropyl}-N-(2-naphthylmethyl)carbamoylmethylsuccinic acid 46.5 mg of N-{(1RS, 2RS)-3-(4-biphenylyl)-2-(4-chlorophenyl)-1-methylpropyl}-2-naphthylmethylamine and 35 μl of N-ethyldiisopropylamine were dissolved in 1 ml of methylene chloride, and 31 mg of chloroformylmethylsuccinic anhydride was added thereto with stirring under cooling with ice. The mixture was stirred at room temperature for 30 minutes. The reaction solution was evaporated to dryness under reduced pressure. Then, the residue was dissolved in a liquid mixture of 1 ml of tetrahydrofuran and 0.5 ml of water, and 42 mg of lithium hydroxide (monohydrate) was added thereto. The mixture was stirred at room temperature for 15 minutes. The reaction solution was acidified by an addition of 1N hydrochloric acid and extracted by an addition of ethyl ether and a saturated sodium chloride aqueous solution. The organic layer was collected by separation and dried over anhydrous sodium sulfate. The drying agent was separated by filtration, and then the solvent was distilled off under reduced pressure. The residue was subjected to silica gel thin layer chromatography (Kieselgel™ 60F$_{254}$, Art 5744, manufactured by Merck Co.; methylene chloride/methanol=8/1) to obtain 40.1 mg (yield: 67%) of the above-identified compound as white powder.

$^1$H-NMR(CDCl$_3$+CD$_3$OD)δ: 0.83–0.95(3H, m), 2.45–3.40(8H, m), 4.25–4.93(3H, m), 6.85–7.85(20H, m).

Compounds of Examples 84 to 90 were prepared in the same manner as in Example 83 except that N-{(1RS, 2RS)-3-(4-biphenylyl)-2-(4-chlorophenyl)-1-methylpropyl}-2-naphthylmethylamine used as the starting material in the above reaction was changed to the corresponding naphthylmethylamine derivatives.

EXAMPLE 84

N-{(1RS, 2RS)-3-(3-Biphenylyl)-2-(4-chlorophenyl)-1-methylpropyl}-N-(2-naphthylmethyl)carbamoylmethylsuccinic acid $^1$H-NMR(CDCl$_3$+CD$_3$OD)δ: 0.83–1.00(3H, m), 2.25–3.50(8H, m), 4.25–5.00(3H, m), 6.30–7.90(20H, m).

EXAMPLE 85

N-{(1RS, 2RS)-3-(4'-Chloro-4-biphenylyl)-2-(4-chlorophenyl)-1-methylpropyl}-N-(2-naphthylmethyl)carbamoylmethylsuccinic acid $^1$H-NMR(CDCl$_3$+CD$_3$OD)δ: 0.85–1.00(3H, m), 2.45–3.50(8H, m), 4.25–4.95(3H, m), 6.35–7.90(19H, m).

EXAMPLE 86

N-{(1RS, 2RS)-2-(4-Chlorophenyl)-3-(2-fluoro-4-biphenylyl)-1-methylpropyl}-N-(2-naphthylmethyl)carbamoylmethylsuccinic acid $^1$H-NMR(CDCl$_3$+CD$_3$OD)δ: 0.85–1.00(3H, m), 2.45–3.40(8H, m), 4.25–4.85(3H, m), 6.05–7.90(19H, m).

EXAMPLE 87

N-{(1RS, 2RS)-2-(4-Chlorophenyl)-3-(6-fluoro-3-biphenylyl)-1-methylpropyl}-N-(2naphthylmethyl)carbamoylmethylsuccinic acid $^1$H-NMR(CDCl$_3$+CD$_3$OD)δ: 0.85–1.00(3H, m), 2.45–3.45(8H, m), 4.28–4.88(3H, m), 6.05–7.88(19H, m).

EXAMPLE 88

N-[(1RS, 2RS)-2-(4-Chlorophenyl)-1-methyl-3-{3-(2-naphthyl)phenyl}propyl]-N-(2-naphthylmethyl)carbamoylmethylsuccinic acid $^1$H-NMR(CDCl$_3$+CD$_3$OD)δ: 0.80–1.02(3H, m), 2.40–3.40(8H, m), 4.35–5.00(3H, m), 6.30–7.90(22H, m).

EXAMPLE 89

N-{(1RS, 2RS)-3-(4-Biphenylyl)-2-(3,4-dichlorophenyl)-1-methylpropyl}-N-(2-naphthylmethyl)carbamoylmethylsuccinic acid $^1$H-NMR(CDCl$_3$+CD$_3$OD)δ: 0.95/1.02(3H, each of d, J=6.5 Hz/6.2 Hz), 2.54–3.23(8H, m), 4.56–4.86(2H, m), 4.3–4.4/5.0–5.4(1H, m), 6.41–7.89(19H, m).

EXAMPLE 90

N-{(1RS, 2RS)-3-(4-Biphenylyl)-2-(2-naphthyl)-1-methylpropyl}-N-(2-naphthylmethyl)carbamoylmethylsuccinic acid $^1$H-NMR(CDCl$_3$)δ: 0.87–1.04(3H, m), 2.59–3.45(8H, m), 4.55–4.94(2H, m), 6.44–7.92(22H, m).

EXAMPLE 91

Preparation of N-{(1RS, 2SR)-3-(3,4-dichlorophenyl)-1-methyl-2-(2-naphthoyloxy)propyl}carbamoylmethylsuccinic acid 16.2 mg of (1RS, 2SR)-3-(3,4-dichlorophenyl)-1-methyl-2-(2-naphthoyloxy)propylamine, 18.2 mg of di-tert-butyl carboxymethylsuccinate and 7.0 mg of 4-dimethylaminopyridine were dissolved in 10 ml of methylene chloride, and 12.3 mg of 1-ethyl-3-(3-dimethylaminopropyl)carbodiimide hydrochloride was added thereto with stirring under cooling with ice. The mixture was stirred at room temperature overnight. The reaction solution was concentrated under reduced pressure, and then the residue was extracted by an addition of ethyl acetate and water. The organic layer was sequentially washed with 0.5N hydrochloric acid, a saturated sodium hydrogencarbonate aqueous solution and a saturated sodium chloride aqueous solution, and then dried over anhydrous magnesium sulfate. The drying agent was separated by filtration, and then the solvent was distilled off under reduced pressure. The residue was subjected to silica gel thin layer chromatography (Kieselgel™ 60F$_{254}$, Art 5744, manufactured by Merck Co.; hexane/ethyl acetate=2/1) to obtain 14.0 mg (yield: 51%) of a di-tert-butyl ester of the above-identified compound.

14 mg of the ester compound thus obtained was dissolved in 3 ml of methylene chloride, and 0.5 mg of trifluroacetic acid was added thereto. The mixture was stirred at room temperature for 5 hours. The reaction solution was evaporated to dryness under reduced pressure. The residue was treated with hexane to obtain 12.1 mg of the above-identified compound as white solid.

$^1$H-NMR(CDCl$_3$)δ: 1.23(3H, d, J=6.6 Hz), 2.35–2.46(1H, m), 2.59–2.71(3H, m), 2.89–3.00(2H, m), 3.15–3.26(1H, m), 4.20–4.35(1H, m), 5.30–5.41(1H, m), 6.88–7.00(1H, m), 7.01–7.08(1H, m), 7.21–7.26(1H, m), 7.33(1H, br), 7.48–7.60(2H, m), 7.77–7.92(4H, m), 8.45(1H, s).

EXAMPLE 92

Preparation of (2S)-2-[N-{(1S, 2R)-3-(3,4-dichlorophenyl)-1-methyl-2-(2-naphthoyloxy)-propyl}carbamoylmethyl]succinic acid 1.35 g of (1S, 2R)-3-(3,4-dichlorophenyl)-1-methyl-2-(2-naphthoyloxy)propylamine obtained in Example 122 and 1.11 g of di-tert-butyl (2S)-carboxymethylsuccinate obtained in Example 116 were dissolved in 20 ml of methylene chloride, and 0.81 g of 1-ethyl-3-(3-dimethylaminopropyl)carbodiimide hydrochloride and 0.51 g of 4-dimethylaminopyridine were added thereto with stirring under cooling with ice. The mixture was stirred at room temperature for 3 hours. The reaction solution was extracted by an addition of water and methylene chloride. The organic layer was washed with a saturated sodium chloride aqueous solution and then dried over anhydrous magnesium sulfate. The drying agent was separated by filtration, and then the solvent was distilled off under reduced pressure. The residue was subjected to silica gel column chromatography (Wakogel™ C-200, 100 g; hexane/ethyl acetate=3/1→2/1) to obtain 1.87 g (yield: 71%) of a di-tert-butyl ester of the above-identified compound.

1.84 g of the ester compound thus obtained was dissolved in 20 ml of methylene chloride, and 2 ml of trifluoroacetic acid was added thereto. The mixture was stirred at room temperature overnight. The reaction solution was evaporated to dryness under reduced pressure. The residue was recrystallized from a liquid mixture of 15 ml of methanol, 30 ml of chloroform and 100 ml of hexane to obtain 1.15 g (yield: 75%) of the above-identified compound as white needles having a melting point of from 181° to 182° C.

$^1$H-NMR(CD$_3$OD)δ: 1.31(3H, d, J=7.2 Hz), 2.43(1H, dd, J=7.5 Hz, 14.7 Hz), 2.56–2.72(3H, m), 2.99(1H, dd, J=9.0 Hz, 14.1 Hz), 3.07(1H, dd, J=4.5 Hz, 14.1 Hz), 3.20(1H, quint., J=6.6 Hz), 4.24–4.33(1H, m), 5.45(1H, quint., J=4.5 Hz), 7.20(1H, dd, J=2.4 Hz, 8.4 Hz), 7.32(1H, d, J=S.4 Hz), 7.48(1H, d, J=1.8 Hz), 7.53–7.64(2H, m), 7.89–8.01(4H, m), 8.22(1H, d, J=8.7 Hz), 8.54(1H, s).

Compounds of Examples 93 to 95 were prepared in the same manner as in Example 92 except that (1S, 2R)-3-(3,4-dichlorophenyl)-1-methyl-2-(2-naphthoyloxy)propylamine used as the starting material in the above reaction was changed to the corresponding amine derivatives.

EXAMPLE 93

(2S)-2-[N-{(1S, 2.R)-3-(3,4-Dichlorophenyl)-1-methyl-2-(2-naphthoyloxy)-propyl}-N-methylcarbamoylmethyl]succinic acid mp 71°–74° C.

$^1$H-NMR(CD$_3$OD)δ: 1.29, 1.38(total 3H, each d, J=6.6 Hz, 6.9 Hz), 2.50–3.10(6H, m), 2.83, 2.94(total 1H, s), 3.24–3.35(1H, m), 4.25–4.32, 4.72–4.82(total 1H, m), 5.50–5.60(1H, m), 7.18, 7.22(total 1H, each dd, J=2.0 Hz, 8.1 Hz/1.8 Hz, 8.4 Hz), 7.44, 7.48(total 1H, each d, J=2.0 Hz, 1.8 Hz), 7.54–7.68(2H, m), 7.90–8.06(4H, m), 8.56, 8.61(total 1H, br).

EXAMPLE 94

(2S)-2-[N-{(1S, 2R)-2-(4-Chloro-3-methylbenzoyloxy)-3-(3,4-dichlorophenyl)-1-methylpropyl}carbamoylmethyl]succinic acid mp 172°–173° C.

$^1$H-NMR(CD$_3$OD)δ: 1.23(3H, d, J=6.6 Hz), 2.41(3H, s), 2.41(1H, dd, J=7.5 Hz, 14.4 Hz), 2.53–2.69(3H, m), 2.93(1H, dd, J=9.6 Hz, 14.1 Hz), 3.03(1H, dd, J=3.6 Hz, 14.1 Hz), 3.16–3.20(1H, m), 4.24(1H, dq, J=4.5 Hz, 6.9 Hz), 5.36(1H, dt, J=4.5 Hz, 9.3 Hz), 7.17(1H, d, J=5.7 Hz), 7.74(1H, dd, J=1.8 Hz, 8.4 Hz), 7.84(1H, d, J=1.8 Hz).

EXAMPLE 95

(2S)-2-[N-{(1S, 2R)-3-(3,4-Dichlorophenyl)-1-methyl-2-(2-quinolinecarbonyloxy)propyl}-carbamoylmethyl]succinic acid mp 111°–114° C.

$^1$H-NMR(CD$_3$OD)δ: 1.35(3H, d, J=6.6 Hz), 2.45–2.72 (4H, m), 3.01–3.21(3H, m), 4.45(1H, m), 5.50(1H, m), 7.27(1H, dd, J=1.8 Hz, 7.2 Hz), 7.36(1H, d, J=7.2 Hz), 7.54(1H, d, J=1.8 Hz), 7.92(1H, m), 8.09(1H, m), 8.24(1H, br.d, J=7.8 Hz), 8.34(1H, d, J=8.4 Hz), 8.39(1H, br.d, J=8.4 Hz), 8.98(1H, br.d, J=8.4 Hz).

EXAMPLE 96

Preparation of (3R)-4-{(1S, 2R)-3-(3,4-dichlorophenyl)-1-methyl-2-(2-naphthoyloxy)-propylcarbamoyl}-3-methylbutanoic acid 233 mg of (1S, 2R)-3-(3,4-dichlorophenyl)-1-methyl-2-(2-naphthoyloxy)propylamine and 103 mg of methyl (R)-3-methylglutarate were dissolved in 15 ml of methylene chloride, and 127 mg of 1-ethyl-3-(3-dimethylaminopropyl)carbodiimide hydrochloride and 60 mg of 4-dimethylaminopyridine were added thereto with stirring under cooling with ice. The mixture was stirred at room temperature overnight. The reaction solution was extracted by an addition of water and ethyl acetate. The organic layer was washed with a saturated sodium chloride aqueous solution and then dried over anhydrous magnesium sulfate. The drying agent was separated by filtration, and then the solvent was distilled off under reduced pressure. The residue was subjected to silica gel column chromatography (Wakogel™ C-200, 40 g; hexane/ethyl acetate=2/1→1/1) to obtain 269 mg (yield: 85%) of a methyl ester of the above-identified compound.

63 mg of the methyl ester compound thus obtained was added to a liquid mixture of 2.5 ml of concentrated hydrochloric acid and 5 ml of acetic acid. The mixture was stirred at room temperature overnight. The reaction solution was subjected to liquid separation by an addition of water and ethyl acetate. The organic layer was washed with a saturated sodium chloride aqueous solution and then dried over anhydrous magnesium sulfate. The drying agent was separated by filtration, and then the solvent was distilled off under reduced pressure. The residue was subjected to silica gel thin layer chromatography (Kieselgel™ 60F$_{254}$, Art 5744, manufactured by Merck Co.; methylene chloride/methanol=9/1) to obtain 50 mg (yield: 80%) of the above-identified compound as white crystalline powder having a melting point of from 122° to 128° C.

$^1$H-NMR(CDCl$_3$+CD$_3$OD)δ: 1.05(3H, d, J=6.3 Hz), 1.30(3H, d, J=6.9 Hz), 2.13–2.30(2H, m), 2.30–2.46(3H, m), 2.98(1H, dd, J=5.6 Hz, 14.4 Hz), 3.06(1H, dd, J=8.4 Hz, 14.4 Hz), 4.30–4.40(1H, m), 5.35–5.43(1H, m), 6.21(1H, br.d, J=8.4 Hz), 7.13(1H, dd, J=1.8 Hz, 8.1 Hz), 7.31(1H, d, J=8.1 Hz), 7.39(1H, d, J=1.8 Hz), 7.53–7.65(2H, m), 7.86–7.92(2H, m), 7.93–7.99(2H, m), 8.52(1H, s).

EXAMPLE 97

Preparation of (3S)-4-{(1S, 2R)-3-(3,4-dichlorophenyl)-1-methyl-2-(2-naphthoyloxy)propylcarbamoyl}-3-methylbutanoic acid The reaction was carried out in the same manner as in Example 96 using as starting materials (1S, 2R)-3-(3,4-dichlorophenyl)-1-methyl-2-(2-naphthoyloxy)propylamine and tert-butyl (S)-3-methylglutarate (which was prepared by tert-butyl esterifying methyl (R)-3-methylglutarate by means of tert-butanol, 1-ethyl-3-(3-dimethylaminoethylpropyl)carbodiimide hydrochloride and 4-dimethylaminopyridine and then partially hydrolyzing the obtained diester in a 25% aqueous methanol solution of 0.5N sodium hydroxide), to obtain a tert-butyl ester of the above-identified compound.

103 mg of the ester compound thus obtained was dissolved in 5 ml of methylene chloride, and 0.5 ml of trifluroacetic acid was added thereto. The mixture was stirred at room temperature overnight. The reaction solution was evaporated to dryness under reduced pressure, and the residue was subjected to silica gel thin layer chromatography (Kieselgel™ 60F$_{254}$, Art 5744, manufactured by Merck Co.; chloroform/methanol=9/1) to obtain 65 mg (yield: 70%) of the above-identified compound as white crystalline powder having a melting point of from 170° to 172° C.

$^1$H-NMR(CDCl$_3$)δ: 1.03(3H, d, J=6.3 Hz), 1.29(3H, d, J=6.9 Hz), 2.10(1H, dd, J=7.0 Hz, 14.0 Hz), 2.21–2.46(3H, m), 2.95–3.05(2H, m), 4.24–4.40(1H, m), 5.30–5.40(1H, m), 7.12(1H, dd, J=2.0 Hz, 8.1 Hz), 7.29(1H, d, J=8.1 Hz), 7.38(1H, d, J=2.0 Hz), 7.53–7.64(2H, m), 7.84–8.00(4H, m), 8.51(1H, br).

Compounds of Examples 98 and 99 were prepared in the same manner as in Example 97 except that (S)-3-methylglutaric acid used as the starting material in the above reaction was changed to mono-tert-butyl adipate or (E)-5-tert-butoxycarbonyl-4-pentenoic acid.

EXAMPLE 98

5-{(1S, 2R)-3-(3,4-Dichlorophenyl)-1-methyl-2-(2-naphthoyloxy)propylcarbamoyl}-pentanoic acid mp 73°–75° C.

$^1$H-NMR(CDCl$_3$)δ: 1.28(3H, d, J=6.6 Hz), 1.58–1.76(4H, m), 2.15–2.24(2H, m), 2.29–2.40(2H, m), 2.92–3.12(2H, m), 4.30–4.40(1H, m), 5.32–5.42(1H, m), 6.06(1H, br.d, J=8.2 Hz), 7.13(1H, dd, J=2.0 Hz, 8.2 Hz), 7.30(1H, d, J=8.2 Hz), 7.39(1H, d, J=2.0 Hz), 7.52–7.66(2H, m), 7.85–8.01(4H, m), 8.52(1H, br).

EXAMPLE 99

(2E)-5-{(1S, 2R)-3-(3,4-Dichlorophenyl)-1-methyl-2-(2-naphthoyloxy)propylcarbamoyl}-2-pentenoic acid mp 72°–75° C.

¹H-NMR(CD₃OD)δ: 1.28(3H, d, J=6.9 Hz), 2.31(2H, t, J=7.5 Hz), 2.57(2H, q, J=6.9 Hz), 2.97(1H, dd, J=5.4 Hz, 14.7 Hz), 3.06(1H, dd, J=8.4 Hz, 14.1 Hz), 4.32–4.37(1H, m), 5.35–5.41(1H, m), 5.85(1H, d, J=15.6 Hz), 6.00(1H, d, J=8.4 Hz), 7.03(1H, dt, J=6.6 Hz, 15.6 Hz), 7.12(1H, dd, J=1.8 Hz, 8.4 Hz), 7.31(1H, d, J=8.4 Hz), 7.39(1H, d, J=1.8 Hz), 7.54–7.64(2H, m), 7.89(2H, d, J=8.7 Hz), 7.95–7.99(2H, m), 8.52(1H, s).

EXAMPLE 100

Preparation of 4-{(1S, 2R)-3-(3,4-dichlorophenyl)-1-methyl-2-(2-naphthoyloxy)-propylcarbamoyl}-3-methoxybutanoic acid 162 mg of 3-methoxyglutaric acid was dissolved in 3 ml of acetone, and 206 mg of N,N'-dicyclohexylcarbodiimide was added thereto. The mixture was stirred at room temperature for 2 hours. The precipitate formed in the reaction solution was separated by filtration, and then the solvent was distilled off under reduced pressure. The residue was dissolved in 5 ml of methylene chloride, and then 106 mg of (1S, 2R)-3-(3,4-dichlorophenyl)-1-methyl-2-(2-naphthoyloxy)propylamine hydrochloride and 209 μl of triethylamine were added thereto with stirring under cooling with ice. The mixture was stirred for one hour under cooling with ice. The reaction solution was extracted by an addition of 1N hydrochloric acid and methylene chloride. The organic layer was washed with a saturated sodium chloride aqueous solution and then dried over anhydrous magnesium sulfate. The drying agent was separated by filtration, and then the solvent was distilled off under reduced pressure. The residue was subjected to silica gel thin layer chromatography (Kieselgel™ 60F₂₅₄, Art 5744, manufactured by Merck Co.; methylene chloride/methanol=10/1) to obtain 31 mg of the above-identified compound as white powder.

¹H-NMR(CD₃OD)δ: 1.31(3H, d, J=6.9 Hz), 2.42–2.69(4H, m), 2.94–3.10(2H, m), 3.26(3/2H, s), 3.27(3/2H, s), 3.91–3.99(1H, m), 4.32–4.41(1H, m), 5.38–5.45(1H, m), 6.57–6.74(1H, m), 7.12(1H, dd, J=2.1 Hz, 8.1 Hz), 7.30(1H, d, J=8.1 Hz), 7.38(1H, d, J=1.8 Hz), 7.53–7.64(2H, m), 7.88(2H, d, J=8.4 Hz), 7.95–7.99(2H, m), 8.52(1H, s).

EXAMPLE 101

Preparation of 4-{(1S, 2R)-3-(3,4-dichlorophenyl)-1-methyl-2-(2-naphthoyloxy)-propylcarbamoyl}-3-hydroxybutanoic acid 129 mg of (1S, 2R)-3-(3,4-dichlorophenyl)-1-methyl-2-(2-naphthoyloxy)propylamine hydrochloride and 120 μl of triethylamine were dissolved in 15 ml of methylene chloride, and 82 mg of 3-(tert-butyldimethylsilyloxy)glutaric anhydride was added thereto with stirring under cooling with ice. The mixture was stirred at room temperature for 3 hours. The reaction solution was extracted by an addition of 1N hydrochloric acid and methylene chloride. The organic layer was dried over anhydrous magnesium sulfate. The drying agent was separated by filtration, and the solvent was distilled off under reduced pressure. The residue was dissolved in a liquid mixture of 10 ml of tetrahydrofuran and 5 ml of 1N hydrochloric acid, and the solution was left to stand at room temperature overnight. The reaction solution was extracted by an addition of water and ethyl acetate. The organic layer was washed with a saturated sodium chloride aqueous solution and then dried over anhydrous magnesium sulfate. The drying agent is separated by filtration, and then the solvent was distilled off under reduced pressure. The residue was subjected to silica gel thin layer chromatography (Kieselgel™ 60F₂₅₄, Art 5744, manufactured by Merck Co.; chloroform/methanol=6/1) to obtain 112 mg (yield: 71%) of the above-identified compound as white powder.

¹H-NMR(CD₃OD)δ: 1.30(3H, d, J=6.9 Hz), 2.47–2.58(4H, m), 3.01(1H, dd, J=9.0 Hz, 14.1 Hz), 3.09(1H, dd, J=4.4 Hz, 14.1 Hz), 4.26–4.35(1H, m), 4.35–4.37(1H, m), 5.39–5.48(1H, m), 7.20(1H, dd, J=1.8 Hz, 8.1 Hz), 7.31(1H, d, J=8.1 Hz), 7.47(1H, d, J=1.8 Hz), 7.53–7.64(2H, m), 7.89–8.03(4H, m), 8.55(1H, br).

EXAMPLE 102

Preparation of N-{(1RS, 2RS, 3E)-2-(3,4-dichlorobenzyl)-1-methyl-4-(2-naphthyl)-3-butenyl}carbamoylmethylsuccinic acid 28 mg of (1RS, 2RS, 3E)-2-(3,4-dichlorobenzyl)-1-methyl-4-(2-naphthyl)-3-butenylamine and 13 μl of N-ethyldiisopropylamine were dissolved in 1 ml of tetrahydrofuran, and this solution was dropwise added into a tetrahydrofuran solution (1 ml) of 16 mg of chloroformylmethylsuccinic anhydride with stirring under cooling with ice. The mixture was stirred for 2 hours under cooling with ice. The reaction solution was extracted by an addition of a 5% oxalic acid aqueous solution and ethyl ether. The organic layer was washed with a saturated sodium chloride aqueous solution and then dried over anhydrous magnesium sulfate. The drying agent was separated by filtration, and then the solvent was distilled off under reduced pressure. The residue was subjected to silica gel column chromatography (Wakogel™ C-200, 3 g; chloroform→chloroform/methanol =10/1) to obtain 20 mg (yield: 58%) of the above-identified compound as white powder.

¹H-NMR(CDCl₃+CD₃OD)δ: 1.15(3H, d, J=6.9 Hz), 2.32–2.42(1H, m), 2.55–2.80(6H, m), 3.19–3.27(1H, m), 4.02–4.15(1H, m), 6.02(1H, dd, J=7.7 Hz, 15.8 Hz), 6.15–6.25(1H, m), 6.34(1H, d, J=15.8 Hz), 6.94(1H, dd, J=2.1 Hz, 8.5 Hz), 7.26(2H, s), 7.36–7.45(2H, m), 7.48(1H, d, J=8.6 Hz), 7.59(1H, s), 7.72–7.77(3H, m).

Compounds of Examples 103 to 106 were prepared in the same manner as in Example 102 except that (1RS, 2RS, 3E)-2-(3,4-dichlorobenzyl)-1-methyl-4-(2-naphthyl)-3-butenylamine used as the starting material in the above reaction was changed to the corresponding amine compounds.

EXAMPLE 103

N-{(1RS, 2RS, 3E)-4-(2-Benzo[b]furanyl)-2-(3,4-dichlorobenzyl)-1-methyl-3-butenyl}carbamoylmethylsuccinic acid ¹H-NMR(CD₃OD)δ: 1.10–1.25(3H, m), 2.40–3.10(7H, m), 3.15–3.30(1H, m), 6.10–6.35(2H, m), 6.52(1H, s), 7.05–7.52(7H, m).

EXAMPLE 104

N-[(1RS, 2RS, 3E)-2-(3,4-Dichlorobenzyl)-1-methyl-4-{3-(3-thienyl)-phenyl}-3-butenyl]carbamoylmethylsuccinic acid ¹H-NMR(CDCl₃+CD₃OD)δ: 1.10–1.20(3H, m), 2.30–2.80(7H, m), 3.10–3.30(1H, m), 4.00–4.20(1H, m), 5.94(1H, dd, J=8.1 Hz, 15.2 Hz), 6.16–6.23(1H, br), 6.22(1H, d, J=15.2 Hz), 6.91–6.98(2H, m), 7.21–7.24(2H, m), 7.30–7.46(6H, m).

EXAMPLE 105

N-{(1RS, 2RS, 3E)-2-(3,4-Dichlorobenzyl)-1-methyl-4-(1-naphthyl)-3-butenyl}carbamoylmethylsuccinic acid $^1$H-NMR(CDCl$_3$+CD$_3$OD)δ: 1.15–1.18(3H, m), 2.30–2.95(7H, m), 4.05–4.21 (1H, m), 6.09 (1H, dd, J=8.0 Hz, 16.1 Hz), 7.10(2H, d, J=8.4 Hz), 7.19(2H, d, J=7.1 Hz), 7.38–7.50 (2H, m), 7.51(1H, d, J=8.2 Hz), 7.62(1H, s), 7.70–7.83(3H, m).

EXAMPLE 106

N-{(1RS, 2RS, 3E)-2-(4-Chlorobenzyl)-4-(4-chlorophenyl)-1-methyl-3-butenyl}-carbamoylmethylsuccinic acid $^1$H-NMR(CD$_3$OD)δ: 1.13(3/2H, d, J=6.8 Hz), 1.15(3/2H, d, J=6.8 Hz), 2.37–2.75(1H, m), 2.85–2.90(1H, m), 3.18–3.27(1H, m), 3.92–4.03(1H, m), 5.95–6.15(2H, m), 7.09–7.30(8H, m).

EXAMPLE 107

Preparation of N-{(1RS, 2SR)-2-(3,4-dichlorobenzyl)-1-methyl-3-(2-naphthoxy)-propyl}carbamoylmethylsuccinic acid 33 mg of N-{(1RS, 2SR)-2-(3,4-dichlorobenzyl)-1-methyl-3-(2-naphthoxy)propyl}phthalimide was dissolved in 3 ml of ethanol, and 0.1 ml of hydrazine monohydrate was added thereto. The mixture was refluxed under heating for 4 hours. The reaction solution was concentrated under reduced pressure. Then, the residue was dissolved in methylene chloride. Insoluble matters were separated by filtration. Then, the filtrate was again evaporated to dryness under reduced pressure. The residue was dissolved in 3 ml of methylene chloride, and 33 mg of di-tert-butyl carboxymethylsuccinate, 14 mg of 4-dimethylaminopyridine and 22 mg of 1-ethyl-3-(3-dimethylaminopropyl)carbodiimide hydrochloride were added thereto. The mixture was stirred at room temperature overnight. The reaction solution was diluted with ethyl acetate, then sequentially washed with 1N hydrochloric acid, a saturated sodium hydrogencarbonate aqueous solution and a saturated sodium chloride aqueous solution, and dried over anhydrous magnesium sulfate. The drying agent was separated by filtration, and then the solvent was distilled off under reduced pressure. The residue was subjected to silica gel column chromatography (Wakogel™ C-200, 5 g; hexane/ethyl acetate=5/1→3/1) to obtain 52 mg (yield: 93%) of a di-tert-butyl ester of the above-identified compound as colorless oily substance.

52 mg of the ester compound thus obtained was dissolved in 1 ml of methylene chloride, and 1 ml of trifluoroacetic acid was added thereto. The mixture was stirred at room temperature for 2 hours. The reaction solution was concentrated under reduced pressure. Then, toluene was added to the residue, and the mixture was again evaporated to dryness under reduced pressure. The obtained product was treated with a liquid mixture of methylene chloride and hexane to obtain 31 mg (yield: 72%) of the above-identified compound as white powder.

$^1$H-NMR(CDCl$_3$+CD$_3$OD)δ: 1.24(3H, d, J=6.8 Hz), 2.20–2.30(1H, m), 2.47(1H, dd, J=5.9 Hz, 14.9 Hz), 2.59–2.87(5H, m), 3.18–3.28(1H, m), 3.92–4.02(2H, m), 4.21–4.31(1H, m), 7.02(1H, d, J=2.5 Hz), 7.06(1H, dd, J=2.0 Hz, 8.3 Hz), 7.11(1H, dd, J=2.3 Hz, 9.0 Hz), 7.31–7.36(3H, m), 7.43(1H, dt, J=1.0 Hz, 8.0 Hz), 7.68(1H, d, J=8.0 Hz), 7.74(1H, d, J=8.8 Hz), 7.76(1H, d, J=7.5 Hz).

Compounds of Examples 108 to 111 were prepared in the same manner as in Example 107 except that N-{(1RS, 2SR)-2-(3,4-dichlorobenzyl)-1-methyl-3-(2-naphthoxy)propyl}phthalimide used as the starting material in the above reaction was changed to the corresponding phthalimide derivatives.

EXAMPLE 108

N-{(1RS, 2SR)-2-(4-Chlorobenzyl)-3-(4-chlorophenoxy)-1-methylpropyl}-carbamoylmethylsuccinic acid $^1$H-NMR(CD$_3$OD)δ: 1.20(3H, d, J=6.9 Hz), 2.08–2.17(1H, m), 2.38–2.52(2H, m), 2.53–2.75(4H, m), 2.82–2.93(1H, m), 3.15–3.25(1H, m), 3.78(1H, br.dd, J=5.0 Hz, 9.6 Hz), 3.85(1H, br.dd, J=4.2 Hz, 9.6 Hz), 4.13–5.03(1H, m), 6.82(2H, br.d, J=9.3 Hz), 7.15–7.24(6H, m).

EXAMPLE 109

N-{(1RS, 2SR)-2-(3,4-Dichlorobenzyl)-1-methyl-3-(2-naphthylthio)-propyl}carbamoylmethylsuccinic acid $^1$H-NMR (CDCl$_3$+CD$_3$OD)δ: 1.19(3H, d, J=6.8 Hz), 1.98–2.08(1H, m), 2.43(1H, dt, J=6.0 Hz, 15.2 Hz), 2.58–2.80(5H, m), 2.93 (2H, d, J=6.3 Hz), 3.14–3.24(1H, m), 4.27–4.37(1H, m), 6.98(1H, dd, J=2.0 Hz, 8.0 Hz), 7.23–7.31(3H, m), 7.40–7.50(3H, m), 7.61(1H, br.d, J=8.0 Hz), 7.68(1H, br.d, J=9.0 Hz), 7.77(1H, br.d, J=9.0 Hz).

EXAMPLE 110

N-{(1RS, 2RS)-2-(4-Chlorobenzyl)-4-(4-chlorophenyl)-1-methylbutyl}carbamoylmethylsuccinic acid $^1$H-NMR(CD$_3$OD)δ: 1.08(3/2H, d, J=6.6 Hz), 1.15(3/2H, d, J=6.6 Hz), 1.31–1.90(3H, m), 2.20–2.83(8H, m), 3.10–3.40(1H, m), 6.95–7.40(8H, m).

EXAMPLE 111

N-{(1RS, 2SR)-3-(3,4-Dichlorophenyl)-1-methyl-2-(2-naphthylmethyloxy)propyl}-carbamoylmethylsuccinic acid $^1$H-NMR(CDCl$_3$+CD$_3$OD)δ: 1.17(3H, d, J=6.3 Hz), 1.75(1/2H, m), 1.93(1/2H, m), 2.27–2.50(2H, m), 2.58–2.85(3H, m), 2.94–3.09(1H, m), 3.61–3.70(1H, m), 3.98–4.09(1H, m), 4.30(1H, br.d, J=12.3 Hz), 4.54–4.52(1H, m), 5.78–5.87(1H, m), 7.03–7.08(1H, br.dd, J=1.8 Hz, 8.1 Hz), 7.27–7.36(3H, m), 7.45–7.52(2H, m), 7.58(1H, br), 7.76–7.84(3H, m).

EXAMPLE 112

Preparation of 4-{(1RS, 2RS, 3E)-2-(3,4-dichlorobenzyl)-1-methyl-4-(2-naphthyl)-3-butenylcarbamoyl}-3-methylbutanoic acid 20 mg of (1RS, 2RS, 3E)-2-(3,4-dichlorobenzyl)-1-methyl-4-(2-naphthyl)-3-butenylamine was dissolved in 1 ml of methylene chloride, and 10 mg of 3-methylglutaric anhydride and 4 μl of triethylamine were added thereto. The mixture was stirred at room temperature for 3 hours. A saturated sodium carbonate aqueous solution and methylene chloride were added to the reaction solution, and the mixture was stirred for 30 minutes. Then, the organic layer was collected by separation, washed with 1N hydrochloric acid and a saturated sodium chloride aqueous solution and then dried over anhydrous magnesium sulfate. The drying agent was separated by filtration, and then the solvent was distilled off under reduced pressure. The residue was subjected to silica gel column chromatography (Wakogel™ C-200, 2 g; chloroform/methanol =20/1) to obtain 16 mg (yield: 74%) of the above-identified compound as colorless oily substance.

$^1$H-NMR(CDCl$_3$)δ: 1.36(3H, d, J=6.0 Hz), 1.20(3H, d, J=6.8 Hz), 2.12–2.45(5H, m), 2.61–2.78(2H, m), 2.83(1H, t, J=8.5 Hz), 4.11–4.22(1H, m), 5.70(1H, br.d, J=7.8 Hz), 6.09(1H, dd, J=9.1 Hz, 15.3 Hz), 6.99(1H, dd, J=1.9 Hz, 8.5 Hz), 7.28(2H, s), 7.50(1H, dd, J=1.9 Hz, 8.5 Hz), 7.61(1H, s), 7.76–7.79(3H, m).

EXAMPLE 113

Preparation of 5-{(1RS, 2RS, 3E)-2-(3,4-dichlorobenzyl)-1-methyl-4-(2-naphthyl)-3-butenylcarbamoyl}pentanoic acid 30 mg of (1RS, 2RS, 3E)-2-(3,4-dichlorobenzyl)-1-methyl-4-(2-naphthyl)-3-butenylamine was dissolved in 1 ml of methylene chloride, and 18 mg of mono-ethyl adipate, 12 mg of 4-dimethylaminopyridine and 19 mg of 1-ethyl-3-(3-dimethylaminopropyl)carbodiimide hydrochloride were added thereto. The mixture was stirred at room temperature for 3 hours. The reaction solution was diluted with ethyl acetate, then sequentially washed with 1N hydrochloric acid, a saturated sodium hydrogencarbonate aqueous solution and a saturated sodium chloride aqueous solution, and dried over anhydrous sodium sulfate. The drying agent was separated by filtration, and then the solvent was distilled off under reduced pressure. The residue was dissolved in 1 ml of methanol, and then 0.5 ml of a 2N sodium hydroxide aqueous solution was added thereto. The mixture was stirred at room temperature for 2 hours. The reaction solution was concentrated under reduced pressure and then extracted by an addition of ethyl ether and 1N hydrochloric acid. The organic layer was washed with a saturated sodium chloride aqueous solution and then dried over anhydrous magnesium sulfate. The drying agent was separated by filtration, and then the solvent was distilled off under reduced pressure. The residue was subjected to silica gel thin layer chromatography (Kieselgel™ 60F$_{254}$, Art 5744, manufactured by Merck Co.; chloroform/methanol=10/1) to obtain 21 mg (yield: 51%) of the above-identified compound as colorless oily substance.

$^1$H-NMR(CDCl$_3$)δ: 1.14(3H, d, J=6.5 Hz), 1.50–1.70(4H, br), 2.05–2.20(2H, br), 2.20–2.35(2H, br), 2.64(2H, t, J=9.9 Hz), 2.83–2.90(1H, m), 3.70–4.50(1H, br), 4.05–4.17(1H, m), 5.90–6.00(1H, br), 6.05(1H, dd, J=8.8 Hz, 15.7 Hz), 7.05(2H, d, J=5.9 Hz), 7.16(2H, d, J=8.3 Hz), 7.36–7.42(2H, m), 7.46(1H, d, J=9.4 Hz), 7.55(1H, s), 7.68–7.80(3H, m).

EXAMPLE 114

Preparation and optical resolution of (1RS, 2RS)-2-(4-biphenyl)-3-(4-chlorophenyl)-1-methylpropylamine (1) Preparation of 1-(4-biphenylyl)-2-propanone 10.5 g of 4-biphenylylacetic acid was dissolved in 50 ml of thionyl chloride, and the solution was heated at 80° C. for 3 hours. Then, excess thionyl chloride was distilled off under reduced pressure. Benzene was added to the residue, and the solvent was again distilled off. This operation was repeated again. Then, the formed acid chloride was dissolved in 100 ml of ethyl ether. Separately, 23.7 g of cuprous iodide was suspended in 50 ml of ethyl ether, and 166 ml of a 1.5M methyllithiumethyl ether solution was added thereto with stirring under cooling with ice to obtain a uniform solution. This solution was dropwise added to the ethyl ether solution of the acid chloride obtained by the above reaction under a nitrogen atmosphere while stirring and cooling to −70° C. After completion of the dropwise addition, the mixture was stirred at the same temperature for further one hour. Then, methanol was added thereto to decompose the excess copper lithium reagent. Ethyl ether and 2N hydrochloric acid were added to the reaction solution. After removing the formed insoluble matters by filtration, the filtrate was subjected to liquid separation. The organic layer was washed with a saturated sodium chloride aqueous solution and then dried over anhydrous magnesium sulfate. The drying agent was separated by filtration, and then the solvent was distilled off under reduced pressure to obtain 9.93 g (yield: 96%) of the above-identified compound as colorless oily substance.

(2) Preparation of 3-(4-biphenylyl)-4-(4-chlorophenyl)-2-butanone 9.93 g of 1-(4-biphenylyl)-2-propanone, 8.4 g of 4-chlorobenzyl chloride and 2.1 g of sodium hydroxide were mixed and heated for 5 hours with stirring on an oil bath of 80° to 90° C. The reaction solution was left to cool to room temperature. Then, ethyl ether and water were added thereto. The organic layer was collected by separation and then dried over anhydrous magnesium sulfate. The drying agent was separated by filtration, and then the solvent was distilled off under reduced pressure. The residue was recrystallized from hexane to obtain 8.42 g (yield: 53%) of the above-identified compound as colorless needles having a melting point of from 107° to 108.5° C.

(3) Preparation of (2RS, 3SR)-3-(4-biphenylyl)-4-(4-chlorophenyl)-2-propanol 8.42 g of 3-(4-biphenylyl)-4-(4-chlorophenyl)-2-butanone was dissolved in 30 ml of tetrahydrofuran, and 30 ml of a 1M tetrahydrofuran solution of lithium tri-sec-butylborohydride (L-selectride™) was added thereto with stirring under cooling to −78° C. The mixture was stirred at the same temperature for 30 minutes. 50 ml of a 2N sodium hydroxide aqueous solution was added to the reaction solution. The mixture was stirred at room temperature for one hour, and then 20 ml of a 30% hydrogen peroxide aqueous solution was added thereto with stirring under cooling with ice. The mixture was stirred for further one hour. The product was extracted by an addition of ethyl ether. The extract solution was washed with a saturated sodium chloride aqueous solution and then dried over anhydrous magnesium sulfate. The drying agent was separated by filtration, and then the solvent was distilled off under reduced pressure. The residue was subjected to medium pressure liquid chromatography (hexane/ethyl acetate=15/1 to 10/1) to obtain 7.36 g (yield: 87%) of the above-identified compound as colorless oily substance.

(4) Preparation of N-{(1RS, 2RS)-2-(4-biphenylyl)-3-(4-chlorophenyl)-1-methylpropyl}phthalimide 7.36 g of (2RS, 3SR)-3-(4-biphenylyl)-4-(4-chlorophenyl)-2-propanol, 11.5 g of triphenylphosphine and 6.5 g of phthalimide were dissolved in 100 ml of tetrahydrofuran, and 20 ml of a tetrahydrofuran solution of 7.66 g of diethyl azodicarboxylate separately prepared was added thereto with stirring under cooling with ice. The mixture was stirred at room temperature overnight. The reaction solution was concentrated under reduced pressure. Then, the residue was extracted by an addition of ethyl ether and water. The organic layer was washed with a saturated sodium chloride aqueous solution and then dried over anhydrous magnesium sulfate. The drying agent was separated by filtration, and then the solvent was distilled off under reduced pressure. The residue was treated with methanol. Then, the precipitate was collected by filtration to obtain 3.08 g (yield: 30%) of the above-identified compound as white crystalline powder having a melting point of from 142° to 144° C.

(5) Preparation of (1RS, 2RS)-2-(4-biphenylyl)-3-(4-chlorophenyl)-1-methylpropylamine hydrochloride 3.08 g of N-(1RS, 2RS)-2-(4-biphenylyl)-3-(4-chlorophenyl)-1-methylpropyl}phthalimide was suspended in ethanol, and 1 ml of hydrazine monohydrate was added thereto. The mixture was refluxed under heating for 4 hours. The reaction solution was left to cool. Then, insoluble matters were separated by filtration. The filtrate was concentrated under reduced pressure. Then, the residue was treated with a hydrogen chloride-methanol solution to obtain 2.44 g (yield: 99%) of the above-identified compound as white needles having a melting point of from 243° to 249° C.

(6) Preparation of (1S, 2S)- and (1R, 2R)-2-(4-biphenylyl)-3-(4-chlorophenyl)-1-methylpropylamine 2.20 g of (1RS, 2RS)-2-(4-biphenylyl)-3-(4-chlorophenyl)-1-methylpropylamine hydrochloride was added to a liquid mixture of 50 ml of ethyl ether and 20 ml of a 2N sodium hydroxide aqueous solution under cooling with ice. The mixture was vigorously shaked. Then, the organic layer was collected by separation. The organic layer was washed with water and a saturated sodium chloride aqueous solution and dried over anhydrous magnesium sulfate. Then, the solvent was distilled under reduced pressure. The residual free base was dissolved in 20 ml of methanol together with 2.22 g of D-(+)-dibenzoyltartaric acid, and seed crystals were added thereto. The mixture was left to stand at room temperature overnight. The precipitated crystals were collected by filtration, washed with ethanol and then dried to obtain 342 mg of a D-(+)-dibenzoyltartarate of a (1S, 2S)-isomer of the above-identified compound, $[\alpha]_D^{20} = +161.7°$ (c=1.5, methanol).

The dibenzoyltartarate compound thus obtained was dissolved in 20 ml of ethyl ether and 10 ml of a 2N sodium hydroxide aqueous solution under cooling with ice. The organic layer was collected by separation and post-treated by a conventional method to obtain 162 mg (yield: 8.2%) of a (1S, 2S)-isomer of the above-identified compound, $[\alpha]_D^{20} = +207°$ (c=1.5, methanol) as colorless oily substance.

Likewise, the filtrate after filtration of the D-(+)-dibenzoyltartarate of the (1S, 2S)-isomer and the washing solution were put together and evaporated to dryness under reduced pressure. Then, ethyl ether and a 2N sodium hydroxide aqueous solution were added to the residue and post-treated by a conventional method to obtain 1.4 g of a free base as a mixture of enantiomers. This base was dissolved in 20 ml of methanol, and 2.22 g of L-(−)-dibenzoyltartaric acid and seed crystals were added thereto. The mixture was subjected to resolution in the same manner as above to obtain 300 mg of a L-(−)-dibenzoyltartarate of a (1R, 2R)-isomer of the above-identified compound, $[\alpha]_D^{20} = -152.4°$ (c=2, methanol), which was an enantiomer of the (1S, 2S)-isomer obtained as described above. The tartarate was dissolved in a liquid mixture of ethyl ether and a 2N sodium hydroxide aqueous solution, and the solution was post-treated by a conventional method to obtain 132 mg (yield: 6.7%) of a (1R, 2R)-isomer of the above-identified compound, $[\alpha]_D^{20} = -185.2°$ (c=1.5, methanol), as colorless oily substance.

The following compounds were prepared in the same manner as in Example 114 except that 4-biphenylylacetic acid and/or 4-chlorobenzyl chloride used in the above reaction were changed to the respective corresponding phenylacetic acid derivatives and/or benzyl halogenide derivatives: (1RS, 2RS)-1-methyl-2,3-diphenylpropylamine, (1RS, 2RS)-2-(4-chlorophenyl)-1-methyl-3-phenylpropylamine, (1RS, 2RS)-3-(4-chlorophenyl)-1-methyl-2-phenylpropylamine, (1RS, 2RS)-2-(4-chlorophenyl)-1-methyl-3-(4-methylphenyl)propylamine, (1RS, 2RS)-2-(4-chlorophenyl)-3-(4-fluorophenyl)-1-methylpropylamine, (1RS, 2RS)-3-(4-biphenylyl)-2-(4-chlorophenyl)-1-methylpropylamine, (1RS, 2RS)-3-(3-chlorophenyl)-2-(4-chlorophenyl)-1-methylpropylamine, (1RS, 2RS)-3-(2-chlorophenyl)-2-(4-chlorophenyl)-1-methylpropylamine, (1RS, 2RS)-2-(4-chlorophenyl)-3-(4-methoxyphenyl)-1-methylpropylamine, (1RS, 2RS)-2-(4-chlorophenyl)-1-methyl-3-(1-naphthyl)propylamine, (1RS, 2RS)-2-(4-chlorophenyl)-1-methyl-3-(2-naphthyl)propylamine, (1RS, 2RS)-3-(4-chlorophenyl)-1-methyl-2-(4-methylphenyl)propylamine, (1RS, 2RS)-2-(4-bromophenyl)-3-(4-chlorophenyl)-1-methylpropylamine, (1RS, 2RS)-3-(4-chlorophenyl)-1-methyl-2-(4-tert-butylphenyl)propylamine, (1RS, 2RS)-3-(4-chlorophenyl)-2-(4-methoxyphenyl)-1-methylpropylamine, (1RS, 2RS)-2-(3-chlorophenyl)-3-(4-chlorophenyl)-1-methylpropylamine, (1RS, 2RS)-3-(4-chlorophenyl)-1-methyl-2-(1-naphthyl)propylamine, (1RS, 2RS)-3-(4-chlorophenyl)-1-methyl-2-(2-naphthyl)propylamine, (1RS, 2RS)-3-(4-chlorophenyl)-2-(4-hydroxyphenyl)-1-methylpropylamine, (1RS, 2RS)-2-(4-chlorophenyl)-3-(3,4-dichlorophenyl)-1-methylpropylamine, (1RS, 2RS)-3-(4-chlorophenyl)-2-(3,4-dichlorophenyl)-1-methylpropylamine, (1RS, 2RS)-2-(3-bromophenyl)-3-(4-chlorophenyl)-1-methylpropylamine, (1RS, 2RS)-2-(4-chlorophenyl)-3-(3,4-difluorophenyl)-1-methylpropylamine, (1RS, 2RS)-2-(4-biphenylyl)-3-(3,4-dichlorophenyl)-1-methylpropylamine, (1RS, 2RS)-2-(4-chlorophenyl)-1-methyl-3-[3-(3-thienyl)phenyl]propylamine, (1RS, 2RS)-2-(4-biphenylyl)-1-methyl-3-(2-naphthyl)propylamine, (1RS, 2RS)-2-(4-chlorophenyl)-1-methyl-3-(4-pyridyl)propylamine, (1RS, 2RS)-2-(4-chlorophenyl)-3-(5-chloro-2-thienyl)-1-methylpropylamine, (1RS, 2RS)-2-(4-chlorophenyl)-1-methyl-3-(8-quinolyl)propylamine, (1RS, 2RS)-3-(7-benzo[b]thienyl)-2-(4-chlorophenyl)-1-methylpropylamine, (1RS, 2RS)-2-(5-benzo[b]thienyl)-3-(4-chlorophenyl)-1-methylpropylamine, (1RS, 2RS)-2-(4-chlorophenyl)-3-(2-fluoro-4-biphenylyl)-1-methylpropylamine, (1RS, 2RS)-3-(4-biphenylyl)-2-(3,4-dichlorophenyl)-1-methylpropylamine and (1RS, 2RS)-3-(4-biphenylyl)-1-methyl-2-(2-naphthyl)propylamine.

EXAMPLE 115

Preparation of (1S, 2S)-2-(4-biphenylyl)-3-(3,4-dichlorophenyl)-1-methylpropylamine 2.44 g (1RS, 2RS)-2-(4-biphenylyl)-3-(3,4-dichlorophenyl)-1-methylpropylamine obtained in the same manner as in Example 114, was dissolved in 15 ml of methanol, and 15 ml of a methanol solution of 0.99 g of L-(+)-tartaric acid and seed crystals were added thereto. The mixture was left to stand at room temperature overnight. Precipitated crystals were collected by filtration and recrystallized twice from 30 ml of methanol and 15 ml of methanol to obtain 360 mg of a L-(+)-tartarate of a (1S, 2S)-isomer of the above-identified compound, $[\alpha]_D^{20}=+150.3°$ (c=1.5, methanol).

The tartarate thus obtained was treated by a conventional method to obtain 238 mg (yield: 9.8%) of the above-identified compound in a free base form, $[\alpha]_D^{20}=+188°$ (c=1.5, methanol), as colorless oily substance.

EXAMPLE 116

Preparation and optical resolution of di-tert-butyl carboxymethylsuccinate 13.1 ml of a 1.5M cyclohexane solution of lithium diisopropylamide was dissolved in 10 ml of tetrahydrofuran, and 10 ml of a tetrahydrofuran solution of 2.96 g of benzyl acetate was added thereto with stirring under cooling to −70° C. The mixture was stirred at the same temperature for 30 minutes. Then, 10 ml of a tetrahydrofuran solution of 2.96 g of di-tert-butyl maleate was dropwise added thereto. The mixture was stirred at the same temperature for 30 minutes. The reaction solution was extracted by an addition of 20 ml of water and 50 ml of ethyl ether. The organic layer was collected by separation, then washed with a saturated sodium chloride aqueous solution and dried over anhydrous magnesium sulfate. The drying agent was separated by filtration, and then the solvent was distilled off under reduced pressure. The residue was dissolved in 50 ml of dioxane, and then 0.4 g of a 10% palladium-carbon catalyst was added thereto, whereupon catalytic reduction was conducted at room temperature under atmospheric hydrogen pressure for 20 hours. The catalyst was separated by filtration, and then the solvent was distilled off under reduced pressure. The residue was treated with hexane. Then, the obtained precipitate was collected by filtration and dried to obtain 3.02 g (yield: 85%) of the above-identified compound as white crystalline powder having a melting point of from 55° to 57° C.

12.97 g of the di-tert-butyl ester thus obtained and 13.24 g of cinchonidine were dissolved in 1 l of carbon tetrachloride under heating. Then, seed crystals were added thereto, and the mixture was left to stand at room temperature for 24 hours. The crystals were collected by filtration and then dissolved again with heating in 1 l of carbon tetrachloride. The operation of adding seed crystals and leaving the mixture at room temperature for 24 hours, was further repeated twice, to obtain 6.66 g (yield: 25%) of a cinchonidine salt of a (S)-isomer of the above-identified compound, $[\alpha]_D^{20}=-62.7°$ (c=1.0, chloroform)

The cinchonidine salt thus obtained was dissolved in a liquid mixture of ethyl ether and 1N hydrochloric acid under cooling with ice. The organic layer was collected by separation and post-treated by a conventional method to obtain a (S)-isomer of the above identified compound, $[\alpha]_D^{20}=+4.44°$ (C=0.92, chloroform), as colorless oily substance.

The fraction containing a large amount of another enantiomer, obtained by the above optical resolution operation was converted to free acid, and the same operation was conducted in isopropyl ether by means of quinine, to obtain a (R)-isomer of the above-identified compound as an enantiomer.

EXAMPLE 117

Preparation of (1RS, 2RS)-3-(4-chlorophenyl)-1-methyl-2-[4-(3-thienyl)-phenyl]propylamine 113 mg of N-{(1RS, 2RS)-2-(4-bromophenyl)-3-(4-chlorophenyl)-1-methylpropyl}phthalimide prepared in the same manner as in Example 114, was dissolved in 3 ml of toluene, and 99 mg of tributyl(3-thienyl)tin and 14 mg of tetrakis(triphenylphosphine)palladium (0) were added thereto. The mixture was refluxed under heating for 3 hours in a light-shielding nitrogen atmosphere. The reaction solution was left to cool to room temperature. Then, 2 ml of a 5% potassium fluoride aqueous solution was added thereto, and the mixture was stirred for 30 minutes. Insoluble matters were separated by filtration. Then, ethyl acetate and water were added to the filtrate for liquid separation. The organic layer was collected by separation, washed with a saturated sodium chloride aqueous solution and then dried over anhydrous magnesium sulfate. The drying agent was separated by filtration, and then the solvent was distilled off under reduced pressure. The residue was subjected to silica gel column chromatography (hexane/ethyl acetate=100/1→30/1) to obtain 83 mg of N-[(1RS, 2RS)-3-(4-chlorophenyl)-1-methyl-2-{4-(3-thienyl)phenyl}propyl]phthalimide.

The cross-coupling product thus obtained was suspended in 4 ml of ethanol, and 0.1 ml of hydrazine monohydrate was added thereto. The mixture was heated under reflux for 5 hours. The reaction solution was evaporated to dryness under reduced pressure. Then, the residue was dissolved in 10 ml of methylene chloride. Insoluble matters were separated by filtration, and then the solvent was evaporated to dryness under reduced pressure to obtain 56 mg (yield: 68%) of the above-identified compound as colorless oily substance. The following compounds were prepared in the same manner as in Example 117 using the corresponding phenyl bromide derivatives and/or aromatic stannane derivatives instead of N-{(1RS, 2RS)-2-(4-bromophenyl)-3-(4-chlorophenyl)-1-methylpropyl}phthalimide and/or tributyl(3-thienyl)tin used in the above reaction: (1RS, 2RS)-2-(4'-chloro-4-biphenylyl)-3-(4-chlorophenyl)-1-methylpropylamine, (1RS, 2RS)-3-(4-chlorophenyl)-1-methyl-2-{4-(3-pyridyl)phenyl}propylamine, (1RS, 2RS)-2-(3'-chloro-4-biphenylyl)-3-(4-chlorophenyl)-1-methylpropylamine, (1RS, 2RS)-2-(3-biphenylyl)-3-(4-chlorophenyl)-1-methylpropylamine, (1RS, 2RS)-3-(4-chlorophenyl)-1-methyl-2-{4-(2-naphthyl)phenyl}propylamine, (1RS, 2RS)-3-(4-chlorophenyl)-2-{4-(2-furyl)phenyl}-1-methylpropylamine, (1RS, 2RS)-3-(4-chlorophenyl)-1-methyl-2-(3', 4'-methylenedioxy-4-biphenylyl)propylamine, (1RS, 2RS)-3-(3-biphenylyl)-2-(4-chlorophenyl)-1-methylpropylamine, (1RS, 2RS)-3-(4'-chloro-4-biphenylyl)-2-(4-chlorophenyl)-1-methylpropylamine, (1RS, 2RS)-2-(4-chlorophenyl)-3-(6-fluoro-3-biphenylyl)-1-methylpropylamine and (1RS, 2RS)-2-(4-chlorophenyl)-1-methyl-3-[3-(2-naphthyl)phenyl]propylamine.

EXAMPLE 118

Preparation of (1RS, 2RS)-3-(4-chlorophenyl)-2-(2'-fluoro-4-biphenylyl)-1-methylpropylamine 0.70 g of (1RS, 2SR)-2-(4-bromophenyl)-3-(4-chlorophenyl)-1-methylpropanol was dissolved in 7 ml of dimethylformamide, and 0.34 g of tert-butyldimethylchlorosilane and 0.18 g of imidazole were added thereto. The mixture was stirred at room temperature overnight. The reaction solution was poured into a saturated sodium hydrogencarbonate aqueous solution and extracted by an addition of ethyl ether. Then, the organic layer was washed with a saturated sodium chloride aqueous solution and then dried over anhydrous magnesium sulfate. The drying agent was separated by filtration, and then the solvent was distilled off under reduced pressure. The residue was subjected to silica gel column chromatography (hexane) to obtain 0.70 g (yield: 75%) of [(2RS, 3SR)-3-(4-bromophenyl)-2-(tert-butyldimethylsilyloxy)-4-(4-chlorophenyl)butane as colorless oily substance.

0.35 g of the silyloxy compound thus obtained was dissolved in 4 ml of ethyl ether, and 0.5 ml of a 1.64M hexane solution of n-butyllithium was dropwise added thereto with stirring in a nitrogen atmosphere while cooling to −78° C. The temperature of the reaction solution was raised to 0° C. Then, 0.22 ml of tri-n-butylchlorosilane was added thereto, and the mixture was stirred at 0° C. for 30 minutes and then at room temperature for 30 minutes. The reaction solution was sequentially washed with a saturated ammonium chloride aqueous solution and a saturated sodium chloride aqueous solution and then dried over anhydrous magnesium sulfate. The drying agent was separated by filtration, and then the solvent was distilled off under reduced pressure. The residue was subjected to silica gel column chromatography (hexane) to obtain 0.39 g (yield: 76%) of (2RS, 3SR)-3-(4-tributylstannylphenyl)-2-(tert-butyldimethylsilyloxy)-4-(4-chlorophenyl)butane as colorless oily substance.

133 mg of the stannane derivative thus obtained was dissolved in 3 ml of toluene, and 42 mg of o-bromofluorobenzene and 12 mg of tetrakis(triphenylphosphine)palladium (0) were added thereto. The mixture was refluxed under heating for 2 hours in a nitrogen atmosphere. The reaction solution was left to cool to room temperature, and then 1.5 ml of a saturated potassium fluoride aqueous solution was added thereto. The mixture was stirred for 30 minutes, and insoluble matters were separated by filtration. The filtrate was extracted by an addition of ethyl acetate and water. The organic layer was collected by separation, then washed with a saturated sodium chloride aqueous solution and dried over anhydrous magnesium sulfate. The drying agent was separated by filtration, and then the solvent was distilled off under reduced pressure. The residue was subjected to silica gel column chromatography (hexane/ethyl acetate=50/1) to obtain 75 mg (yield: 80%) of (2RS, 3SR)-2-(tert-butyldimethylsilyloxy)-4-(4-chlorophenyl)-2-(2'-fluoro-4-biphenylyl)butane as colorless oily substance.

75 mg of the biphenyl compound thus obtained was dissolved in 2 ml of tetrahydrofuran, and 0.60 ml of a 1.0M tetrahydrofuran solution of tetra-n-butylammonium fluoride was added thereto. The mixture was stirred at room temperature for 4 hours. The reaction solution was poured into ice water and extracted by an addition of ethyl acetate. Then, the organic layer was washed with a saturated sodium chloride aqueous solution and then dried over anhydrous magnesium sulfate. The drying agent was separated by filtration, and then the solvent was distilled off under reduced pressure. The residue was subjected to silica gel column chromatography (hexane/ethyl acetate=10/1), to obtain 58 mg of (2RS, 3SR)-4-(4-chlorophenyl)-3-(2'-fluoro-4-biphenylyl)-2-propanol as colorless oily substance.

The compound thus obtained was treated with triphenylphosphine, phthalimide and diethyl azodicarboxylate in the same manner as in Example 114. Then, the phthalimide group was removed by means of hydrazine to obtain the above-identified compound as colorless oily substance.

The reaction was conducted in the same manner as in Example 118 except that o-bromofluorobenzene used in the above reaction was changed to o-bromoanisole, to obtain (1RS, 2RS)-3-(4-chlorophenyl)-2-(2'-methoxy-4-biphenylyl)-1-methylpropylamine.

EXAMPLE 119

Preparation of (1RS, 2RS)-3-(3,4-dichlorophenyl)-1-methyl-2-{3-(5-oxazolyl)phenyl}propylamine 0.15 g of 60% oily sodium hydride was dissolved in a liquid mixture of 1.5 ml of dimethylformamide and 1.5 ml of benzene, and a dimethylformamide 2 ml/benzene 2 ml solution of 0.72 g of 4-dimethoxymethylphenylacetone was dropwise added thereto with stirring under cooling with ice. The mixture was stirred at the same temperature for 15 minutes. To this solution, a dimethylformamide 2 ml/benzene 2 ml solution of 0.65 ml of 3,4-dichlorobenzyl chloride was dropwise added with stirring under cooling with ice. The mixture was stirred at the same temperature for 40 minutes. Then, a 3% citric acid aqueous solution and ethyl ether were added for liquid separation. The organic layer was collected by separation, then washed with a saturated sodium chloride aqueous solution and dried over anhydrous magnesium sulfate. Then, the solvent was distilled off under reduced pressure. The residue was subjected to medium pressure liquid chromatography (Lobar column™, size B, Lichroprep™ Si60F, manufactured by Merck Co.; hexane/ethyl acetate=10/1→6/1) to obtain 0.64 g (yield: 46%) of 4-(3,4-dichlorophenyl)-3-(4-dimethoxymethylphenyl)-2-butanone as colorless oily substance.

The compound thus obtained was reduced by means of L-selectride™ in the same manner as in Example 114 and then treated with a liquid mixture of 0.5 ml of 1N hydrochloric acid and 2 ml of tetrahydrofuran, to obtain (2RS, 3SR)-4-(3,4-dichlorophenyl)-3-(4-formylphenyl)-2propanol as colorless oily substance.

0.28 g of the formyl compound thus obtained was dissolved in 5 ml of methanol, and 0.17 g of p-toluenesulfonylmethyl isocyanide and 0.12 g of potassium carbonate were added. The mixture was refluxed under heating for 2 hours. The reaction solution was concentrated under reduced pressure, and the residue was dissolved in ethyl acetate and water. Then, the organic layer was collected by separation and dried over anhydrous sodium sulfate. The drying agent was separated by filtration, and then the solvent was distilled off under reduced pressure. The residue was subjected to silica gel column chromatography (hexane/ethyl acetate=1/1) to obtain 0.20 g (yield: 62%) of (2RS, 3SR)-4-(3,4-dichlorophenyl)-3-{4-(5-oxazolyl)phenyl}-2-propanol as colorless oily substance.

The compound thus obtained was treated with triphenylphosphine, phthalimide and diethyl azodicarboxylate in the same manner as in Example 114, and then the phthalimide group was removed by means of hydrazine, to obtain the above-identified compound as colorless oily substance.

EXAMPLE 120

Preparation of (1RS, 2RS)-N-{2-(4-biphenylyl)-3-(3,4-dichlorophenyl)-1-methylpropyl}methylamide 738 mg of 3-(4-biphenylyl)-4-(3,4-dichlorophenyl)-2-butanone was dissolved in a liquid mixture of 20 ml of methanol and 4 ml of tetrahydrofuran, and 4 ml of a 40% methylamine methanol solution was added thereto. The mixture was left to stand at room temperature overnight. The reaction solution was evaporated to dryness under reduced pressure, and the residue was dissolved in 15 ml of methanol. Then, 57 mg of sodium borohydride was added thereto, and the mixture was stirred at room temperature for one hour. The reaction solution was again evaporated to dryness under reduced pressure. Then, the residue was dissolved in a liquid mixture of ethyl ether and water. The organic layer was collected by separation, then washed with a saturated sodium chloride aqueous solution and dried over anhydrous magnesium sulfate. The drying agent was separated by filtration, and then the solvent was distilled off under reduced pressure. The residue was subjected to silica gel column chromatography (Wakogel™ C-300, 80 g; methylene chloride/methanol=50/1→25/1) and silica gel thin layer chromatography (Kieselgel™ 60F$_{254}$, Art 5744, manufactured by Merck Co.; methylene chloride/methanol=20/1) to obtain 97 mg (yield: 13%) of the above-identified compound as colorless oily substance.

The reaction was conducted in the same manner as in Example 120 except that 3-(4-biphenylyl)-4-(3,4-dichlorophenyl)-2-butanone used in the above reaction was changed to 3-(4-biphenylyl)-4-(4-chlorophenyl)-2-butanone, to obtain (1RS, 2RS)-N-{2-(4-biphenylyl)-3-(4-chlorophenyl)-1-methylpropyl}methylamine.

EXAMPLE 121

Preparation of (1S, 2S)-N-{2-(4-biphenylyl)-3-(3,4-dichlorophenyl)-1-methylpropyl}methylamine hydrochloride 0.82 g of (1S, 2S)-2-(4-biphenylyl)-3-(3,4-dichlorophenyl)-1-methylpropylamine obtained in Example 114 was dissolved in 2 ml of methylene chloride, and 1.5 ml of trifluoroacetic anhydride was added thereto with stirring under cooling with ice. The mixture was stirred at room temperature for 3 hours. The reaction solution was evaporated to dryness under reduced pressure, and the residue was dissolved in 5 ml of dimethylformamide, and then 1.5 ml of methyl iodide and 0.15 g of 60% oily sodium hydride were added thereto with stirring under cooling with ice. The mixture was stirred at room temperature for 2 hours. The reaction solution was extracted by an addition of water and ethyl ether. The organic layer was washed with a saturated sodium chloride aqueous solution and then dried over anhydrous magnesium sulfate. The drying agent was separated by filtration, and then the solvent was distilled off under reduced pressure. The residue was dissolved in 15 ml of tetrahydrofuran and 3 ml of methanol, and then a 4N sodium hydroxide aqueous solution was added thereto. The mixture was stirred at room temperature for 12 hours. The reaction solution was extracted by an addition of water and ethyl ether. The organic layer was washed with a saturated sodium chloride aqueous solution and then dried over anhydrous magnesium sulfate. The drying agent was separated by filtration, and then the solvent was distilled off under reduced pressure. The residue was treated with a liquid mixture of hydrogen chloride-methanol and ethyl ether, to obtain 0.65 g (yield: 70%) of the above-identified compound as white crystalline powder having a melting point of from 248° to 249° C. $[\alpha]_D^{20}$=+155° (c=1.0, methanol).

The reaction was conducted in the same manner as in Example 121 except that (1S, 2S)-2-(4-biphenylyl)-3-(3,4-dichlorophenyl)-1-methylpropylamine or methyl iodide used in the above reaction was changed to (1S, 2S)-3-(3,4-dichlorophenyl)-2-(2-fluoro-4-biphenylyl)-1-methylpropylamine or benzyl chloride, to obtain (1S, 2S)-N-{3-(3,4-dichlorophenyl)-2-(2-fluoro-4-biphenylyl)-1-methylpropyl}methylamine and (1S, 2S)-N-benzyl-2-(4-biphenylyl)-3-(3,4-dichlorophenyl)-1-methylpropylamine.

EXAMPLE 122

Preparation of (1S, 2R)-3-(3,4-dichlorophenyl)-1-methyl-2-(2-naphthoyloxy)-propylamine and its hydrochloride Added to 40 ml of ethyl ether was 4 g of magnesium (turnings). Then, a few drops of dibromoethane was added thereto. Then, 100 ml of an ethyl ether solution of 29.3 g of 3,4-dichlorobenzyl chloride was dropwise added thereto over a period of 2 hours with stirring under cooling with ice. After the addition, stirring was continued for one hour under cooling with ice. Then, 300 ml of a tetrahydrofuran solution of 11.6 g of N-(tert-butoxycarbonyl)-L-alanine-N-methyl-N-methoxycarboxyamide (J. Med. Chem., 33, 11 (1990)) was added thereto over a period of one hour. Then, the mixture was stirred at the same temperature for further one hour. Then, 100 ml of a saturated ammonium chloride aqueous solution was added to the reaction solution with stirring under cooling with ice. The organic layer was collected by separation, then washed with a saturated sodium chloride aqueous solution and dried over anhydrous magnesium sulfate. The drying agent was separated by filtration, and then the solvent was distilled off under reduced pressure. The residue was subjected to silica gel column chromatography (hexane/ethyl acetate=10/1→4/1) to obtain 15.7 g (yield: 95%) of (S)-N-(tert-butoxycarbonyl)-3-(3,4-dichlorophenyl)-1-methyl-2-oxopropylamine.

15.7 g of the ketone compound thus obtained was dissolved in 300 ml of methanol, and 1.8 g of sodium borohydride was added thereto with stirring under cooling with ice. The mixture was stirred at the same temperature for one hour. The reaction solution was diluted with water. Then, methanol was distilled off under reduced pressure. The residual solution was extracted by an addition of ethyl acetate. The extract solution was washed with a saturated sodium chloride aqueous solution and then dried over anhydrous magnesium sulfate. The drying agent was removed by filtration, and then the solvent was distilled off under reduced pressure. The residue was dissolved in a liquid mixture of 300 ml of methylene chloride and 30 ml of dimethylformamide, and 8.9 g of 2-naphthoic acid, 6.3 g of 4-dimethylaminopyridine and 10.0 g of 1-ethyl-3-(3-dimethylaminopropyl)carbodiimide hydrochloride were added thereto with stirring under cooling with ice. The mixture was stirred at room temperature overnight. The reaction solution was concentrated under reduced pressure. Then, the residue was dissolved in ethyl acetate, sequentially washed with 1N hydrochloric acid, a saturated sodium hydrogencarbonate aqueous solution and a saturated sodium chloride aqueous solution and then dried over anhydrous magnesium sulfate. The drying agent was separated by filtration, and then the solvent was distilled off under reduced pressure. The residue was subjected to silica gel column chromatography (hexane/ethyl acetate=10/1→5/1) to obtain 14.2 g (yield: 62%) of (1S, 2R)-N-(tert-butoxycarbonyl)-3-(3,4-dichlorophenyl)-1-methyl-2-(2-naphthoyloxy)propylamine.

5 g of the obtained N-(tert-butoxycarbonyl) derivative of the above-identified compound thus obtained was dissolved in 30 ml of dioxane, and 20 ml of a 4N hydrogen chloride-dioxane solution was added thereto. The mixture was left to stand at room temperature for 2 days. Precipitated crystals were collected by filtration, washed with ethyl ether and then dried to obtain 4.1 g (yield: 93%) of a hydrochloride of the above-identified compound as white crystalline powder having a melting point of from 194° to 196° C.

The hydrochloride thus obtained was added under stirring to a liquid mixture of methylene chloride and a 0.5N sodium hydroxide aqueous solution. Then, the organic layer was collected by separation, then washed with a saturated sodium chloride aqueous solution and dried over anhydrous magnesium sulfate. The drying agent was separated by filtration, and then the solvent was distilled off under reduced pressure to obtain a free base of the above-identified compound.

The following compounds were prepared in the same manner as in Example 122 except that N-(tert-butoxycarbonyl)-L-alanine-N-methyl-N-methoxycarboxyamide or 2-naphthoic acid used as the starting materials in the above reaction, was changed to N-(tert-butoxycarbonyl)-D,L-alanine-N-methyl-N-methoxycarboxyamide or 4-chloro-3-methylbenzoic acid or quinaldinic acid, respectively: (1RS, 2SR)-3-(3,4-dichlorophenyl)-1-methyl-2-(2-naphthoyloxy)propylamine, (1S, 2R)-2-(4-chloro-3-methylbenzoyloxy)-3-(3,4-dichlorophenyl)-1-methylpropylamine and (1S, 2R)-3-(3,4-dichlorophenyl)-1-methyl-2-(2-quinolinecarbonyloxy)propylamine.

EXAMPLE 123

Preparation of (1RS, 2RS, 3E)-2-(3,4-dichlorobenzyl)-1-methyl-4-(2-naphthyl)-3-butenylamine 10.5 g of tert-butyl 2-(3,4-dichlorobenzyl)acetoacetate (which was prepared by treating 3,4-dichlorobenzyl chloride and tert-butyl acetoacetate with potassium tert-butoxide in tert-butanol) was dissolved in 100 ml of tetrahydrofuran, and 45 ml of a 1M tetrahydrofuran solution of lithium tri-sec-butylborohydride was added thereto with stirring under cooling to −70° C. The mixture was stirred at the same temperature for 1 hour. Then, 20 ml of water and 15 ml of a 3N sodium hydroxide aqueous solution were added to the reaction solution, and 15 ml of a 30% hydrogen peroxide aqueous solution was dropwise added thereto with stirring under cooling to −20° C. The mixture was stirred at room temperature for 1 hour. Then, hexane was added to the reaction solution, and the organic layer was collected by separation, then washed with a saturated sodium chloride aqueous solution and dried over anhydrous magnesium sulfate. The drying agent was separated by filtration, and then the solvent was distilled off under reduced pressure. The residue was subjected to silica gel column chromatography (hexane/ethyl acetate=10/1→5/1) to obtain 3.79 g (yield: 33%) of tert-butyl (2RS, 3RS)-2-(3,4-dichlorobenzyl)-3-hydroxybutanoate.

3.0 g of the alcohol compound thus obtained was dissolved in a liquid mixture of 30 ml of ethyl ether and 30 ml of tetrahydrofuran, and 1.2 g of lithium borohydride was added thereto with stirring under cooling with ice. The mixture was stirred at room temperature for 3 hours. The reaction solution was diluted with ethyl ether, then washed with a saturated sodium chloride aqueous solution and dried over anhydrous magnesium sulfate. The drying agent was separated by filtration, and then the solvent was distilled off under reduced pressure. The residue was subjected to silica gel column chromatography (hexane/ethyl acetate=10/1) to obtain 2.1 g (yield: 90%) of (2RS, 3RS)-2-(3,4-dichlorobenzyl)-1,3-butanediol.

1.66 g of the diol compound thus obtained was dissolved in 10 ml of methylene chloride, and 1.10 g of tert-butyldimethylchlorosilane, 1.0 ml of triethylamine and 0.04 g of 4-dimethylaminopyridine were added thereto with stirring under cooling with ice. The mixture was stirred at room temperature overnight. The reaction solution was evaporated to dryness under reduced pressure. Then, the residue was extracted by an addition of water and a 5% citric acid aqueous solution. The organic layer was washed with a saturated sodium chloride aqueous solution and dried over anhydrous magnesium sulfate. The drying agent was separated by filtration, and then the solvent was distilled off under reduced pressure. The residue was subjected to silica gel column chromatography (hexane→hexane/ethyl acetate=10/1) to obtain 1.50 g (yield: 62%) of (2RS, 3RS)-3-(3,4-dichlorobenzyl)-4-(tert-butyldimethylsilyloxy)-2-butanol.

1.49 g of the silyloxy compound thus obtained was dissolved in 10 ml of tetrahydrofuran, and 1.21 g of phthalimide, 2.15 g of triphenylphosphine and 1.43 g of diethyl azodicarboxylate were added thereto. The mixture was stirred at room temperature overnight. The reaction solution was evaporated to dryness under reduced pressure. Then, the residue was subjected to silica gel column chromatography (hexane/ethyl acetate=30/1→20/1) to obtain 1.07 g (yield: 53%) of N-{(1RS, 2SR)-2-(3,4-dichlorobenzyl)-3-(tert-butyldimethylsilyloxy)-1-methylpropyl}phthalimide.

1.07 g of the phthalimide compound thus obtained was dissolved in 15 ml of tetrahydrofuran, and 2.6 ml of a 1M tetrahydrofuran solution of tetrabutylammonium fluoride was added thereto. The mixture was stirred at room temperature overnight. The reaction solution was evaporated to dryness under reduced pressure. Then, the residue was dissolved in a liquid mixture of water and ethyl ether. The organic layer was collected by separation and then dried over anhydrous magnesium sulfate. The drying agent was separated by filtration, and then the solvent was distilled off under reduced pressure. The residue was subjected to medium pressure liquid chromatography (hexane/ethyl acetate=4/1→2/1) to obtain 0.39 g (yield: 47%) of N-{(1RS, 2SR)-2-(3,4-dichlorobenzyl)-3-hydroxy-1-methylpropyl}phthalimide.

0.26 g Of the alcohol compound thus obtained was dissolved in 4 ml of methylene chloride, and 0.44 g of pyridinium chlorochromate was added thereto with stirring under cooling with ice, and the mixture was stirred at room temperature for 2 hours. The reaction solution was diluted with ethyl ether. Then, insoluble matters were separated by filtration. The filtrate was evaporated to dryness under reduced pressure. The residue was subjected to medium pressure liquid chromatography (hexane/ethyl acetate=5/1→3/1) to obtain 0.19 g (yield: 73%) of N-{(1RS, 2SR)-3-(3,4-dichlorophenyl)-2-formyl-1-methylpropyl}phthalimide.

340 mg of (2-naphthylmethyl)triphenylphosphonium chloride and 24 mg of 60% oily sodium hydride were added to 4 ml of tetrahydrofuran, and the mixture was stirred at room temperature for 30 minutes. Then, 1 ml of a tetrahydrofuran solution of 144 mg of the formyl compound obtained above, was added thereto, and the mixture was further stirred at room temperature for 2 hours. Ethyl ether and water were added to the reaction solution. The organic layer was collected by separation then washed with a saturated sodium chloride aqueous solution and dried over anhydrous magnesium sulfate. The drying agent was separated by filtration, and then the solvent was distilled off under reduced pressure. The residue was subjected to silica gel column chromatography (hexane→hexane/ethyl acetate=10/1) to obtain 150 mg (yield: 75%) of N-{(1RS, 2RS, 3E)-2-(3,4-dichlorobenzyl)-1-methyl-4-(2-naphthyl)-3-butenyl}phthalimide.

150 mg of the butenyl compound thus obtained was dissolved in 2 ml of ethanol, and 190 mg of hydrazine monohydrate was added thereto. The mixture was refluxed under heating for 2 hours. The reaction solution was evaporated to dryness under reduced pressure. Then, the residue was dissolved in methylene chloride, and insoluble matters were removed by filtration. Then, the solvent was again distilled off under reduced pressure. The residue was subjected to silica gel column chromatography (chloroform→chloroform/methanol=10/1) to obtain 76 mg (yield: 68%) of the above-identified compound as colorless oily substance.

The following compounds were prepared in the same manner as in Example 123 except that tert-butyl 2-(3,4-dichlorobenzyl)acetoacetate and/or (2-naphthylmethyl)triphenylphosphonium chloride used as the starting materials in the above reaction were changed to the respective tert-butyl 2-(4-chlorobenzyl)acetoacetate and/or corresponding phosphonium derivatives: (1RS, 2RS, 3E)-4-(2-benzo[b]furanyl)-2-(3,4-dichlorobenzyl)-1-methyl-3-butenylamine, (1RS, 2RS, 3E)-2-(3,4-dichlorobenzyl)-1-methyl-4-{3-(3-thienyl)phenyl}-3-butenylamine, (1RS, 2RS, 3E)-2-(3,4-dichlorobenzyl)-1-methyl-4-(1-naphthyl)-3-butenylamine and (1RS, 2RS, 3E)-2-(4-chlorobenzyl)-4-(4-chlorophenyl)-1-methyl-3-butenylamine.

EXAMPLE 124

Preparation of (1S, 2S, 3E)-2-(3,4-dichlorobenzyl)-1-methyl-4-(2-naphthyl)-3-butenylamine 9.45 g of methyl (R)-(−)-3-hydroxybutyrate was dissolved in 200 ml of tetrahydrofuran, and 112 ml of a 1.5M cyclohexane solution of lithium diisopropylamide was added thereto with stirring under cooling to −70° C. Then, the temperature was raised to −25° C. Then, 35 ml of a hexamethylphosphoric triamide solution of 21.1 g of 3,4-dichlorobenzyl bromide was dropwise added to this solution under stirring while maintaining the temperature at −25° C. After the dropwise addition, the temperature was raised to room temperature. Then, a saturated ammonium chloride aqueous solution was added to the reaction solution with stirring under cooling with ice. Then, the temperature was raised to room temperature, and ethyl ether and water were added thereto for liquid separation. The organic layer was collected by separation and post-treated by a conventional method. The product was purified by silica gel column chromatography (hexane/ethyl acetate=4/1) to obtain 10.6 g (yield: 48%) of methyl (2R, 3R)-2-(3,4-dichlorobenzyl)-3-hydroxybutyrate.

10.6 g of the benzyl compound thus obtained was dissolved in 100 ml of dimethylformamide, and 3.9 g of imidazole and 6.9 g of tert-butyldimethylchlorosilane were added thereto with stirring under cooling with ice. The mixture was stirred at room temperature for 6 hours. The reaction solution was made basic by an addition of a saturated sodium hydrogencarbonate aqueous solution, and then ethyl ether and water were added thereto for liquid separation. The organic layer was collected by separation and post-treated by a conventional method. The product was purified by silica gel column chromatography (hexane/ethyl acetate=50/1) to obtain 12.6 g (yield: 84%) of methyl (2R, 3R)-3-(tert-butyldimethylsilyloxy)-2-(3,4-dichlorobenzyl)butyrate.

12.6 g of the silyloxy compound thus obtained was dissolved in 100 ml of toluene, and 79 ml of a 1.02M toluene solution of diisobutylaluminum hydride was added thereto under cooling to −78° C. The mixture was stirred at the same temperature for 45 minutes. Then, a saturated ammonium chloride aqueous solution was added to the reaction solution with stirring under cooling to −70° C. The temperature was raised to room temperature, and 1N hydrochloric acid and ethyl acetate were added for extraction. The organic layer was collected by separation and sequentially washed with a saturated sodium hydrogencarbonate aqueous solution and a saturated sodium chloride aqueous solution and dried over anhydrous magnesium sulfate. The drying agent was separated by filtration, and then the solvent was distilled off under reduced pressure. The residue was dissolved in 70 ml of methylene chloride, and then 13.9 g of pyridinium chlorochromate was added thereto. The mixture was stirred at room temperature for 2 hours. The reaction solution was diluted by an addition of ethyl ether, and insoluble matters were separated by filtration. Then, the solvent was distilled off under reduced pressure. The residue was purified by silica gel column chromatography (hexane/ethyl acetate=50/1) to obtain 8.15 g (yield: 70%) of (2R, 3R)-3-(tert-butyldimethylsilyloxy)-2-(3,4-diclorobenzyl)butylaldehyde.

14.7 g of 2-naphthylmethyltriphenylphosphonium bromide was dissolved in 80 ml of tetrahydrofuran, and 1.27 g of 60% oily sodium hydride was added thereto. The mixture was stirred at room temperature for 30 minutes. Then, 20 ml of a tetrahydrofuran solution of 8.15 g of the aldehyde compound obtained above was added to this solution, and the mixture was stirred for 1 hour at room temperature. Then, water and ethyl acetate was added thereto for extraction. The organic layer was collected by separation, then washed with a saturated sodium chloride aqueous solution and dried over anhydrous magnesium sulfate. The drying agent was separated by filtration, and then the solvent was distilled off under reduced pressure. The residue was dissolved in 60 ml of tetrahydrofuran, and then 45 ml of a 1M tetrahydrofuran solution of tributylammonium fluoride was added thereto. The mixture was stirred at room temperature for 3 hours. The reaction solution was extracted by an addition of ethyl acetate and water. The organic layer was collected by separation and post-treated by a conventional method. The product was purified by silica gel column chromatography (hexane/ethyl acetate=10/1→7/1) to obtain 6.43 g (yield: 77%) of (2R, 3S)-3-(3,4-dichlorobenzyl)-5-(2-naphthyl)-4-penten-2-ol.

6.43 g of the alcohol compound thus obtained and 6.81 g of triphenylphosphine were dissolved in 80 ml of tetrahydrofuran, and 4.14 ml of diethyl azodicarboxylate and then 20 ml of a tetrahydrofuran solution of 7.15 g of diphenylphosphoryl azide were sequentially dropwise added thereto with stirring under cooling with ice. Then, the mixture was stirred at room temperature overnight. The reaction solution was evaporated to dryness under reduced pressure. Then, the residue was purified by silica gel column chromatography (hexane/ethyl acetate=50/1) to obtain 6.50 g (yield: 95%) of (3S, 4S)-4-azido-3-(3,4-dichlorobenzyl)-1-(2-naphthyl)-1-pentene.

6.50 g of the azide compound thus obtained was dissolved in a liquid mixture of 100 ml of tetrahydrofuran and 10 ml of water, and 4.30 g of triphenylphosphine was added thereto. The mixture was refluxed under heating for 3 hours.

The reaction solution was evaporated to dryness under reduced pressure. Then, ethanol was added to the residue, and the mixture was again evaporated to dryness under reduced pressure. The obtained residue was dissolved in 50 ml of methanol, and then 6.17 g of (–)-dibenzoyl-L-tartaric acid monohydrate was added thereto. The mixture was left to stand at room temperature overnight. Precipitated crystals were collected by filtration, washed with ethyl ether and then dried to obtain 10.35 g (yield: 87%) of a (–)-dibenzoyl-L-tartarate of the above-identified compound.

The (–)-dibenzoyl-L-tartarate thus obtained was added to a liquid mixture of ethyl ether and water, and a 1N sodium hydroxide aqueous solution was dropwise added thereto with stirring under cooling with ice to make it basic. Then, the ethyl ether layer was treated by a conventional method to obtain the above-identified compound as colorless oily substance.

Likewise, the free base of the above-identified compound thus obtained was treated with a hydrogen chloride-methanol solution and recrystallized from a liquid mixture of methylene chloride-ethyl ether to obtain a hydrochloride of the above-identified compound as white crystalline powder.

EXAMPLE 125

Preparation and optical resolution of (1RS, 2RS)-3-(3,4-dichlorophenyl)-2-(2-fluoro-4-biphenylyl)-1-methylpropylamine 150 g of 4-bromo-2-fluorobiphenyl, 89.6 g of isopropenyl acetate, 258 ml of tributyltin butoxide and 4.7 g of a palladium chloride-tri(o-phenyl)phosphine complex were added to 300 ml of toluene and the mixture was stirred under heating at 80° C. for 2 hours under a nitrogen atmosphere. The reaction solution was left to cool to room temperature. Then, 1 l of ethyl acetate and 500 ml of a saturated potassium fluoride aqueous solution were added thereto, and the mixture was vigorously stirred. Insoluble matters were separated by filtration, and then the organic layer was collected by separation. The obtained organic layer was post-treated by a conventional method. The product was treated with hexane to obtain 106 g (yield: 78%) of 1-(2-fluoro-4-biphenylyl)-2-propanone.

45.1 g of the ketone compound thus obtained, 50.3 g of 3,4-dichlorobenzyl chloride and 15.8 g of sodium hydroxide were mixed, heated with stirring at 100° C. for 6 hours. The reaction solution was left to cool to room temperature and then extracted by an addition of ethyl acetate and water. The organic layer was post-treated by a conventional method. Then, the product was purified by silica gel column chromatography (hexane/ethyl acetate=50/1) to obtain 65.0 g (yield: 85%) of 4-(3,4-dichlorophenyl)-3-(2-fluoro-4-biphenylyl)-2-butanone.

63.0 g of the 3,4-dichlorobenzyl compound thus obtained was dissolved in 630 ml of tetrahydrofuran, and 200 ml of a 1M tetrahydrofuran solution of lithium tri-sec-butylborohydride (L-selectride™) was added thereto with stirring under cooling to –78° C. The mixture was stirred at the same temperature for 1 hour. A 3N sodium hydroxide aqueous solution was added to the reaction solution, and the mixture was stirred for 30 minutes under cooling with ice. Then, 90 ml of a 30% hydrogen peroxide aqueous solution was added thereto, and the mixture further stirred for 3 hours. Then, 1 l of ethyl acetate was added to the reaction solution for liquid separation. The organic layer was collected by separation and then post-treated by a conventional method to obtain 60.1 g (yield: 95%) of (2RS, 3SR)-4-(3,4-dichlorophenyl)-3-(2-fluoro-4-biphenylyl)-2-butanol.

60.1 g of the alcohol compound thus obtained was dissolved in 420 ml of ethyl acetate, and 13.2 ml of methanesulfonyl chloride and 25.6 ml of triethylamine were added thereto with stirring under cooling with ice. The mixture was stirred at room temperature for 30 minutes. The reaction solution was washed with a saturated sodium hydrogencarbonate aqueous solution. The solvent was distilled off under reduced pressure. Then, the residue was dissolved in 210 ml of dimethylformamide, and 50 g of sodium azide was added thereto. The mixture was heated and stirred at 100° C. for 1 hour. Then, ethyl ether and water were added to the reaction solution for liquid separation. The organic layer was collected by separation and then washed with a saturated sodium chloride aqueous solution. Then, the solvent was distilled off under reduced pressure. The residue was dissolved in a liquid mixture of 400 ml of tetrahydrofuran and 40 ml of water, and 60.3 g of triphenylphosphine was added thereto. The mixture was heated with stirring at 80° C. for 8 hours. The reaction solution was evaporated to dryness under reduced pressure. Then, ethanol was added to the residue, and the mixture was again evaporated to dryness under reduced pressure. The obtained residue was dissolved in a liquid mixture of 200 ml of methanol and 200 ml of isopropyl ether, and 23.1 g of L-(+)-tartaric acid was added thereto. The mixture was left to stand at room temperature overnight. Precipitated crystals were collected by filtration, washed with isopropyl ether and then dried to obtain 51.8 g (yield: 62.5%) of a L-(+)-tartarate of the above-identified compound.

50.8 g of the L-(+)-tartarate of the above-identified compound thus obtained was dissolved in 920 ml of hot methanol, and seed crystals were added thereto. The mixture was left to stand at room temperature for 3 days. Precipitated crystals were collected by filtration and again dissolved in 680 ml of hot methanol, and the seed crystals were added thereto, and the mixture was left to stand at room temperature for 2 days. Precipitated crystals were collected by filtration, washed with a small amount of methanol and then dried to obtain 13.0 g (yield: 26%) of a L-(+)-tartarate of the (1S, 2S)-isomer of the above-identified compound as white crystals, $[\alpha]_D^{20}$=+136° (c=0.75, methanol).

Likewise, the filtrate after the filtration of the L-(+)-tartarate of the (1S, 2S)-isomer and the washing solutions were put together, evaporated to dryness under reduced pressure and treated with a base by a conventional method to obtain a free base of the above-identified compound as a mixture of enantiomers. This base was subjected to the same optical resolution as above by means of D-(–)-tartaric acid, to obtain a D-(–)-tartarate of the (1R, 2R)-isomer of the above-identified compound, $[\alpha]_D^{20}$=–134° (c=0.75, methanol), which is an enantiomer of the (1S, 2S)-isomer as obtained above.

The racemic and optically active tartarates of the above-identified compound were treated with a base by a conventional method to obtain free amines of the (1RS, 2RS)-isomer, the (1S, 2S)-isomer $[\alpha]_D^{20}$ = +192° (c = 0.5, methanol), and the (1R, 2R)-isomer
$[\alpha]_D^{20}$ = –191° (c = 0.5, methanol) of the above-identified compound.

The reaction was conducted in the same manner as in Example 125 except that 4-bromo-2-fluorobiphenyl used as the starting material in the above reaction was changed to 4-bromobiphenyl, to obtain (1RS, 2RS)-2-(4-biphenylyl)-3-(3,4-dichlorophenyl)-1-methylpropylamine.

REFERENCE EXAMPLE 1

Preparation of dibenzhydryl carboxymethylsuccinate

The reaction product obtained by conducting the Michael-addition reaction in the same manner as in Example 116 using 5.7 ml of a 1.5M cyclohexane solution of lithium diisopropylamide, 2.6 g of trityl acetate and 3.2 g of dibenzhydryl maleate, was dissolved in a liquid mixture of 20 ml of acetic acid and 5 ml of water, and the solution was left to stand at room temperature overnight and then evaporated to dryness under reduced pressure. The residue was subjected to silica gel column chromatography (chloroform/methanol=100/1→10/1) to obtain 1.05 g (yield: 29%) of the above-identified compound as white crystalline powder having a melting point of from 105° to 106° C.

REFERENCE EXAMPLE 2

Preparation of N-{(1RS, 2RS)-3-(4-biphenylyl)-2-(4-chlorophenyl)-1-methylpropyl}-2-naphthylmethylamine 32 mg of (1RS, 2RS)-3-(4-biphenylyl)-2-(4-chlorophenyl)-1-methylpropylamine was dissolved in 1 ml of methanol, and 22 mg of 2-naphthoaldehyde was added thereto. The mixture was stirred at room temperature for 1 hour. The reaction solution was evaporated to dryness under reduced pressure, and the residue was again dissolved in 1 ml of methanol, and 6.7 mg of sodium borohydride was added thereto. The mixture was stirred at room temperature for 30 minutes. The reaction solution was extracted by an addition of water and ethyl ether. The organic layer was washed with a saturated sodium chloride aqueous solution and then dried over anhydrous sodium sulfate. The drying agent was separated by filtration, and then the solvent was distilled off under reduced pressure. The residue was subjected to silica gel thin layer chromatography (hexane/ethyl acetate=5/1) to obtain 46 mg of the above-identified compound as colorless oily substance.

The following compounds were prepared in the same manner as in Reference Example 2 except that (1RS, 2RS)-3-(4-biphenylyl)-2-(4-chlorophenyl)-1-methylpropylamine used in the above reaction was changed to the corresponding amine compounds: N-{(1RS, 2RS)-3-(3-biphenylyl)-2-(4-chlorophenyl)-1-methylpropyl}-2-naphthylmethylamine, N-{(1RS, 2RS)-3-(4'-chloro-4-biphenylyl)-2-(4-chlorophenyl)-1-methylpropyl}-2-naphthylmethylamine, N-{(1RS, 2RS)-2-(4-chlorophenyl)-3-(2-fluoro-4-biphenylyl)-1-methylpropyl}-2-naphthylmethylamine, N-{(1RS, 2RS)-2-(4-chlorophenyl)-3-(6-fluoro-3-biphenylyl)-1-methylpropyl}-2-naphthylmethylamine, N-[(1RS, 2RS)-2-(4-chlorophenyl)-1-methyl-3-{3-(2-naphthyl)phenyl}propyl]-2-naphthylmethylamine, N-{(1RS, 2RS)-3-(4-biphenylyl)-2-(3,4-dichlorophenyl)-1-methylpropyl}-2-naphthylmethylamine and N-{(1RS, 2RS)-3-(4-biphenylyl)-1-methyl-2-(2-naphthyl)propyl}-2-naphthylmethylamine.

REFERENCE EXAMPLE 3

Preparation of N-{(1RS, 2SR)-2-(3,4-dichlorobenzyl)-1-methyl-3-(2-naphthoxy)-propyl}phthalimide 1.14 g of tert-butyl (2RS, 3RS)-2-(3,4-dichlorobenzyl)-3-hydroxybutanoate obtained in Example 123 was dissolved in 10 ml of dimethylformamide, and 0.65 g of tert-butyldimethylchlorosilane and 0.37 g of imidazole were added thereto with stirring under cooling with ice. The mixture was stirred at room temperature for 6 hours. The reaction solution was diluted with ethyl ether, then washed with a saturated sodium hydrogencarbonate aqueous solution and a saturated sodium chloride aqueous solution, and dried over anhydrous magnesium sulfate. The drying agent was separated by filtration, and then the solvent was distilled off under reduced pressure. The residue was dissolved in 10 ml of toluene, and then a 1M toluene solution of diisobutylaluminum hydride was added thereto with stirring under cooling to −78° C. The mixture was stirred at the same temperature for 1 hour. A saturated ammonium chloride aqueous solution was added to the reaction solution with stirring under cooling to −78° C., and the temperature was raised to room temperature. Then, 1N hydrochloric acid and ethyl acetate were added thereto for liquid separation. The organic layer was washed with a saturated sodium chloride aqueous solution and then dried over anhydrous magnesium sulfate. The drying agent was separated by filtration, and then the solvent was distilled off under reduced pressure. The residue was subjected to silica gel column chromatography to obtain 0.99 g (yield: 76%) of (2RS, 3RS)-2-(3,4-dichlorobenzyl)-3-(tert-butyldimethylsilyloxy)butanol.

200 mg of the alcohol compound thus obtained was dissolved in 5 ml of ethyl acetate, and 55 μl of methanesulfonyl chloride and 120 μl of triethylamine were added thereto with stirring under cooling with ice, and the mixture was stirred at the same temperature for 30 minutes. Formed precipitate was separated by filtration, and the filtrate was evaporated to dryness under reduced pressure. Then, the residue was dissolved in 5 ml of dimethylformamide. Separately, 87 mg of 2-naphthol was dissolved in 5 ml of dimethylformamide, and 24 mg of 60% oily sodium hydride was added. The mixture was stirred at room temperature for 30 minutes. To this solution, the dimethylformamide solution of the mesylated compound obtained above, was added under stirring. Further, 91 mg of potassium iodide was added thereto. Then, the mixture was stirred at room temperature for 3 days. The reaction solution was poured into water and extracted by an addition of ethyl ether. Then, the ether extract solution was washed with a saturated sodium chloride aqueous solution and dried over anhydrous magnesium sulfate. The drying agent was separated by filtration, and then the solvent was distilled off under reduced pressure. The residue was subjected to silica gel column chromatography to obtain 77 mg (yield: 29%) of (2RS, 3RS)-2-(3,4-dichlorobenzyl)-3-(tert-butyldimethylsilyloxy)-1-(2-naphthoxy)butane.

77 mg of the naphthoxy compound thus obtained was dissolved in 3 ml of tetrahydrofuran, and 0.5 ml of a 1M tetrahydrofuran solution of tetrabutylammonium fluoride was added thereto. The mixture was stirred at room temperature for 4 hours. Then, ethyl acetate and water were added to the reaction solution. The organic layer was collected by separation, then washed with a saturated sodium chloride aqueous solution and dried over anhydrous magnesium sulfate. The drying agent was separated by filtration, and then the solvent was distilled off under reduced pressure. The residue was subjected to silica gel column chromatography to obtain 60 mg (yield: 100%) of (2RS, 3RS)-3-(3,4-dichlorobenzyl)-4-(2-naphthoxy)-2-butanol.

60 mg of the alcohol compound thus obtained was dissolved in 3 ml of tetrahydrofuran, and 31 mg of phthalimide, 55 mg of triphenylphosphine and 30 μl of diethyl azodicarboxylate were added thereto, and the mixture was stirred at room temperature overnight. The reaction solution was evaporated to dryness under reduced pressure. Then, the residue was treated with methanol to obtain 45 mg (yield: 56%) of the above-identified compound as white crystalline powder.

Reactions were conducted in the same manner as in Reference Example 3 except that tert-butyl (2RS, 3RS)-1-(3,4-dicholobenzyl)-3-hydroxybutanoate and/or 2-naphthol used as starting materials in the above reaction were changed to tert-butyl (2RS, 3RS)-1-(4-chlorobenzyl)-3-hydroxybutanoate and/or 4-chlorophenol or 2-naphthalenethiol, respectively, to obtain N-{(1RS, 2SR)-2-(4-chlorobenzyl)-3-(4-chlorophenoxy)-1-methylpropyl}phthalimide and N-{(1RS, 2SR)-2-(3,4-dichlorobenzyl)-1-methyl-3-(2-naphthylthio)propyl}phthalimide.

REFERENCE EXAMPLE 4

Preparation of
N-{2-(4-chlorobenzyl)-4-(4-chlorophenyl)-1-methylbutyl}phthalimide 1.94 g of tert-butyl 2-{2-(4-chlorophenyl)ethyl}-3-oxobutanoate was dissolved in 10 ml of tert-butanol, and 0.17 g of p-chlorobenzyl chloride and 0.90 g of potassium tert-butoxide were added thereto. The mixture was heated and refluxed for 1 hour. Then, ethyl ether and water were added to the reaction solution for liquid separation. The organic layer was washed with a saturated sodium chloride aqueous solution and then dried over anhydrous magnesium sulfate. The drying agent was separated by filtration and then the solvent was distilled off under reduced pressure. The residue was subjected to medium pressure liquid chromatography (hexane/ethyl acetate=9/1) to obtain 1.43 g (yield: 52%) of tert-butyl 2-(4-chlorobenzyl)-2-{2-(4-chlorophenyl)ethyl}-3-oxobutanoate.

1.43 g of the 4-chlorobenzyl compound thus obtained was dissolved in 15 ml of methylene chloride, and 2.6 ml of trifluoroacetic acid was added thereto. The mixture was stirred at room temperature for 1 hour. The reaction solution was evaporated to dryness under reduced pressure. Then, the residue was dissolved in 5 ml of toluene and heated at 120° C. for 1 hour. Then, the solvent was distilled off under reduced pressure. The residue was dissolved in 10 ml of ethanol, and 63 mg of sodium borohydride was added thereto with stirring under cooling with ice. The mixture was stirred at room temperature for 3 hours. The reaction solution was concentrated under reduced pressure. Then, the residue was extracted by an addition of ethyl ether and water. The organic layer was washed with a saturated sodium chloride aqueous solution and then dried over anhydrous magnesium sulfate. The drying agent was separated by filtration, and then the solvent was distilled off under reduced pressure. The residue was dissolved in 2 ml of tetrahydrofuran, and then 96 mg of phthalimide, 173 mg of triphenylphosphine and 104 μl of diethyl azodicarboxylate were added thereto, and the mixture was stirred at room temperature for 2 hours. Then, ethyl acetate and water were added to the reaction solution for liquid separation. The organic layer was washed with a saturated sodium chloride aqueous solution and then dried over anhydrous magnesium sulfate. The drying agent was separated by filtration, and then the solvent was distilled off under reduced pressure. The residue was subjected to silica gel column chromatography (hexane/ethyl acetate=19/1→4/1) to obtain 78 mg (yield: 52%) of the above-identified compound (a mixture of two diastereomers) as white powder.

REFERENCE EXAMPLE 5

Preparation of
N-{3-(3,4-dichlorophenyl)-1-methyl-2-(2-naphthylmethoxy)propyl}phthalimide 2.45 g of magnesium (turnings) was added to 100 ml of ethyl ether, and a few drops of 1,2-dibromoethane were added thereto to activate magnesium. Then, 100 ml of an ethyl ether solution of 19.2 g of 3,4-dichlorobenzyl chloride was dropwise added thereto over a period of 3 hours with stirring under cooling with ice. Then, 50 ml of an ethyl ether solution of 6.11 g of 2-(tert-butyldimethylsilyloxy)propionaldehyde (which was produced by silylating ethyl 2-hydroxypropionate with tert-butyldimethylchlorosilane, followed by reducing with diisobutylaluminum hydride) was dropwise added to this solution over a period of 30 minutes with stirring under cooling with ice, and the mixture was stirred at the same temperature for 1 hour. Then, a saturated ammonium chloride aqueous solution was added thereto, and the mixture was further stirred at room temperature for 10 minutes. The organic layer was collected by separation, washed with a saturated sodium chloride aqueous solution and then dried over anhydrous magnesium sulfate. The drying agent was separated by filtration, and then the solvent was distilled off under reduced pressure. The residue was subjected to silica gel column chromatography to obtain 3.82 g (yield: 33%) of 3-(tert-butyldimethylsilyloxy)-1-(3,4-dichlorophenyl)-2-butanol.

2.32 g of the alcohol compound thus obtained was dissolved in a liquid mixture of 100 ml of tetrahydrofuran and 20 ml of dimethylformamide, and 0.34 g of 60% oily sodium hydride was added thereto with stirring under cooling with ice. The mixture was stirred at the same temperature for 30 minutes. Then, 1.47 g of 2-naphthylmethyl bromide was added thereto, and the mixture was stirred at room temperature for 20 hours. Then, ethyl ether and water were added to the reaction solution for liquid separation. The organic layer was washed with a saturated sodium chloride aqueous solution and then dried over anhydrous magnesium sulfate. The drying agent was separated by filtration, and then the solvent was distilled off under reduced pressure. The residue was subjected to silica gel column chromatography (hexane+hexane/ethyl acetate=50/1) for rough purification and then added to a liquid mixture of 100 ml of tetrahydrofuran and 8 ml of a 1M tetrahydrofuran solution of tetrabutylammonium fluoride. The mixture was stirred at room temperature for 3 hours. The reaction solution was concentrated under reduced pressure. Then, the residue was extracted by an addition of ethyl acetate and water. The organic layer was washed with a saturated sodium chloride aqueous solution and dried over anhydrous magnesium sulfate. The drying agent was separated by filtration, and then the solvent was distilled off under reduced pressure. The residue was subjected to silica gel column chromatography (hexane/ethyl acetate=20/1→5/1) to obtain 0.46 g (yield: 18%) of 4-(3,4-dichlorophenyl)-3-(2-naphthylmethoxy)-2-butanol.

The alcohol compound thus obtained was dissolved in methylene chloride, and the reaction was conducted in the same manner as in Reference Example 4 using phthalimide, triphenylphosphine and diethyl azodicarboxylate, to obtain the above-identified compound as white powder.

REFERENCE EXAMPLE 6

Preparation of
(E)-5-allyloxycarbonyl-4-methyl-4-pentenoic acid 34.4 g of triethyl phosphonoacetate was dissolved in 200 ml of ethanol, and 170 ml of a 1N sodium hydroxide aqueous solution was added thereto. The mixture was stirred at room temperature for 4 hours. Ethanol was distilled off under reduced pressure from the reaction solution. The residual solution was washed with ethyl ether, then acidified by an addition of concentrated hydrochloric acid and then extracted twice with ethyl acetate. The extract solution was washed with a saturated sodium chloride aqueous solution and then dried over anhydrous magnesium sulfate. The drying agent was separated by filtration, and then the solvent was distilled off under reduced pressure to obtain 29.2 g of diethylphosphonoacetic acid.

29.2 g of the diethylphosphonoacetic acid thus obtained was dissolved in 350 ml of methylene chloride, and 17.8 g of allyl alcohol, 1.92 g of 4-dimethylaminopyridine and 29.0 g of 1-ethyl-3-(3-methylaminopropyl)carbodiimide hydrochloride were added thereto with stirring under cooling with ice. The mixture was stirred at room temperature overnight. The reaction solution was evaporated under reduced pressure. The residue was dissolved in ethyl acetate, then sequentially washed with 1N hydrochloric acid, water, a saturated sodium hydrogencarbonate aqueous solution and a saturated sodium chloride aqueous solution, and dried over anhydrous magnesium sulfate. The drying agent was separated by filtration, and then the solvent was distilled off under reduced pressure to obtain 28.9 g of allyl diethylphosphonoacetate.

28.9 g of the allyl ester compound thus obtained was dissolved in 250 ml of tetrahydrofuran, and 5.5 g of 60% oily sodium hydride was added thereto with stirring under cooling with ice. The mixture was stirred for 30 minutes. Then, 150 ml of a tetrahydrofuran solution of 31.9 g of benzhydryl levulinate (which was prepared by reacting levulinic acid with diphenyldiazomethane in acetone) was added thereto, and the mixture was stirred at room temperature for 13 hours. The reaction solution was neutralized with acetic acid, and then the solvent was distilled off under reduced pressure. The residue was extracted by an addition of ethyl acetate and water. The organic layer was dried over anhydrous magnesium sulfate. Then, the solvent was distilled off under reduced pressure. The residue was purified by medium pressure liquid chromatography (hexane/ethyl acetate=13/1) to obtain 14.4 g (yield: 35%) of a benzhydryl ester of the above-identified compound.

7.61 g of the benzhydryl ester compound thus obtained was added to 35 ml of formic acid, and the mixture was stirred at room temperature for 4 hours. Then, the solvent was distilled off under reduced pressure, and the residue was purified by silica gel column chromatography (chloroform/methanol=20/1) to obtain 3.85 g (yield: 93%) of the above-identified compound as colorless oily substance.

REFERENCE EXAMPLE 7

Preparation of tert-butyl (3R, 5S)-5-methoxycarbonyl-3,5-O-isopropylidene-3,5-dihydroxypentanoate 132 g of mono-tert-butyl malonate was dissolved in 1.5 l of tetrahydrofuran, and 49.2 g of magnesium chloride and 134 ml of triethylamine were added thereto with stirring under cooling with ice. The mixture was stirred at room temperature for 3 hours. Added to this solution was a liquid separately prepared by stirring 60.0 g of 2,2-dimethyl-1,3-dioxolan-4-on-5-ylacetic acid (Tetrahedron Letter, vol. 28, p. 1685 (1987)) in a liquid mixture of 500 ml of tetrahydrofuran and 100 ml of dimethylformamide together with 64.2 g of 1,1'-carbonyldiimidazole at room temperature for 2 hours. The mixture was stirred at room temperature overnight. Insoluble matters were separated by filtration. Then, the filtrate was evaporated to dryness under reduced pressure. The residue was dissolved in a liquid mixture of ethyl ether and water and then adjusted to pH 3 to 4 by an addition of 1N hydrochloric acid. The organic layer was collected by separation, then washed with a saturated sodium chloride aqueous solution and dried over anhydrous magnesium sulfate. Then, the solvent was distilled off under reduced pressure. The residue was dissolved in ethyl acetate and then passed through a column of 300 g of activated aluminum oxide. The solution passed through the column was evaporated to dryness under reduced pressure to obtain 72.4 g (yield: 77%) of tert-butyl 4-(2,2-dimethyl-1,3-dioxolan-4-on-5-yl)-3-oxobutyrate.

62.4 g of the β-ketobutyrate thus obtained was dissolved in 500 ml of methanol, and 460 ml of a 0.5N sodium hydroxide aqueous solution was added thereto. The mixture was stirred at room temperature for 15 minutes. The reaction solution was adjusted to pH 3 to 4 by an addition of 1N hydrochloric acid and then extracted twice by an addition of ethyl acetate. The extract solutions were put together, washed with a saturated sodium chloride aqueous solution and dried over anhydrous magnesium sulfate. Then, the solvent was distilled off under reduced pressure. The residue was dissolved in 300 ml of ethyl ether, and an ethyl ether solution of diazomethane (appropriate amount) was added thereto, and the mixture was stirred at room temperature for 30 minutes. Then, the solvent was distilled off under reduced pressure to obtain 38.2 g (yield: 78%) of tert-butyl (5S)-5-methoxycarbonyl-5-hydroxy-3-oxopentanoate.

19.7 g of the diester compound thus obtained was dissolved in 300 ml of tetrahydrofuran, and 128 ml of a 1M tetrahydrofuran solution of triethylborane was added thereto. The mixture was stirred at room temperature for 30 minutes. The reaction solution was cooled to −70° C., and 63 ml of methanol and 6.05 g of sodium borohydride were added thereto with stirring. The mixture was stirred at a temperature of from −50° C. to −40° C. for 1 hour. Then, 30 ml of a 30% hydrogen peroxide aqueous solution was added with stirring under cooling at the same temperature, and the mixture was stirred at room temperature for 1 hour. Then, the mixture was adjusted to pH 3 by an addition of 1N hydrochloric acid. The reaction solution was extracted by an addition of ethyl acetate, and the extract solution was washed with a saturated sodium chloride aqueous solution and then dried over anhydrous magnesium sulfate. The drying agent was separated by filtration, and then the solvent was distilled off under reduced pressure. The residue was dissolved in ethyl acetate and then passed through a column of 50 g of silica gel. The solutions passed through the column were put together, and the solvent was distilled off under reduced pressure. The residue was dissolved in 200 ml of 2,2-dimethoxypropane. Then, 0.24 g of p-toluenesulfonic acid was added thereto, and the mixture was left to stand at room temperature for 24 hours. 2 ml of pyridine was added to the reaction solution, and the mixture was evaporated to dryness under reduced pressure. The residue was purified by column chromatography packed with 200 g of activated aluminum oxide (hexane+hexane/ethyl acetate=4/1) and then treated with hexane to obtain 8.0 g (yield: 33%) of the above-identified compound as white crystalline powder.

The compounds of the present invention are novel compounds not disclosed in any literatures and have excellent inhibitory activities against squalene synthase. Thus, they are useful for treatment and prophylaxis of hypercholesterolemia, hyperlipemia and arteriosclerosis. Further, the compounds of the present invention have antifungal activities and thus are useful also as therapeutic agents and preventive agents for various diseases attributable to infection with fungi.

We claim:

1. A compound of the formula (III-b$^1$):

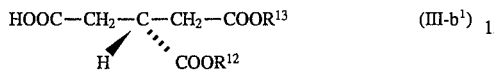

wherein each of $R^{12}$ and $R^{13}$, which are the same or different, is a carboxyl-protecting group, or the formula (III-b$^2$):

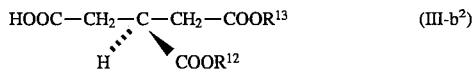

wherein $R^{12}$ and $R^{13}$ are as defined above; and wherein said carboxyl-protecting group for both the compounds of the formula (III-b$^1$) and (III-b$^2$) is selected from the group consisting of halo-substituted lower alkyl, lower alkanoyloxyalkyl, lower alkoxycarbonyloxyalkyl, lower alkenyl, aralkyl, 5-substituted-2-oxo-1,3-dioxyl-4-yl methyl, lower alkylsilyl, indanyl, phthalidyl and methoxymethyl.

2. The compound of claim 1, which has the formula (III-b$^1$).

3. The compound of claim 1, which has the formula (III-b$^2$).

4. The compound of claim 1, wherein said carboxyl-protecting group 5-substituted-2-oxo-1,3-dioxyl-4-yl methyl is 5-methyl-2-oxy-1,3-dioxyl-4-yl methyl.

5. The compound of claim 1, wherein said carboxyl-protecting group is selected from the group consisting of 2,2,2-trichloroethyl, 2,2,2-trifluoroethyl, acetoxymethyl, propionyloxymethyl, pivaloyloxymethyl, 1-acetoxyethyl, 1-pivaloyloxyethyl, 1-(methoxycarbonyloxy)ethyl, 1-(ethoxycarbonyloxy)ethyl, 1-(isopropoxycarbonyloxy)ethyl, 2-propenyl, 2-chloro-2-propenyl, 3-methoxycarbonyl-2-propenyl, 2-methyl-2-propenyl, 2-butenyl, cinnamyl, benzyl, p-methoxybenzyl, 3,4-dimethoxybenzyl, o-nitrobenzyl, p-nitrobenzyl, benzhydryl, bis(p-methoxyphenyl)methyl, trityl, 5-methyl-2-oxo-1,3-dioxol-4-yl)methyl, trimethylsilyl, tert-butyldimethylsilyl, indanyl, phthalidyl and methoxymethyl.

6. The compound of claim 5, wherein said carboxyl-protecting group is selected from the group consisting of 2-propenyl, benzyl, p-methoxybenzyl, benzhydryl and trityl.

* * * * *